US010081659B2

(12) United States Patent
Chiorini et al.

(10) Patent No.: US 10,081,659 B2
(45) Date of Patent: Sep. 25, 2018

(54) ADENO-ASSOCIATED VECTORS FOR ENHANCED TRANSDUCTION AND REDUCED IMMUNOGENICITY

(71) Applicants: The United States of America, as represented by the Secretary, Dept. of Health and Human Services, Washington, DC (US); University of Florida Research Foundation, Inc., Gainesville, FL (US)

(72) Inventors: John A. Chiorini, Dayton, MD (US); Sandra Wainer, Bethesda, MD (US); Mavis Agbandje-McKenna, Gainesville, FL (US); Sujata Halder, Gainesville, FL (US)

(73) Assignees: The United States of America, as represented by the Secretary, Dept. of Health and Human Services, Washington, DC (US); University of Florida Research Foundation, Inc., Gainesville, FL (US)

( * ) Notice: Subject to any disclaimer, the term of this patent is extended or adjusted under 35 U.S.C. 154(b) by 79 days.

(21) Appl. No.: 15/092,482

(22) Filed: Apr. 6, 2016

(65) Prior Publication Data

US 2016/0289275 A1     Oct. 6, 2016

Related U.S. Application Data

(60) Provisional application No. 62/309,025, filed on Mar. 16, 2016, provisional application No. 62/143,524, (Continued)

(51) Int. Cl.
*A61K 39/12* (2006.01)
*C07K 14/005* (2006.01)
*A61K 48/00* (2006.01)

(52) U.S. Cl.
CPC ........ *C07K 14/005* (2013.01); *A61K 48/0008* (2013.01); *A61K 48/0075* (2013.01);
(Continued)

(58) Field of Classification Search
None
See application file for complete search history.

(56) References Cited

U.S. PATENT DOCUMENTS 6,040,183 A     3/2000 Ferrari et al.
6,093,570 A     7/2000 Ferrari et al.
(Continued)

OTHER PUBLICATIONS

Gao et al. Adeno-associated viruses undergo substantial evolution in primates during natural infections. Proc. Natl. Assc. Sci. USA, 2003; 100(10):6081-6086.*
(Continued)

*Primary Examiner* — Janet L Andres
*Assistant Examiner* — Stuart W Snyder
(74) *Attorney, Agent, or Firm* — Sheridan Ross P.C.

(57) ABSTRACT

A modified adeno-associated virus (AAV) capsid protein comprising at least one non-native amino acid that confers to the modified AAV particles new properties, such as increased transduction efficiency and reduced immunogenicity. These modified AAV proteins and particles are particularly useful for gene therapy and the treatment of various diseases and conditions.

13 Claims, 17 Drawing Sheets

Specification includes a Sequence Listing.

Related U.S. Application Data filed on Apr. 6, 2015, provisional application No. 62/309,025, filed on Mar. 16, 2016.

(52) U.S. Cl.
CPC .............. *C12N 2750/14122* (2013.01); *C12N 2750/14143* (2013.01); *C12N 2810/6027* (2013.01)

(56) References Cited

U.S. PATENT DOCUMENTS

| | | |
|---|---|---|
| 6,468,524 B1 | 10/2002 | Chiorini et al. |
| 6,855,314 B1 | 2/2005 | Chiorini et al. |
| 6,984,517 B1 | 1/2006 | Chiorini et al. |
| 7,220,577 B2 | 5/2007 | Zolotukhin |
| 7,259,151 B2 | 8/2007 | Arbetman et al. |
| 7,479,554 B2 | 1/2009 | Chiorini et al. |
| 7,968,340 B2 | 6/2011 | Hallek et al. |
| 8,299,215 B2 | 10/2012 | Davidson et al. |
| 8,802,080 B2 | 8/2014 | Warrington et al. |
| 8,889,641 B2 | 11/2014 | Asokan et al. |
| 8,927,269 B2 | 1/2015 | Bossis et al. |
| 2004/0180440 A1 | 9/2004 | Solotukhin |
| 2005/0287122 A1 | 12/2005 | Bartlett et al. |
| 2006/0051333 A1 | 3/2006 | Arbetman et al. |
| 2006/0093589 A1 | 5/2006 | Warrington et al. |
| 2006/0292117 A1 | 12/2006 | Loiler et al. |
| 2007/0196338 A1 | 8/2007 | Samulski et al. |
| 2009/0202490 A1 | 8/2009 | Schaffer et al. |
| 2009/0286321 A1 | 11/2009 | Warrington et al. |
| 2010/0260800 A1 | 10/2010 | Bartlett et al. |
| 2011/0171262 A1 | 7/2011 | Bakker et al. |
| 2012/0009268 A1 | 1/2012 | Asokan et al. |
| 2014/0056854 A1 | 2/2014 | Asokan et al. |
| 2014/0162319 A2 | 6/2014 | Hareendran et al. |
| 2014/0336245 A1 | 11/2014 | Mingozzi et al. |
| 2014/0364338 A1 | 12/2014 | Schaffer et al. |
| 2015/0005369 A1 | 1/2015 | Muzyczka et al. |
| 2015/0023924 A1 | 1/2015 | High et al. |

OTHER PUBLICATIONS

UniProtKB—Q6JC63 (Q6JC63_9VIRU; 2004).*
DiPrimio et al. "Surface Loop Dynamics in Adeno-Associated Virus Capsid Assembly," Journal of Virology, Jun. 2008, vol. 82, No. 11, pp. 5178-5189.
Hauck et al. "Characterization of Tissue Tropism Determinants of Adeno-Associated Virus Type 1," Journal of Virology, Feb. 2003, vol. 77, No. 4, pp. 2768-2774.
Hida et al. "Sites in the AAV5 capsid tolerant to deletions and tandem duplications," Arch Biochem Biophys, Apr. 2010, vol. 496, No. 1, pp. 1-8 (Abstract Only).
Huttner et al. "Genetic modifications of the adeno-associated virus type 2 capsid reduce the affinity and the neutralizing effects of human serum antibodies." Gene Therapy, Dec. 2003, vol. 10, No. 26, pp. 2139-2147.
Kern et al. "Identification of a Heparin-Binding Motif on Adeno-Associated Virus Type 2 Capsids," Journal of Virology, Oct. 2003, vol. 77, No. 20, pp. 11072-11081.
Koerber et al. "Construction of diverse adeno-associated viral libraries for directed evolution of enhanced gene delivery vehicles," Nature Protocols, 2006, vol. 1, No. 2, pp. 701-706.
Kotterman et al. "Engineering adeno-associated viruses for clinical gene therapy," Nature Reviews Genetics, Jul. 2014, vol. 15, pp. 445-451.
Maheshri et al. "Directed evolution of adeno-associated virus yields enhanced gene delivery vectors," Nature Biotechnology, Feb. 2006, vol. 24, No. 2, pp. 198-204.
Opie et al. "Identification of Amino Acid Residues in the Capsid Protiens of Adeno-Associated Virus Type 2 That Contribute to Heparan Sulfate Proteoglycan Binding," Journal of Virology, Jun. 2003, vol. 77, No. 12, pp. 6995-7006.
Pandya et al. "Rationally designed capsid and transgene cassette of AAV6 vectors for dendritic cell-based cancer immunotherapy." Immunology Cell Biology, Feb. 2014, vol. 92, No. 2, pp. 116-123 (Abstract Only).
Shen et al. "Multiple Roles for Sialylated Glycans in Determining the Cardiopulmonary Tropism of Aden-Associated Virus 4," Journal of Virology, Dec. 2013, vol. 87, No. 24, pp. 13206-13213.
White et al. "Genetic Modification of Adeno-Associated Viral Vector Type 2 Capsid Enhances Gene Transfer Efficiency in Polarized Human Airway Epithelial Cells," Human Gene Therapy, Dec. 2008, vol. 19, pp. 1407-1414.
Wu et al. "Mutational Analysis of the Adeno-Associated Virus Type 2 (AAV2) Capsid Gene and Construction of AAVZ Vectors with Altered Tropism," Journal of Virology, Sep. 2000, vol. 74, No. 18, pp. 8635-8647.

\* cited by examiner

Alignment of AAV5 (SEQ ID NO:6) with: AAV2 (SEQ ID NO:2), AAV7 (SEQ ID NO:46), AAV8 (SEQ ID NO:47), and AAV9 (SEQ ID NO:8)

```
AAV7  MAADGYLPDWLEDNLSEGIREWWDLKPGAPKPKANQQKQDNGRGLVLPGYKYLGPFNGLD 60
AAV8  ------------------------------------------------------------
AAV9  MAADGYLPDWLEDNLSEGIREWWALKPGAPQPKANQQHQDNARGLVLPGYKYLGPGNGLD 60
AAV2  MAADGYLPDWLEDTLSEGIRQWWKLKPGPPPPKPAERHKDDSRGLVLPGYKYLGPFNGLD 60
AAV5  MSFVDHPPDWLEEVG-EGLREFLGLEAGPPKPKPNQQHQDQARGLVLPGYNYLGPGNGLD 59

AAV7  KGEPVNAADAAALEHDKAYDQQLKAGDNPYLRYNHADAEFQERLQEDTSFGGNLGRAVFQ 120
AAV8  ------------------------------------------------------------
AAV9  KGEPVNAADAAALEHDKAYDQQLKAGDNPYLKYNHADAEFQERLKEDTSFGGNLGRAVFQ 120
AAV2  KGEPVNEADAAALEHDKAYDRQLDSGDNPYLKYNHADAEFQERLKEDTSFGGNLGRAVFQ 120
AAV5  RGEPVNRADEVAREHDISYNEQLEAGDNPYLKYNHADAEFQEKLADDTSFGGNLGKAVFQ 119

AAV7  AKKRVLEPLGLVEEGAKTAPAKKRPVEPSPQRSPDSSTGIGKKGQQPARKRLNFGQTGDS 180
AAV8  ------------------------------------------------------------
AAV9  AKKRLLEPLGLVEEAAKTAPGKKRPVEQSPQ-EPDSSAGIGKSGAQPAKKRLNFGQTGDT 179
AAV2  AKKRVLEPLGLVEEPVKTAPGKKRPVEHSPV-EPDSSSGTGKAGQQPARKRLNFGQTGDA 179
AAV5  AKKRVLEPFGLVEEGAKTAPTGKRIDDHFPKRKKARTEEDSKPS----------TSSDA 168

AAV7  ESVPD-PQPLGEPPAAPSSVGSGTVAAGGGAPMADNNEGADGVGNASGNWHCDSTWLGDR 239
AAV8  --------------------------------DGVGSSSGNWHCDSTWLGDR 20
AAV9  ESVPD-PQPIGEPPAAPSGVGSLTMASGGGAPVADNNEGADGVGSSSGNWHCDSQWLGDR 238
AAV2  DSVPD-PQPLGQPPAAPSGLGTNTMATGSGAPMADNNEGADGVGNSSGNWHCDSTWMGDR 238
AAV5  EAGPSGSQQLQIPAQPASSLGADTMSAGGGGPLGDNNQGADGVGNASGDWHCDSTWMGDR 228
                                      ****.:**:***** *:***

AAV7  VITTSTRTWALPTYNNHLYKQISSETAG-STNDNTYFGYSTPWGYFDFNRFHCHFSPRDW 298
AAV8  VITTSTRTWALPTYNNHLYKQISNGTSGGATNDNTYFGYSTPWGYFDFNRFHCHFSPRDW 80
AAV9  VITTSTRTWALPTYNNHLYKQISNSTSGGSSNDNAYFGYSTPWGYFDFNRFHCHFSPRDW 298
AAV2  VITTSTRTWALPTYNNHLYKQIS--SQSGASNDNHYFGYSTPWGYFDFNRFHCHFSPRDW 296
AAV5  VVTKSTRTWVLPSYNNHQYREIKSGSVD-GSNANAYFGYSTPWGYFDFNRFHSHWSPRDW 287
      *:*.*****.**:**** *::*.   :  . .:* * *****************.*:*****

AAV7  QRLINNNWGFRPKKLRFKLFNIQVKEVTTNDGVTTIANNLTSTIQVFSDSEYQLPYVLGS 358
AAV8  QRLINNNWGFRPKRLSFKLFNIQVKEVTQNEGTKTIANNLTSTIQVFTDSEYQLPYVLGS 140
AAV9  QRLINNNWGFRPKRLNFKLFNIQVKEVTDNNGVKTIANNLTSTVQVFTDSDYQLPYVLGS 358
AAV2  QRLINNNWGFRPKRLNFKLFNIQVKEVTQNDGTTTIANNLTSTVQVFTDSEYQLPYVLGS 356
AAV5  QRLINNYWGFRPRSLRVKIFNIQVKEVTVQDSTTIANNLTSTVQVFTDDDYQLPYVVGN 347
      ****** *****: * .*:********* :...**********:***:*.:******:*.

AAV7  AHQGCLPPFPADVFMIPQYGYLTLN--NGSQSVGRSSFYCLEYFPSQMLRTGNNFEFSYS 416
AAV8  AHQGCLPPFPADVFMIPQYGYLTLN--NGSQAVGRSSFYCLEYFPSQMLRTGNNFQFTYT 198
AAV9  AHEGCLPPFPADVFMIPQYGYLTLN--DGSQAVGRSSFYCLEYFPSQMLRTGNNFQFSYE 416
AAV2  AHQGCLPPFPADVFMVPQYGYLTLN--NGSQAVGRSSFYCLEYFPSQMLRTGNNFTFSYT 414
AAV5  GTEGCLPAFPPQVFTLPQYGYATLNRDNTENPTERSSFFCLEYFPSKMLRTGNNFEFTYN 407
       . :****.**.:** :***** ***    :  .:... ****.*******:********.*:*
```

Figure 9

```
AAV7  FEDVPFHSSYAHSQSLDRLMNPLIDQYLYYLARTQSNPGGTAGNRELQFYQGGPSTMAEQ  476
AAV8  FEDVPFHSSYAHSQSLDRLMNPLIDQYLYYLSRTQTT-GGTANTQTLGFSQGGPNTMANQ  257
AAV9  FENVPFHSSYAHSQSLDRLMNPLIDQYLYYLSKTING--SGQNQQTLKFSVAGPSNMAVQ  474
AAV2  FEDVPFHSSYAHSQSLDRLMNPLIDQYLYYLSRTNTP-SGTTTQSRLQFSQAGASDIRDQ  473
AAV5  FEEVPFHSSFAPSQNLFKLANPLVDQYLYRFVSTNNT-------GGVQFNKNLAGRYANT  460
      **:*******:* **.* :* ***:*****  :   * .         : *    ..

AAV7  AKNWLPGPCFRQQRVSKTLDQNNNSNFAWTGATKYHLNGRNSLVNPGVAMATHKDDEDRF  536
AAV8  AKNWLPGPCYRQQRVSTTTGQNNNSNFAWTAGTKYHLNGRNSLANPGIAMATHKDDEERF  317
AAV9  GRNYIPGPSYRQQRVSTTVTQNNNSEFAWPGASSWALNGRNSLMNPGPAMASHKEGEDRF  534
AAV2  SRNWLPGPCYRQQRVSKTSADNNNSEYSWTGATKYHLNGRDSLVNPGPAMASHKDDEEKF  533
AAV5  YKNWFPGPMGRTQGWNLGSGVNRASVSAFATTNRMELEGASYQVPPQPNGMTNNLQGSNT  520
      :*::***  * *    . *.*  ::.    *:*  .    *       :::   ..

AAV7  FPSSGVLIFGKTGAT---NKTTLE-NVLMTNEEEIRPTNPVATEEYGIVSSNLQAANTAA  592
AAV8  FPSNGILIFGKQNAAR--DNADYS-DVMLTSEEEIKTTNPVATEEYGIVADNLQQQNTAP  374
AAV9  FPLSGSLIFGKQGTGR--DNVDAD-KVMITNEEEIKTTNPVATESYGQVATNHQSAQAQA  591
AAV2  FPQSGVLIFGKQGSEK--TNVDIE-KVMITDEEEIRTTNPVATEQYGSVSTNLQRGNRQA  590
AAV5  YALENTMIFNSQPANPGTTATYLEGNMLITSESETQPVNRVAYNVGGQMATNNQSSTTAP  580
      :.  .. :**..  :          . .:::*.*.* :..* **  :  * ::  * *      .

AAV7  QTQVVNNQGALPGMVWQNRDVYLQGPIWAKIPHTDGNFHPSPLMGGFGLKHPPPQILIKN  652
AAV8  QIGTVNSQGALPGMVWQNRDVYLQGPIWAKIPHTDGNFHPSPLMGGFGLKHPPPQILIKN  434
AAV9  QTGWVQNQGILPGMVWQDRDVYLQGPIWAKIPHTDGNFHPSPLMGGFGMKHPPPQILIKN  651
AAV2  ATADVNTQGVLPGMVWQDRDVYLQGPIWAKIPHTDGHFHPSPLMGGFGLKHPPPQILIKN  650
AAV5  ATGTYNLQEIVPGSVWMERDVYLQGPIWAKIPETGAHFHPSPAMGGFGLKHPPPMMLIKN  640
        :  *   :** ** :*************.*..:***** *****:***** :****

AAV7  TPVPANPPEVFTPAKFASFITQYSTGQVSVEIEWELQKENSKRWNPEIQYTSNFEKQTGV  712
AAV8  TPVPADPPTTFNQSKLNSFITQYSTGQVSVEIEWELQKENSKRWNPEIQYTSNYYKSTSV  494
AAV9  TPVPADPPTAFNKDKLNSFITQYSTGQVSVEIEWELQKENSKRWNPEIQYTSNYYKSNNV  711
AAV2  TPVPANPSTTFSAAKFASFITQYSTGQVSVEIEWELQKENSKRWNPEIQYTSNYNKSVNV  710
AAV5  TPVPGN-ITSFSDVPVSSFITQYSTGQVTVEMEWELKKENSKRWNPEIQYTNNYNDPQFV  699
      ****.:    *.   . ***********:**:****:************.*: .    *

AAV7  DFAVDSQGVYSEPRPIGTRYLTRNL  737
AAV8  DFAVNTEGVYSEPRPIGTRYLTRNL  519
AAV9  EFAVNTEGVYSEPRPIGTRYLTRNL  736
AAV2  DFTVDTNGVYSEPRPIGTRYLTRNL  735
AAV5  DFAPDSTGEYRTTRPIGTRYLTRPL  724
```

Figure 9 - Continued

Subretinal L587T
3E12 vg/mL Real time exposure
L587T
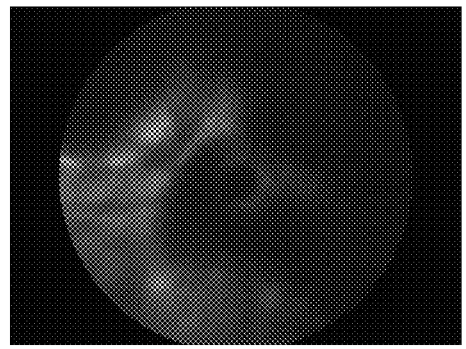
Negative control
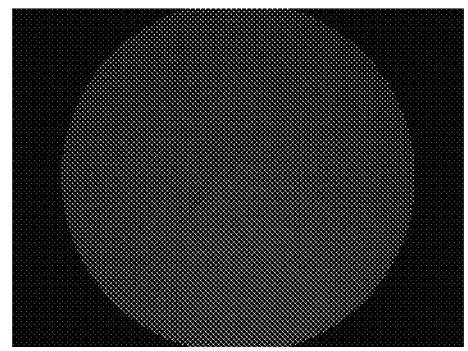
Figure 10

SEQUENCE LISTING

<160> NUMBER OF SEQ ID NOS: 47

<210> SEQ ID NO 1
<211> LENGTH: 736
<212> TYPE: PRT
<213> ORGANISM: adeno-associated virus 1

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220
```

-continued

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala

-continued

```
                        645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 2
<211> LENGTH: 735
<212> TYPE: PRT
<213> ORGANISM: adeno-associated virus 2

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
            435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
```

```
                    705                 710                 715                 720
Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: adeno-associated virus 3

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Lys Thr Ala Pro Gly Lys Lys Gly
        130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
            340                 345                 350
```

```
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
        435                 440                 445
Gln Gly Thr Thr Ser Gly Thr Thr Asn Gln Ser Arg Leu Leu Phe Ser
    450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
        515                 520                 525
Asp Asp Glu Glu Lys Phe Phe Pro Met His Gly Asn Leu Ile Phe Gly
    530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Gly Thr Val Asn His Gln Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Pro Gln Ile Met Ile Lys Asn Thr Pro Val Pro Ala
                645                 650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: adeno-associated virus 3

<400> SEQUENCE: 4
```

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Leu Glu His Asp Lys Ala Tyr Asp
65              70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
        130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
        180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
            405                 410                 415
```

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 5
<211> LENGTH: 734
<212> TYPE: PRT
<213> ORGANISM: adeno-associated virus 4

<400> SEQUENCE: 5

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

```
Asn Ala Ala Asp Ala Ala Ala Leu Glu His Asp Lys Ala Tyr Asp Gln
 65                  70                  75                  80

Gln Leu Lys Ala Gly Asp Asn Pro Tyr Leu Lys Tyr Asn His Ala Asp
                 85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
            115                 120                 125

Gly Leu Val Glu Gln Ala Gly Glu Thr Ala Pro Gly Lys Lys Arg Pro
130                 135                 140

Leu Ile Glu Ser Pro Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Gly Gly Ala Ala Val Glu Gly
            195                 200                 205

Gly Gln Gly Ala Asp Gly Val Gly Asn Ala Ser Gly Asp Trp His Cys
210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Asn Trp Gly Met Arg Pro Lys Ala Met Arg Val
            290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Leu Val Thr Gly Asn Thr Ser Gln Gln Gln Thr Asp Arg Asn
            370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480
```

```
Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
            530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
            610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
            690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 6
<211> LENGTH: 724
<212> TYPE: PRT
<213> ORGANISM: adeno-associated virus 5

<400> SEQUENCE: 6

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
            115                 120                 125
```

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Leu Gly Ala Asp Thr
            180                 185                 190

Met Ser Ala Gly Gly Gly Pro Leu Gly Asp Asn Gln Gly Ala
        195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
    275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
    355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
    435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
    515                 520                 525

Phe Asn Ser Gln Pro Ala Asn Pro Gly Thr Thr Ala Thr Tyr Leu Glu
530                 535                 540

```
Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 7
<211> LENGTH: 736
<212> TYPE: PRT
<213> ORGANISM: adeno-associated virus 6

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190
```

```
Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
```

```
                    610                 615                 620
Thr Asp Gly His Phe His Pro Ser Pro Leu Met Gly Phe Gly Leu
625                 630                 635                 640

Lys His Pro Pro Gln Ile Leu Ile Lys Asn Thr Pro Val Pro Ala
                    645                 650                 655

Asn Pro Pro Ala Glu Phe Ser Ala Thr Lys Phe Ala Ser Phe Ile Thr
                    660                 665                 670

Gln Tyr Ser Thr Gly Gln Val Ser Val Glu Ile Glu Trp Glu Leu Gln
                    675                 680                 685

Lys Glu Asn Ser Lys Arg Trp Asn Pro Glu Val Gln Tyr Thr Ser Asn
                    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                    725                 730                 735

<210> SEQ ID NO 8
<211> LENGTH: 736
<212> TYPE: PRT
<213> ORGANISM: adeno-associated virus 9

<400> SEQUENCE: 8

Met Ala Ala Asp Gly Tyr Leu Pro Asp Trp Leu Glu Asp Asn Leu Ser
1                   5                   10                  15

Glu Gly Ile Arg Glu Trp Trp Ala Leu Lys Pro Gly Ala Pro Gln Pro
                    20                  25                  30

Lys Ala Asn Gln Gln His Gln Asp Asn Ala Arg Gly Leu Val Leu Pro
                    35                  40                  45

Gly Tyr Lys Tyr Leu Gly Pro Gly Asn Gly Leu Asp Lys Gly Glu Pro
                    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                    85                  90                  95

Asp Ala Glu Phe Gln Glu Arg Leu Lys Glu Asp Thr Ser Phe Gly Gly
                    100                 105                 110

Asn Leu Gly Arg Ala Val Phe Gln Ala Lys Lys Arg Leu Leu Glu Pro
                    115                 120                 125

Leu Gly Leu Val Glu Glu Ala Ala Lys Thr Ala Pro Gly Lys Lys Arg
                    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                    165                 170                 175

Gly Asp Thr Glu Ser Val Pro Asp Pro Gln Pro Ile Gly Glu Pro Pro
                    180                 185                 190

Ala Ala Pro Ser Gly Val Gly Ser Leu Thr Met Ala Ser Gly Gly Gly
                    195                 200                 205

Ala Pro Val Ala Asp Asn Asn Glu Gly Ala Asp Gly Val Gly Ser Ser
                    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                    245                 250                 255
```

-continued

```
Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
```

```
                    675                 680                 685
Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 9
<211> LENGTH: 742
<212> TYPE: PRT
<213> ORGANISM: adeno-associated virus 12

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320
```

```
Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Phe Pro Pro Phe Pro Asn Asp
        355                 360                 365

Val Phe Met Val Pro Gln Tyr Gly Tyr Cys Gly Val Thr Gly Lys
    370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
                405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
        435                 440                 445

Ser Thr Thr Thr Gly Asn Ser Leu Asn Gln Gly Thr Ala Thr Thr Thr
    450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
    530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
        595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
    690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735

Phe Leu Thr His His Leu
```

<210> SEQ ID NO 10
<211> LENGTH: 733
<212> TYPE: PRT
<213> ORGANISM: adeno-associated virus

<400> SEQUENCE: 10

```
Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Ala Lys Thr Ala Pro Gly Lys Lys Arg Pro
    130                 135                 140

Val Glu Gln Ser Pro Ala Glu Pro Asp Ser Ser Ser Gly Ile Gly Lys
145                 150                 155                 160

Ser Gly Gln Gln Pro Ala Arg Lys Arg Leu Asn Phe Gly Gln Thr Gly
                165                 170                 175

Asp Thr Glu Ser Val Pro Asp Pro Gln Pro Leu Gly Gln Pro Pro Ala
            180                 185                 190

Ala Pro Ser Gly Val Gly Ser Thr Thr Met Ala Ser Gly Gly Gly Ala
        195                 200                 205

Pro Met Ala Asp Asn Asn Glu Gly Ala Asp Gly Val Gly Asn Ser Ser
    210                 215                 220

Gly Asn Trp His Cys Asp Ser Gln Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Thr Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Arg Leu Asn Phe Lys Leu Phe Asn Ile Gln Val Lys
305                 310                 315                 320

Glu Val Thr Gln Asn Asp Gly Thr Thr Thr Ile Ala Asn Asn Leu Thr
                325                 330                 335

Ser Thr Val Gln Val Phe Thr Asp Ser Glu Tyr Gln Leu Pro Tyr Val
            340                 345                 350

Leu Gly Ser Ala His Gln Gly Cys Leu Pro Pro Phe Pro Ala Asp Val
        355                 360                 365
```

Phe Met Val Pro Gln Tyr Gly Tyr Leu Thr Leu Asn Asn Gly Ser Gln
370                 375                 380

Ala Val Gly Arg Ser Ser Phe Tyr Cys Leu Glu Tyr Phe Pro Ser Gln
385                 390                 395                 400

Met Leu Arg Thr Gly Asn Asn Phe Gln Phe Ser Tyr Thr Phe Glu Asp
                405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Asn Arg Thr Gln
        435                 440                 445

Thr Ala Ser Gly Thr Gln Gln Ser Arg Leu Leu Phe Ser Gln Ala Gly
450                 455                 460

Pro Thr Ser Met Ser Leu Gln Ala Lys Asn Trp Leu Pro Gly Pro Cys
465                 470                 475                 480

Tyr Arg Gln Gln Arg Leu Ser Lys Gln Ala Asn Asp Asn Asn Asn Ser
                485                 490                 495

Asn Phe Pro Trp Thr Gly Ala Thr Lys Tyr His Leu Asn Gly Arg Asp
                500                 505                 510

Ser Leu Val Asn Pro Gly Pro Ala Met Ala Ser His Lys Asp Asp Lys
            515                 520                 525

Glu Lys Phe Phe Pro Met His Gly Thr Leu Ile Phe Gly Lys Glu Gly
530                 535                 540

Thr Asn Ala Asn Ala Asp Leu Glu Asn Val Met Ile Thr Asp Glu
545                 550                 555                 560

Glu Glu Ile Arg Thr Thr Asn Pro Val Ala Thr Glu Gln Tyr Gly Thr
                565                 570                 575

Val Ser Asn Asn Leu Gln Asn Ser Asn Ala Gly Pro Thr Thr Gly Thr
            580                 585                 590

Val Asn His Gln Gly Ala Leu Pro Gly Met Val Trp Gln Asp Arg Asp
        595                 600                 605

Val Tyr Leu Gln Gly Pro Ile Trp Ala Lys Ile Pro His Thr Asp Gly
610                 615                 620

His Phe His Pro Ser Pro Leu Met Gly Gly Phe Gly Leu Lys His Pro
625                 630                 635                 640

Pro Pro Gln Ile Met Ile Lys Asn Thr Pro Val Pro Ala Asn Pro Pro
                645                 650                 655

Thr Asn Phe Ser Ala Ala Lys Phe Ala Ser Phe Ile Thr Gln Tyr Ser
                660                 665                 670

Thr Gly Gln Val Ser Val Glu Ile Glu Trp Glu Leu Gln Lys Glu Asn
            675                 680                 685

Ser Lys Arg Trp Asn Pro Glu Ile Gln Tyr Thr Ser Asn Tyr Asn Lys
690                 695                 700

Ser Val Asn Val Asp Phe Thr Val Asp Thr Asn Gly Val Tyr Ser Glu
705                 710                 715                 720

Pro Arg Pro Ile Gly Thr Arg Tyr Leu Thr Arg Asn Leu
                725                 730

<210> SEQ ID NO 11
<211> LENGTH: 743
<212> TYPE: PRT
<213> ORGANISM: adeno-associated virus

<400> SEQUENCE: 11

Met Ser Leu Ile Ser Asp Ala Ile Pro Asp Trp Leu Glu Arg Leu Val
1               5                   10                  15

```
Lys Lys Gly Val Asn Ala Ala Ala Asp Phe Tyr His Leu Glu Ser Gly
             20                  25                  30

Pro Pro Arg Pro Lys Ala Asn Gln Gln Thr Gln Glu Ser Leu Glu Lys
         35                  40                  45

Asp Asp Ser Arg Gly Leu Val Phe Pro Gly Tyr Asn Tyr Leu Gly Pro
 50                  55                  60

Phe Asn Gly Leu Asp Lys Gly Glu Pro Val Asn Glu Ala Asp Ala Ala
 65                  70                  75                  80

Ala Leu Glu His Asp Lys Ala Tyr Asp Leu Glu Ile Lys Asp Gly His
             85                  90                  95

Asn Pro Tyr Phe Glu Tyr Asn Glu Ala Asp Arg Arg Phe Gln Glu Arg
             100                 105                 110

Leu Lys Asp Asp Thr Ser Phe Gly Gly Asn Leu Gly Lys Ala Ile Phe
         115                 120                 125

Gln Ala Lys Lys Arg Val Leu Glu Pro Phe Gly Leu Val Glu Asp Ser
130                 135                 140

Lys Thr Ala Pro Thr Gly Asp Lys Arg Lys Gly Glu Asp Glu Pro Arg
145                 150                 155                 160

Leu Pro Asp Thr Ser Ser Gln Thr Pro Lys Lys Asn Lys Lys Pro Arg
             165                 170                 175

Lys Glu Arg Pro Ser Gly Gly Ala Glu Asp Pro Gly Glu Gly Thr Ser
             180                 185                 190

Ser Asn Ala Gly Ala Ala Ala Pro Ala Ser Ser Val Gly Ser Ser Ile
         195                 200                 205

Met Ala Glu Gly Gly Gly Pro Val Gly Asp Ala Gly Gln Gly Ala
             210                 215                 220

Asp Gly Val Gly Asn Ser Ser Gly Asn Trp His Cys Asp Ser Gln Trp
225                 230                 235                 240

Leu Glu Asn Gly Val Val Thr Arg Thr Thr Arg Thr Trp Val Leu Pro
             245                 250                 255

Ser Tyr Asn Asn His Leu Tyr Lys Arg Ile Gln Gly Pro Ser Gly Gly
             260                 265                 270

Asp Asn Asn Asn Lys Phe Phe Gly Phe Ser Thr Pro Trp Gly Tyr Phe
         275                 280                 285

Asp Tyr Asn Arg Phe His Cys His Phe Ser Pro Arg Asp Trp Gln Arg
 290                 295                 300

Leu Ile Asn Asn Asn Trp Gly Ile Arg Pro Lys Ala Met Arg Phe Arg
305                 310                 315                 320

Leu Phe Asn Ile Gln Val Lys Glu Val Thr Val Gln Asp Phe Asn Thr
             325                 330                 335

Thr Ile Gly Asn Asn Leu Thr Ser Thr Val Gln Val Phe Ala Asp Lys
             340                 345                 350

Asp Tyr Gln Leu Pro Tyr Val Leu Gly Ser Ala Thr Glu Gly Thr Phe
             355                 360                 365

Pro Pro Phe Pro Ala Asp Ile Tyr Thr Ile Pro Gln Tyr Gly Tyr Cys
         370                 375                 380

Thr Leu Asn Tyr Asn Asn Glu Ala Val Asp Arg Ser Ala Phe Tyr Cys
385                 390                 395                 400

Leu Asp Tyr Phe Pro Ser Asp Met Leu Arg Thr Gly Asn Asn Phe Glu
             405                 410                 415

Phe Thr Tyr Thr Phe Glu Asp Val Pro Phe His Ser Met Phe Ala His
             420                 425                 430
```

Asn Gln Thr Leu Asp Arg Leu Met Asn Pro Leu Val Asp Gln Tyr Leu
            435                 440                 445

Trp Ala Phe Ser Ser Val Ser Gln Ala Gly Ser Ser Gly Arg Ala Leu
450                 455                 460

His Tyr Ser Arg Ala Thr Lys Thr Asn Met Ala Ala Gln Tyr Arg Asn
465                 470                 475                 480

Trp Leu Pro Gly Pro Phe Arg Asp Gln Gln Ile Phe Thr Gly Ala
                485                 490                 495

Ser Asn Ile Thr Lys Asn Asn Val Phe Ser Val Trp Glu Lys Gly Lys
                500                 505                 510

Gln Trp Glu Leu Asp Asn Arg Thr Asn Leu Met Gln Pro Gly Pro Ala
            515                 520                 525

Ala Ala Thr Thr Phe Ser Gly Glu Pro Asp Arg Gln Ala Met Gln Asn
        530                 535                 540

Thr Leu Ala Phe Ser Arg Thr Val Tyr Asp Gln Thr Thr Ala Thr Thr
545                 550                 555                 560

Asp Arg Asn Gln Ile Leu Ile Thr Asn Glu Asp Glu Ile Arg Pro Thr
                565                 570                 575

Asn Ser Val Gly Ile Asp Ala Trp Gly Ala Val Pro Thr Asn Asn Gln
                580                 585                 590

Ser Ile Val Thr Pro Gly Thr Arg Ala Ala Val Asn Asn Gln Gly Ala
            595                 600                 605

Leu Pro Gly Met Val Trp Gln Asn Arg Asp Ile Tyr Pro Thr Gly Thr
        610                 615                 620

His Leu Ala Lys Ile Pro Asp Thr Asp Asn His Phe His Pro Ser Pro
625                 630                 635                 640

Leu Ile Gly Arg Phe Gly Cys Lys His Pro Pro Gln Ile Phe Ile
                645                 650                 655

Lys Asn Thr Pro Val Pro Ala Asn Pro Ser Glu Thr Phe Gln Thr Ala
                660                 665                 670

Lys Val Ala Ser Phe Ile Asn Gln Tyr Ser Thr Gly Gln Cys Thr Val
            675                 680                 685

Glu Ile Phe Trp Glu Leu Lys Lys Glu Thr Ser Lys Arg Trp Asn Pro
690                 695                 700

Glu Ile Gln Phe Thr Ser Asn Phe Gly Asn Ala Ala Asp Ile Gln Phe
705                 710                 715                 720

Ala Val Ser Asp Thr Gly Ser Tyr Ser Glu Pro Arg Pro Ile Gly Thr
                725                 730                 735

Arg Tyr Leu Thr Lys Pro Leu
            740

<210> SEQ ID NO 12
<211> LENGTH: 736
<212> TYPE: PRT
<213> ORGANISM: adeno-associated virus

<400> SEQUENCE: 12

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
                20                  25                  30

Ala Asn Gln Gln Lys Gln Asp Asn Ala Arg Gly Leu Val Leu Pro Gly
            35                  40                  45

Tyr Lys Tyr Leu Gly Pro Gly Asn Gly Leu Asp Lys Gly Asp Pro Val
        50                  55                  60

```
Asn Phe Ala Asp Glu Val Ala Arg Glu His Asp Leu Ser Tyr Gln Lys
 65                  70                  75                  80

Gln Leu Glu Ala Gly Asp Asn Pro Tyr Leu Lys Tyr Asn His Ala Asp
                 85                  90                  95

Ala Glu Phe Gln Glu Lys Leu Ala Ser Asp Thr Ser Phe Gly Gly Asn
            100                 105                 110

Leu Gly Lys Ala Val Phe Gln Ala Lys Lys Arg Ile Leu Glu Pro Leu
        115                 120                 125

Gly Leu Val Glu Thr Pro Asp Lys Thr Ala Pro Ala Lys Lys Arg
130                 135                 140

Pro Leu Glu Gln Ser Pro Gln Glu Pro Asp Ser Ser Gly Val Gly
145                 150                 155                 160

Lys Lys Gly Lys Gln Pro Ala Arg Lys Arg Leu Asn Phe Asp Asp Glu
                165                 170                 175

Pro Gly Ala Gly Asp Gly Pro Pro Glu Gly Pro Ser Ser Gly Ala
            180                 185                 190

Met Ser Thr Glu Thr Glu Met Arg Ala Ala Gly Gly Asn Gly Gly
        195                 200                 205

Asp Ala Gly Gln Gly Ala Glu Gly Val Gly Asn Ala Ser Gly Asp Trp
210                 215                 220

His Cys Asp Ser Thr Trp Ser Glu Ser His Val Thr Thr Ser Thr
225                 230                 235                 240

Arg Thr Trp Val Leu Pro Thr Tyr Asn Asn His Leu Tyr Leu Arg Leu
                245                 250                 255

Gly Ser Ser Asn Ala Ser Asp Thr Phe Asn Gly Phe Ser Thr Pro Trp
            260                 265                 270

Gly Tyr Phe Asp Phe Asn Arg Phe His Cys His Phe Ser Pro Arg Asp
        275                 280                 285

Trp Gln Arg Leu Ile Asn Asn His Trp Gly Leu Arg Pro Lys Ser Met
        290                 295                 300

Gln Val Arg Ile Phe Asn Ile Gln Val Lys Glu Val Thr Thr Ser Asn
305                 310                 315                 320

Gly Glu Thr Thr Val Ser Asn Asn Leu Thr Ser Thr Val Gln Ile Phe
                325                 330                 335

Ala Asp Ser Thr Tyr Glu Leu Pro Tyr Val Met Asp Ala Gly Gln Glu
            340                 345                 350

Gly Ser Leu Pro Pro Phe Pro Asn Asp Val Phe Met Val Pro Gln Tyr
        355                 360                 365

Gly Tyr Cys Gly Leu Val Thr Gly Ser Ser Gln Asn Gln Thr Asp
        370                 375                 380

Arg Asn Ala Phe Tyr Cys Leu Glu Tyr Phe Pro Ser Gln Met Leu Arg
385                 390                 395                 400

Thr Gly Asn Asn Phe Glu Met Val Tyr Lys Phe Glu Asn Val Pro Phe
                405                 410                 415

His Ser Met Tyr Ala His Ser Gln Ser Leu Asp Arg Leu Met Asn Pro
            420                 425                 430

Leu Leu Asp Gln Tyr Leu Trp Glu Leu Gln Ser Thr Thr Ser Gly Gly
        435                 440                 445

Thr Leu Asn Gln Gly Asn Ser Ala Thr Asn Phe Ala Lys Leu Thr Lys
        450                 455                 460

Thr Asn Phe Ser Gly Tyr Arg Lys Asn Trp Leu Pro Gly Pro Met Met
465                 470                 475                 480
```

```
Lys Gln Gln Arg Phe Ser Lys Thr Ala Ser Gln Asn Tyr Lys Ile Pro
                485                 490                 495

Gln Gly Arg Asn Asn Ser Leu Leu His Tyr Glu Thr Arg Thr Thr Leu
            500                 505                 510

Asp Gly Arg Trp Ser Asn Phe Ala Pro Gly Thr Ala Met Ala Thr Ala
        515                 520                 525

Ala Asn Asp Ala Thr Asp Phe Ser Gln Ala Gln Leu Ile Phe Ala Gly
    530                 535                 540

Pro Asn Ile Thr Gly Asn Thr Thr Asp Ala Asn Asn Leu Met Phe
545                 550                 555                 560

Thr Ser Glu Asp Glu Leu Arg Ala Thr Asn Pro Arg Asp Thr Asp Leu
                565                 570                 575

Phe Gly His Leu Ala Thr Asn Gln Gln Asn Ala Thr Thr Val Pro Thr
            580                 585                 590

Val Asp Asp Val Asp Gly Val Gly Val Tyr Pro Gly Met Val Trp Gln
        595                 600                 605

Asp Arg Asp Ile Tyr Tyr Gln Gly Pro Ile Trp Ala Lys Ile Pro His
    610                 615                 620

Thr Asp Gly His Phe His Pro Ser Pro Leu Ile Gly Gly Phe Gly Leu
625                 630                 635                 640

Lys Ser Pro Pro Pro Gln Ile Phe Ile Lys Asn Thr Pro Val Pro Ala
                645                 650                 655

Asn Pro Ala Thr Thr Phe Ser Pro Ala Arg Ile Asn Ser Phe Ile Thr
            660                 665                 670

Gln Tyr Ser Thr Gly Gln Val Ala Val Lys Ile Glu Trp Glu Ile Gln
        675                 680                 685

Lys Glu Arg Ser Lys Arg Trp Asn Pro Glu Val Gln Phe Thr Ser Asn
    690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735

<210> SEQ ID NO 13
<211> LENGTH: 2203
<212> TYPE: DNA
<213> ORGANISM: adeno-associated virus 5

<400> SEQUENCE: 13
atgtcttttg ttgatcaccc tccagattgg ttggaagaag ttggtgaagg tcttcgcgag    60
ttttggggcc ttgaagcggg cccaccgaaa ccaaaaccca atcagcagca tcaagatcaa   120
gcccgtggtc ttgtgctgcc tggttataac tatctcggac ccggaaacgg tctcgatcga   180
ggagagcctg tcaacagggc agacgaggtc gcgcgagagc acgacatctc gtacaacgag   240
cagcttgagg cgggagacaa cccctacctc aagtacaacc acgcggacgc cgagtttcag   300
gagaagctcg ccgacgacac atccttcggg ggaaacctcg gaaaggcagt ctttcaggcc   360
aagaaaaggg ttctcgaacc ttttggcctg gttgagaggg tgctaagacg gccccctacc   420
ggaaagcgga tagacgacca cttttccaaaa agaaagaagg ctcggaccga agaggactcc   480
aagccttcca cctcgtcaga cgccgaagct ggacccagcg atcccagca gctgcaaatc   540 ccagcccaac cagcctcaag tttgggagct gatacaatgt ctgcggggag tggcggccca   600
ttgggcgaca taaccaagg tgccgatgga gtgggcaatg cctcgggaga ttggcattgc   660
gattccacgt ggatggggga cagagtcgtc accaagtcca cccgaacctg ggtgctgccc   720
```

```
agctacaaca accaccagta ccgagagatc aaaagcggct ccgtcgacgg aagcaacgcc    780
aacgcctact ttggatacag caccccctgg gggtactttg actttaaccg cttccacagc    840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgcccacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa ctttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgccccccgca gccgaacggc atgaccaaca cctccagggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcaggtggcc accaacaacc agagctccac cactgccccc   1740
gcgaccggca cgtacaacct ccaggaaatc gtgcccggca cgtgtggat ggagaggggac   1800
gtgtacctcc aaggacccat ctgggccaag atcccagaga cggggggcgca ctttcacccc   1860
tctccggcca tgggcggatt cggactcaaa cacccaccgc ccatgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaaactcc   2040
aagaggtgga acccagagat ccagtacaca aacaactaca acgaccccca gtttgtggac   2100
tttgccccgg acagcaccgg ggaatacaga accaccagac ctatcggaac ccgataccttt   2160
acccgacccc tttaacccat tcatgtcgca taccctcaat aaa                     2203
```

<210> SEQ ID NO 14
<211> LENGTH: 724
<212> TYPE: PRT
<213> ORGANISM: adeno-associated virus 5

<400> SEQUENCE: 14

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

```
Leu Gly Lys Ala Val Phe Gln Ala Lys Lys Arg Val Leu Glu Pro Phe
            115                 120                 125
Gly Leu Val Glu Glu Gly Ala Lys Thr Ala Pro Thr Gly Lys Arg Ile
            130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Pro Leu Gly Asp Asn Asn Gln Gly Ala
            195                 200                 205
Asp Gly Val Gly Asn Ala Ser Gly Asp Trp His Cys Asp Ser Thr Trp
            210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
            275                 280                 285
Arg Leu Ile Asn Asn Tyr Trp Gly Phe Arg Pro Arg Ser Leu Arg Val
            290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gln Tyr Gly Tyr
            355                 360                 365
Ala Thr Leu Asn Arg Asp Asn Thr Glu Asn Pro Thr Glu Arg Ser Ser
            370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
            435                 440                 445
Phe Asn Lys Asn Leu Ala Gly Arg Tyr Ala Asn Thr Tyr Lys Asn Trp
450                 455                 460
Phe Pro Gly Pro Met Gly Arg Thr Gln Gly Trp Asn Leu Gly Ser Gly
                465                 470                 475                 480
Val Asn Arg Ala Ser Val Ser Ala Phe Ala Thr Thr Asn Arg Met Glu
            485                 490                 495
Leu Glu Gly Ala Ser Tyr Gln Val Pro Pro Gln Pro Asn Gly Met Thr
            500                 505                 510
Asn Asn Leu Gln Gly Ser Asn Thr Tyr Ala Leu Glu Asn Thr Met Ile
            515                 520                 525
```

```
Phe Asn Ser Gln Pro Ala Asn Pro Gly Thr Thr Ala Thr Tyr Leu Glu
    530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Val Ala Thr Asn Asn Gln Ser Ser
                565                 570                 575
Thr Thr Ala Pro Ala Thr Gly Thr Tyr Asn Leu Gln Glu Ile Val Pro
            580                 585                 590
Gly Ser Val Trp Met Glu Arg Asp Val Tyr Leu Gln Gly Pro Ile Trp
        595                 600                 605
Ala Lys Ile Pro Glu Thr Gly Ala His Phe His Pro Ser Pro Ala Met
    610                 615                 620
Gly Gly Phe Gly Leu Lys His Pro Pro Pro Met Met Leu Ile Lys Asn
625                 630                 635                 640
Thr Pro Val Pro Gly Asn Ile Thr Ser Phe Ser Asp Val Pro Val Ser
                645                 650                 655
Ser Phe Ile Thr Gln Tyr Ser Thr Gly Gln Val Thr Val Glu Met Glu
            660                 665                 670
Trp Glu Leu Lys Lys Glu Asn Ser Lys Arg Trp Asn Pro Glu Ile Gln
        675                 680                 685
Tyr Thr Asn Asn Tyr Asn Asp Pro Gln Phe Val Asp Phe Ala Pro Asp
    690                 695                 700
Ser Thr Gly Glu Tyr Arg Thr Thr Arg Pro Ile Gly Thr Arg Tyr Leu
705                 710                 715                 720
Thr Arg Pro Leu

<210> SEQ ID NO 15
<211> LENGTH: 2203
<212> TYPE: DNA
<213> ORGANISM: adeno-associated virus 5

<400> SEQUENCE: 15
tttattgagg gtatgcgaca tgaatgggtt aaaggggtcg ggtaaggtat cgggttccga      60
taggtctggt ggttctgtat tccccggtgc tgtccgggc aaagtccaca aactgggggt     120
cgttgtagtt gttttgtgtac tggatctctg ggttccacct cttggagttt tccttcttga    180
gctcccactc catctccacg gtgacctgcc cggtgctgta ctgggtgatg aagctgctga    240
cgggcacgtc cgagaagctg gtgatatttc cgggcacagg cgtgttcttg atgagcatca    300
tgggcggtgg gtgtttgagt ccgaatccgc ccatggccgg agaggggtga agtgcgccc     360
ccgtctctgg gatcttggcc cagatgggtc cttggaggta cacgtccctc tccatccaca    420
cgctgccggg cacgatttcc tggaggttgt acgtgccggt cgcggggggca gtggtggagc    480
tctggttgtt ggtggccacc tgcccgccga cgttgtacgc cacgcggttc accggctgcg    540
tctcgctctc gctggtgatg agcatgttgc cctcgaggta cgtggcggtg gtgcccgggt    600
tcgccggctg gctgttgaag atcatagtgt tctccagggc ataggtgttg ctgccctgga    660
ggttgttggt catgccgttc ggctgcgggg gcacctggta actcgcgccc tcgagctcca    720
tcctattggt cgtggcgaag gcgctgacac tggcgcggtt gaccccggag cccaggttcc    780
agccctgggt tcggcccatg ggccccggga accagttttt gtaggtgttg gcgtatctcc    840
cggccaggtt cttgttgaac tggactccgc cagtgttatt tgtgctcacg aagcggtaca    900
agtactggtc caccagcggg ttggccagct gaacaggtt ctgactggga gcgaagctgg     960
agtggaaggg cacctcctca aagttgtagg taaactcaaa gttgttgccc gttctcagca   1020
```

```
tcttgctggg aaagtactct aggcagaaga agctgctcct ctcgtgggga ttttctgtgt    1080
tgtcgcggtt cagcgtcgcg taaccgtact gcggcagcgt aaagacctgc ggagggaagg    1140
ccggcaggca tccctcggtc ccgttgccga cgacgtaggg cagctggtag tcgtcgtccg    1200
taaacacttg gacggtggag gtgaggttgt tggcgatggt ggtggtggag tcctgcaccg    1260
tgacctcttt gacttgaatg ttgaagattt tgactctgag gaccggggt ctgaagcccc     1320 agtagttgtt gatgagtctt tgccagtctc gggggctcca gtggctgtgg aagcggttaa    1380
agtcaaagta cccccagggg gtgctgtatc caaagtaggc gttggcgttg cttccgtcga    1440
cggagccgct tttgatctct cggtactggt ggttgttgta gctgggcagc acccaggttc    1500
gggtggactt ggtgacgact ctgtccccca tccacgtgga atcgcaatgc caatctcccg    1560
aggcattgcc cactccatcg gcaccttggt tattgtcgcc caatgggccg ccacctcccg    1620
cagacattgt atcagctccc aaacttgagg ctggttgggc tgggatttgc agctgctggg    1680
atccgctggg tccagcttcg gcgtctgacg aggtggaagg cttggagtcc tcttcggtcc    1740
gagccttctt tctttttgga aagtggtcgt ctatccgctt tccggtaggg gccgtcttag    1800
caccctcttc aaccaggcca aaaggttcga gaacccttt cttggcctga aagactgcct     1860
ttccgaggtt tcccccgaag gatgtgtcgt cggcgagctt ctcctgaaac tcggcgtccg    1920
cgtggttgta cttgaggtag ggggttgtctc ccgcctcaag ctgctcgttg tacgagatgt    1980
cgtgctctcg cgcgacctcg tctgccctgt tgacaggctc tcctcgatcg agaccgtttc    2040
cgggtccgag atagttataa ccaggcagca aagaccacg ggcttgatct tgatgctgct     2100
gattgggttt tggtttcggt gggcccgctt caaggcccaa aaactcgcga agaccttcac    2160
caacttcttc aaccaatct ggagggtgat caacaaaaga cat                       2203
```

<210> SEQ ID NO 16
<211> LENGTH: 2203
<212> TYPE: DNA
<213> ORGANISM: adeno-associated virus 5

<400> SEQUENCE: 16

```
atgtcttttg ttgatcaccc tccagattgg ttggaagaag ttggtgaagg tcttcgcgag     60 ttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga    180
ggagagcctg tcaacagggc agacgaggtc gcgcgagagc acgacatctc gtacaacgag    240
cagcttgagg cggagacaa cccctacctc aagtacaacc acgcggacgc cgagtttcag    300
gagaagctcg ccgacgacac atccttcggg ggaaacctcg gaaaggcagt ctttcaggcc    360
aagaaaaggg ttctcgaacc ttttggcctg gttgagaagg gtgctaagac ggcccctacc    420
ggaaagcgga tagacgacca cttttccaaaa agaaagaagg ctcggaccga agaggactcc    480
aagccttcca cctcgtcaga cgccgaagct ggacccagcg atcccagca gctgcaaatc     540 ccagcccaac cagcctcaag tttgggagct gatacaatgt ctgcgggagg tggcggccca    600
ttgggcgaca taaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag cacccccctgg ggctatttg actttaaccg cttccacagc    840
cactggagcc ccgagactg caaaagactc atcaacaact actggggctt cagaccccgg    900
```

```
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa cttttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgcccccgca gccgaacggc atgaccaaca acctccaggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cggtcaacct ccaggaaatc gtgcccggca gcgtgtggat ggagagggac   1800
gtgtacctcc aaggacccat ctgggccaag atcccagaga cggggcgcca ctttcaccccc   1860
tctccggcca tgggcggatt cggactcaaa caccccaccg ccatgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca acgaccccca gtttgtggac   2100
tttgccccgg acagcaccgg ggaatacaga accaccagac ctatcggaac ccgatacctt   2160
acccgacccc tttaacccat tcatgtcgca taccctcaat aaa                    2203

<210> SEQ ID NO 17
<211> LENGTH: 724
<212> TYPE: PRT
<213> ORGANISM: adeno-associated virus 5

<400> SEQUENCE: 17

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140
```

```
Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
```

```
                565                 570                 575
Thr Thr Ala Pro Ala Thr Gly Thr Val Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
            645                 650                 655

Ser Phe Ile Thr Gln Tyr Ser Thr Gly Gln Val Thr Val Glu Met Glu
        660                 665                 670

Trp Glu Leu Lys Lys Glu Asn Ser Lys Arg Trp Asn Pro Glu Ile Gln
    675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 18
<211> LENGTH: 2203
<212> TYPE: DNA
<213> ORGANISM: adeno-associated virus 5

<400> SEQUENCE: 18
tttattgagg gtatgcgaca tgaatgggtt aaaggggtcg ggtaaggtat cgggttccga        60
taggtctggt ggttctgtat tccccggtgc tgtccggggc aaagtccaca aactgggggt       120
cgttgtagtt gtttgtgtac tggatctctg ggttccacct cttggagttt tccttcttga       180
gctcccactc catctccacg gtgacctgcc cggtgctgta ctgggtgatg aagctgctga       240
cgggcacgtc cgagaagctg gtgatatttc cgggcacagg cgtgttcttg atgagcatca       300
tgggcggtgg gtgtttgagt ccgaatccgc ccatggccgg agaggggtga aagtgcgccc       360
ccgtctctgg gatcttggcc agatgggtc cttggaggta cacgtccctc tccatccaca       420
cgctgccggg cacgatttcc tggaggttga ccgtgccggt cgcgggggca gtggtggagc       480
tctggttgtt ggtggccatc tgcccgccga cgttgtacgc cacgcggttc accggctgcg       540
tctcgctctc gctggtgatg agcatgttgc cctcgaggta cgtggcggtg gtgcccgggt       600
tcgccggctg gctgttgaag atcatagtgt tctccagggc ataggtgttg ctgccctgga       660
ggttgttggt catgccgttc ggctgcgggg cacctggta actcgcgccc tcagctcca        720 tcctattggt cgtggcgaag gcgctgacac tggcgcggtt gaccccggag cccaggttcc       780
agccctgggt tcggcccatg ggccccggga accagttttt gtaggtgttg gcgtatctcc       840
cggccaggtt cttgttgaac tggactccgc cagtgttatt tgtgctcacg aagcggtaca       900
agtactggtc caccagcggg ttggccagct tgaacaggtt ctgactggga gcgaagctgg       960
agtggaaggg cacctcctca aagttgtagg taaactcaaa gttgttgccc gttctcagca      1020
tcttgctggg aaagtactct aggcagaaga agctgctcct ctcggtggga ttttctgtgt      1080
tgtcgcggtt cagcgtcgcg taaccgtact gcggcagcgt aaagacctgc ggagggaagg      1140
ccggcaggca tccctcggtc ccgttgccga cgacgtaggg cagctggtag tcgtcgtccg      1200
```

| | |
|---|---|
| taaacacttg gacggtggag gtgaggttgt tggcgatggt ggtggtggag tcctgcaccg | 1260 |
| tgacctcttt gacttgaatg ttgaagattt tgactctgag ggaccggggt ctgaagcccc | 1320 |
| agtagttgtt gatgagtctt tgccagtctc gggggctcca gtggctgtgg aagcggttaa | 1380 |
| agtcaaagta ccccccaggg gtgctgtatc caaagtaggc gttggcgttg cttccgtcga | 1440 |
| cggagccgct tttgatctct cggtactggt ggttgttgta gctgggcagc acccaggttc | 1500 |
| gggtggactt ggtgacgact ctgtccccca tccacgtgga atcgcaatgc caatctcccg | 1560 |
| aggcattgcc cactccatcg gcaccttggt tattgtcgcc caatgggccg ccacctcccg | 1620 |
| cagacattgt atcagctccc aaacttgagg ctggttgggc tgggatttgc agctgctggg | 1680 |
| atccgctggg tccagcttcg gcgtctgacg aggtggaagg cttggagtcc tcttcggtcc | 1740 |
| gagccttctt tcttttttgga aagtggtcgt ctatccgctt tccggtaggg gccgtcttag | 1800 |
| caccctcttc aaccaggcca aaaggttcga gaacccttt cttggcctga aagactgcct | 1860 |
| ttccgaggtt tcccccgaag gatgtgtcgt cggcgagctt ctcctgaaac tcggcgtccg | 1920 |
| cgtggttgta cttgaggtag gggttgtctc ccgcctcaag ctgctcgttg tacgagatgt | 1980 |
| cgtgctctcg cgcgacctcg tctgccctgt tgacaggctc tcctcgatcg agaccgtttc | 2040 |
| cgggtccgag atagttataa ccaggcagca caagaccacg ggcttgatct tgatgctgct | 2100 |
| gattgggttt tggtttcggt gggcccgctt caaggcccaa aaactcgcga agaccttcac | 2160 |
| caacttcttc caaccaatct ggagggtgat caacaaaaga cat | 2203 |

<210> SEQ ID NO 19
<211> LENGTH: 2203
<212> TYPE: DNA
<213> ORGANISM: adeno-associated virus 5

<400> SEQUENCE: 19

| | |
|---|---|
| atgtcttttg ttgatcaccc tccagattgg ttggaagaag ttggtgaagg tcttcgcgag | 60 |
| tttttgggcc ttgaagcggg cccaccgaaa ccaaaaccca atcagcagca tcaagatcaa | 120 |
| gcccgtggtc ttgtgctgcc tggttataac tatctcggac ccggaaacgg tctcgatcga | 180 |
| ggagagcctg tcaacagggc agacgaggtc gcgcgagagc acgacatctc gtacaacgag | 240 |
| cagcttgagg cgggagacaa ccccctacctc aagtacaacc acgcggacgc cgagtttcag | 300 |
| gagaagctcg ccgacgacac atccttcggg ggaaacctcg gaaaggcagt ctttcaggcc | 360 |
| aagaaaaggg ttctcgaacc ttttggcctg gttgagagg gtgctaagac ggcccctacc | 420 |
| ggaaagcgga tagacgacca cttttccaaaa agaaagaagg ctcggaccga agaggactcc | 480 |
| aagccttcca cctcgtcaga cgccgaagct ggacccagcg gatcccagca gctgcaaatc | 540 |
| ccagcccaac cagcctcaag tttgggagct gatacaatgt ctgcgggagg tggcggccca | 600 |
| ttgggcgaca ataaccaagg tgccgatgga gtgggcaatg cctcgggaga ttggcattgc | 660 |
| gattccacgt ggatggggga cagagtcgtc accaagtcca cccgaacctg ggtgctgccc | 720 |
| agctacaaca accaccagta ccgagagatc aaaagcggct ccgtcgacgg aagcaacgcc | 780 |
| aacgcctact ttggatacag cacccctgg gggtactttg actttaaccg cttccacagc | 840 |
| cactggagcc cccgagactg gcaaagactc atcaacaact actggggctt cagacccgg | 900 |
| tccctcagag tcaaaatctt caacattcaa gtcaaagagg tcacggtgca ggactccacc | 960 |
| accaccatcg ccaacaacct cacctccacc gtccaagtgt ttacggacga cgactaccag | 1020 |
| ctgccctacg tcgtcggcaa cgggaccgag ggatgcctgc cggccttccc tccgcaggtc | 1080 |
| tttacgctgc cgcagtacgg ttacgcgacg ctgaaccgcg acaacacaga aaatcccacc | 1140 |

```
gagaggagca gcttcttctg cctagagtac tttcccagca agatgctgag aacgggcaac   1200
aactttgagt ttacctacaa ctttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg ctggaacct  gggctccggg   1440 gtcaaccgcg ccagtgtcag cgccttcgcc acgaccaata ggatggagct cgagggcgcg   1500
agttaccagg tgccccgca gccgaacggc atgaccaaca acctccaggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacac ccaggaaatc gtgcccggca gcgtgtggat ggagagggac   1800
gtgtacctcc aaggacccat ctgggccaag atcccagaga cggggggcgca ctttcacccc   1860 tctccggcca tgggcggatt cggactcaaa cacccaccgc ccatgatgct catcaagaac   1920
acgcctgtgc ccgaaatat  caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca acgaccccca gtttgtggac   2100
tttgccccgg acagcaccgg ggaatacaga accaccagac ctatcggaac ccgataccct   2160
acccgacccc tttaacccat tcatgtcgca taccctcaat aaa                      2203

<210> SEQ ID NO 20
<211> LENGTH: 724
<212> TYPE: PRT
<213> ORGANISM: adeno-associated virus 5

<400> SEQUENCE: 20

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
```

```
                180             185             190
Met Ser Ala Gly Gly Gly Pro Leu Gly Asp Asn Gln Gly Ala
            195             200             205
Asp Gly Val Gly Asn Ala Ser Gly Asp Trp His Cys Asp Ser Thr Trp
    210             215             220
Met Gly Asp Arg Val Val Thr Lys Ser Thr Arg Thr Trp Val Leu Pro
225             230             235             240
Ser Tyr Asn Asn His Gln Tyr Arg Glu Ile Lys Ser Gly Ser Val Asp
            245             250             255
Gly Ser Asn Ala Asn Ala Tyr Phe Gly Tyr Ser Thr Pro Trp Gly Tyr
            260             265             270
Phe Asp Phe Asn Arg Phe His Ser His Trp Ser Pro Arg Asp Trp Gln
        275             280             285
Arg Leu Ile Asn Asn Tyr Trp Gly Phe Arg Pro Arg Ser Leu Arg Val
        290             295             300
Lys Ile Phe Asn Ile Gln Val Lys Glu Val Thr Val Gln Asp Ser Thr
305             310             315             320
Thr Thr Ile Ala Asn Asn Leu Thr Ser Thr Val Gln Val Phe Thr Asp
            325             330             335
Asp Asp Tyr Gln Leu Pro Tyr Val Val Gly Asn Gly Thr Glu Gly Cys
            340             345             350
Leu Pro Ala Phe Pro Pro Gln Val Phe Thr Leu Pro Gln Tyr Gly Tyr
            355             360             365
Ala Thr Leu Asn Arg Asp Asn Thr Glu Asn Pro Thr Glu Arg Ser Ser
            370             375             380
Phe Phe Cys Leu Glu Tyr Phe Pro Ser Lys Met Leu Arg Thr Gly Asn
385             390             395             400
Asn Phe Glu Phe Thr Tyr Asn Phe Glu Glu Val Pro Phe His Ser Ser
            405             410             415
Phe Ala Pro Ser Gln Asn Leu Phe Lys Leu Ala Asn Pro Leu Val Asp
            420             425             430
Gln Tyr Leu Tyr Arg Phe Val Ser Thr Asn Asn Thr Gly Gly Val Gln
            435             440             445
Phe Asn Lys Asn Leu Ala Gly Arg Tyr Ala Asn Thr Tyr Lys Asn Trp
            450             455             460
Phe Pro Gly Pro Met Gly Arg Thr Gln Gly Trp Asn Leu Gly Ser Gly
465             470             475             480
Val Asn Arg Ala Ser Val Ser Ala Phe Ala Thr Thr Asn Arg Met Glu
            485             490             495
Leu Glu Gly Ala Ser Tyr Gln Val Pro Pro Gln Pro Asn Gly Met Thr
            500             505             510
Asn Asn Leu Gln Gly Ser Asn Thr Tyr Ala Leu Glu Asn Thr Met Ile
            515             520             525
Phe Asn Ser Gln Pro Ala Asn Pro Gly Thr Thr Ala Thr Tyr Leu Glu
            530             535             540
Gly Asn Met Leu Ile Thr Ser Glu Ser Glu Thr Gln Pro Val Asn Arg
545             550             555             560
Val Ala Tyr Asn Val Gly Gly Gln Met Ala Thr Asn Asn Gln Ser Ser
            565             570             575
Thr Thr Ala Pro Ala Thr Gly Thr Tyr Asn Thr Gln Glu Ile Val Pro
            580             585             590
Gly Ser Val Trp Met Glu Arg Asp Val Tyr Leu Gln Gly Pro Ile Trp
            595             600             605
```

```
Ala Lys Ile Pro Glu Thr Gly Ala His Phe His Pro Ser Pro Ala Met
        610                 615                 620
Gly Gly Phe Gly Leu Lys His Pro Pro Met Met Leu Ile Lys Asn
625                 630                 635                 640
Thr Pro Val Pro Gly Asn Ile Thr Ser Phe Ser Asp Val Pro Val Ser
            645                 650                 655
Ser Phe Ile Thr Gln Tyr Ser Thr Gly Gln Val Thr Val Glu Met Glu
            660                 665                 670
Trp Glu Leu Lys Lys Glu Asn Ser Lys Arg Trp Asn Pro Glu Ile Gln
        675                 680                 685
Tyr Thr Asn Asn Tyr Asn Asp Pro Gln Phe Val Asp Phe Ala Pro Asp
        690                 695                 700
Ser Thr Gly Glu Tyr Arg Thr Thr Arg Pro Ile Gly Thr Arg Tyr Leu
705                 710                 715                 720

Thr Arg Pro Leu
```

<210> SEQ ID NO 21
<211> LENGTH: 2203
<212> TYPE: DNA
<213> ORGANISM: adeno-associated virus 5

<400> SEQUENCE: 21

```
tttattgagg gtatgcgaca tgaatgggtt aaaggggtcg ggtaaggtat cgggttccga      60
taggtctggt ggttctgtat tccccggtgc tgtccggggc aaagtccaca aactgggggt     120
cgttgtagtt gtttgtgtac tggatctctg ggttccacct cttggagttt tccttcttga    180
gctcccactc catctccacg gtgacctgcc cggtgctgta ctgggtgatg aagctgctga    240
cgggcacgtc cgagaagctg gtgatatttc cgggcacagg cgtgttcttg atgagcatca    300
tgggcggtgg gtgtttgagt ccgaatccgc ccatggccgg agaggggtga agtgcgccc     360
ccgtctctgg gatcttggcc cagatgggtc cttggaggta cacgtccctc tccatccaca    420
cgctgccggg cacgatttcc tgggtgttgt acgtgccggt cgcgggggca gtggtggagc    480
tctggttgtt ggtggccatc tgcccgccga cgttgtacgc cacgcggttc accggctgcg    540
tctcgctctc gctggtgatg agcatgttgc cctcgaggta cgtggcggtg gtgcccgggt    600
tcgccggctg gctgttgaag atcatagtgt tctccagggc ataggtgttg ctgccctgga    660
ggttgttggt catgccgttc ggctgcgggg gcacctggta actcgcgccc tcgagctcca    720
tcctattggt cgtggcgaag gcgctgacac tggcgcggtt gaccccggag cccaggttcc    780
agccctgggt tcggcccatg ggccccggga accagttttt gtaggtgttg gcgtatctcc    840
cggccaggtt cttgttgaac tggactccgc cagtgttatt tgtgctcacg aagcggtaca    900
agtactggtc caccagcggg ttggccagct gaacaggtt ctgactggga gcgaagctgg     960
agtggaaggg cacctcctca agttgtagg taaactcaaa gttgttgccc gttctcagca    1020
tcttgctggg aaagtactct aggcagaaga agctgctcct ctcggtggga ttttctgtgt    1080
tgtcgcggtt cagcgtcgcg taaccgtact gcggcagcgt aaagacctgc ggagggaagg    1140
ccggcaggca tccctcggtc ccgttgccga cgacgtaggg cagctggtag tcgtcgtccg    1200
taaacacttg gacggtggag gtgaggttgt tggcgatggt ggtggtggag tcctgcaccg    1260
tgacctcttt gacttgaatg ttgaagattt tgactctgag gaccggggt ctgaagcccc     1320
agtagttgtt gatgagtctt tgccagtctc ggggctcca gtggctgtgg aagcggttaa     1380
agtcaaagta cccccagggg gtgctgtatc caaagtaggc gttggcgttg cttccgtcga    1440
```

```
cggagccgct tttgatctct cggtactggt ggttgttgta gctgggcagc acccaggttc    1500
gggtggactt ggtgacgact ctgtccccca tccacgtgga atcgcaatgc caatctcccg    1560
aggcattgcc cactccatcg gcaccttggt tattgtcgcc caatgggccg ccacctcccg    1620
cagacattgt atcagctccc aaacttgagg ctggttgggc tgggatttgc agctgctggg    1680
atccgctggg tccagcttcg gcgtctgacg aggtggaagg cttggagtcc tcttcggtcc    1740
gagccttctt tcttttttgga aagtggtcgt ctatccgctt ccggtaggg gccgtcttag    1800 caccctcttc aaccaggcca aaaggttcga gaaccctttt cttggcctga aagactgcct    1860
ttccgaggtt tcccccgaag gatgtgtcgt cggcgagctt ctcctgaaac tcggcgtccg    1920
cgtggttgta cttgaggtag gggttgtctc ccgcctcaag ctgctcgttg tacgagatgt    1980
cgtgctctcg cgcgacctcg tctgccctgt tgacaggctc tcctcgatcg agaccgtttc    2040
cgggtccgag atagttataa ccaggcagca aagaccacg ggcttgatct tgatgctgct    2100
gattgggttt tggtttcggt gggcccgctt caaggcccaa aaactcgcga agaccttcac    2160
caacttcttc aaccaatct ggagggtgat caacaaaaga cat                      2203

<210> SEQ ID NO 22
<211> LENGTH: 2203
<212> TYPE: DNA
<213> ORGANISM: adeno-associated virus 5

<400> SEQUENCE: 22
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc ttttggcctg gttgaagagg gtgctaagac ggcccctacc     420
ggaaagcgga tagacgacca cttttccaaaa agaaagaagg ctcggaccga agaggactcc     480
aagccttcca cctcgtcaga cgccgaagct ggacccagcg atcccagca gctgcaaatc     540 ccagcccaac cagcctcaag tttggagct gatacaatgt ctgcgggagg tggcggccca     600
ttgggcgaca taaccaagg tgccgatgga gtgggcaatg cctcgggaga ttggcattgc     660
gattccacgt ggatggggga cagagtcgtc accaagtcca cccgaacctg ggtgctgccc     720
agctacaaca accaccagta ccgagagatc aaaagcggct ccgtcgacgg aagcaacgcc     780
aacgcctact ttggatacag caccccctgg gggtactttg actttaaccg cttccacagc     840
cactggagcc cccgagactg gcaaagactc atcaacaact actgggggctt cagaccccgg     900 tccctcagag tcaaaatctt caacattcaa gtcaaagagg tcacggtgca ggactccacc     960
accaccatcg ccaacaacct cacctccacc gtccaagtgt ttacggacga cgactaccag    1020
ctgccctacg tcgtcggcaa cgggaccgag ggatgcctgc cggccttccc tccgcaggtc    1080
tttacgctgc cgcagtacgg ttacgcgacg ctgaaccgcg acaacacaga aaatccaccc    1140
gagaggagca gcttcttctg cctagagtac tttcccagca agatgctgag aacgggcaac    1200
aactttgagt ttacctacaa ctttgaggag gtgcccttcc actccagctt cgctcccagt    1260
cagaacctgt tcaagctggc caaccgctg gtggaccagt acttgtaccg cttcgtgagc    1320
```

```
acaaataaca ctggcggagt ccagttcaac aagaacctgg ccgggagata cgccaacacc    1380
tacaaaaact ggttcccggg gcccatgggc cgaacccagg gctggaacct gggctccggg    1440
gtcaaccgcg ccagtgtcag cgccttcgcc acgaccaata ggatggagct cgagggcgcg    1500
agttaccagg tgcccccgca gccgaacggc atgaccaaca acctccaggg cagcaacacc    1560
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cggtcaacac ccaggaaatc gtgcccggca cgtgtggat ggagagggac     1800 gtgtacctcc aaggacccat ctgggccaag atcccagaga cggggcgca ctttcacccc     1860 tctccggcca tgggcggatt cggactcaaa cacccaccgc ccatgatgct catcaagaac    1920
acgcctgtgc ccggaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca acgaccccca gtttgtggac    2100
tttgccccgg acagcaccgg ggaatacaga accaccagac ctatcggaac ccgataccTT    2160
acccgacccc tttaacccat tcatgtcgca taccctcaat aaa                      2203
```

<210> SEQ ID NO 23
<211> LENGTH: 724
<212> TYPE: PRT
<213> ORGANISM: adeno-associated virus 5

<400> SEQUENCE: 23

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220
```

```
Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Val Asn Thr Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640
```

```
Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 24
<211> LENGTH: 2203
<212> TYPE: DNA
<213> ORGANISM: adeno-associated virus 5

<400> SEQUENCE: 24
```

| | | | | | |
|---|---|---|---|---|---|
| tttattgagg | gtatgcgaca | tgaatgggtt | aaaggggtcg | ggtaaggtat | cgggttccga | 60 |
| taggtctggt | ggttctgtat | tccccggtgc | tgtccgggc | aaagtccaca | aactgggggt | 120 |
| cgttgtagtt | gtttgtgtac | tggatctctg | ggttccacct | cttggagttt | tccttcttga | 180 |
| gctcccactc | catctccacg | gtgacctgcc | cggtgctgta | ctgggtgatg | aagctgctga | 240 |
| cgggcacgtc | cgagaagctg | gtgatatttc | cgggcacagg | cgtgttcttg | atgagcatca | 300 |
| tgggcggtgg | gtgtttgagt | ccgaatccgc | ccatggccgg | agaggggtga | agtgcgccc | 360 |
| ccgtctctgg | gatcttggcc | cagatgggtc | cttggaggta | cacgtccctc | tccatccaca | 420 |
| cgctgccggg | cacgatttcc | tgggtgttga | ccgtgccggt | cgcggggca | gtggtggagc | 480 |
| tctggttgtt | ggtggccatc | tgcccgccga | cgttgtacgc | cacgcggttc | accggctgcg | 540 |
| tctcgctctc | gctggtgatg | agcatgttgc | cctcgaggta | cgtggcggtg | gtgcccgggt | 600 |
| tcgccggctg | gctgttgaag | atcatagtgt | ctccagggc | ataggtgttg | ctgccctgga | 660 |
| ggttgttggt | catgccgttc | ggctgcgggg | gcacctggta | actcgcgccc | tcgagctcca | 720 |
| tcctattggt | cgtggcgaag | gcgctgacac | tggcgcggtt | gaccccggag | cccaggttcc | 780 |
| agccctgggt | tcggcccatg | ggccccggga | ccagtttttt | gtaggtgttg | gcgtatctcc | 840 |
| cggccaggtt | cttgttgaac | tggactccgc | cagtgttatt | tgtgctcacg | aagcggtaca | 900 |
| agtactggtc | caccagcggg | ttggccagct | tgaacaggtt | ctgactggga | gcgaagctgg | 960 |
| agtggaaggg | cacctcctca | aagttgtagg | taaactcaaa | gttgttgccc | gttctcagca | 1020 |
| tcttgctggg | aaagtactct | aggcagaaga | agctgctcct | ctcggtggga | ttttctgtgt | 1080 |
| tgtcgcggtt | cagcgtcgcg | taaccgtact | gcggcagcgt | aaagacctgc | ggagggaagg | 1140 |
| ccggcaggca | tccctcggtc | ccgttgccga | cgacgtaggg | cagctggtag | tcgtcgtccg | 1200 |
| taaacacttg | gacggtggag | gtgaggttgt | tggcgatggt | ggtggtggag | tcctgcaccg | 1260 |
| tgacctcttt | gacttgaatg | ttgaagattt | tgactctgag | ggaccggggt | ctgaagcccc | 1320 |
| agtagttgtt | gatgagtctt | tgccagtctc | gggggctcca | gtggctgtgg | aagcggttaa | 1380 |
| agtcaaagta | cccccagggg | gtgctgtatc | caaagtaggc | gttggcgttg | cttccgtcga | 1440 |
| cggagccgct | tttgatctct | cggtactggt | ggttgttgta | gctgggcagc | acccaggttc | 1500 |
| gggtggactt | ggtgacgact | ctgtccccca | tccacgtgga | atcgcaatgc | caatctcccg | 1560 |
| aggcattgcc | cactccatcg | gcaccttggt | tattgtcgcc | caatgggccg | ccacctcccg | 1620 |

-continued

| | |
|---|---|
| cagacattgt atcagctccc aaacttgagg ctggttgggc tgggatttgc agctgctggg | 1680 |
| atccgctggg tccagcttcg gcgtctgacg aggtggaagg cttggagtcc tcttcggtcc | 1740 |
| gagccttctt tcttttttgga aagtggtcgt ctatccgctt tccggtaggg gccgtcttag | 1800 |
| caccctcttc aaccaggcca aaaggttcga gaaccctttt cttggcctga aagactgcct | 1860 |
| ttccgaggtt tccccgaag gatgtgtcgt cggcgagctt ctcctgaaac tcggcgtccg | 1920 |
| cgtggttgta cttgaggtag ggttgtctc ccgcctcaag ctgctcgttg tacgagatgt | 1980 |
| cgtgctctcg cgcgacctcg tctgccctgt tgacaggctc tcctcgatcg agaccgtttc | 2040 |
| cgggtccgag atagttataa ccaggcagca aagaccacg ggcttgatct tgatgctgct | 2100 |
| gattgggttt tggtttcggt gggcccgctt caaggcccaa aaactcgcga agaccttcac | 2160 |
| caacttcttc aaccaatct ggagggtgat caacaaaaga cat | 2203 |

<210> SEQ ID NO 25
<211> LENGTH: 2203
<212> TYPE: DNA
<213> ORGANISM: adeno-associated virus 5

<400> SEQUENCE: 25

| | |
|---|---|
| atgtcttttg ttgatcaccc tccagattgg ttggaagaag ttggtgaagg tcttcgcgag | 60 |
| ttttttgggcc ttgaagcggg cccaccgaaa ccaaaaccca atcagcagca tcaagatcaa | 120 |
| gcccgtggtc ttgtgctgcc tggttataac tatctcggac ccggaaacgg tctcgatcga | 180 |
| ggagagcctg tcaacagggc agacgaggtc gcgcgagagc acgacatctc gtacaacgag | 240 |
| cagcttgagg cgggagacaa ccctacctc aagtacaacc acgcggacgc cgagtttcag | 300 |
| gagaagctcg ccgacgacac atccttcggg ggaaacctcg gaaaggcagt cttttcaggcc | 360 |
| aagaaaaggg ttctcgaacc ttttggcctg gttgagagg gtgctaagac ggccccctacc | 420 |
| ggaaagcgga tagacgacca cttttccaaaa agaaagaagg ctcggaccga agaggactcc | 480 |
| aagccttcca cctcgtcaga cgccgaagct ggacccagcg atccagca gctgcaaatc | 540 |
| ccagcccaac cagcctcaag tttgggagct gatacaatgt ctgcgggagg tggcggccca | 600 |
| ttgggcgaca taaccaagg tgccgatgga gtgggcaatg cctcgggaga ttggcattgc | 660 |
| gattccacgt ggatggggga cagagtcgtc accaagtcca cccgaacctg ggtgctgccc | 720 |
| agctacaaca accaccagta ccgagagatc aaaagcggct ccgtcgacgg aagcaacgcc | 780 |
| aacgcctact ttggatacag cacccccctgg gggtactttg actttaaccg cttccacagc | 840 |
| cactggagcc cccgagactg gcaaagactc atcaacaact actggggctt cagaccccgg | 900 |
| tccctcagag tcaaaatctt caacattcaa gtcaaagagg tcacggtgca ggactccacc | 960 |
| accaccatcg ccaacaacct cacctccacc gtccaagtgt ttacggacga cgactaccag | 1020 |
| ctgccctacg tcgtcggcaa cgggaccgag ggatgcctgc cggccttccc tccgcaggtc | 1080 |
| tttacgctgc cgcagtacgg ttacgcgacg ctgaaccgcg acaacacaga aaatcccacc | 1140 |
| gagaggagca gcttcttctg cctagagtac tttcccagca gatgctgag aacgggcaac | 1200 |
| aactttgagt ttacctacaa ctttgaggag gtgcccttcc actccagctt cgctcccagt | 1260 |
| cagaaccctgt tcaagctggc caacccgctg gtggaccagt acttgtaccg cttcgtgagc | 1320 |
| acaaataaca ctggcggagt ccagttcaac aagaacctgg ccgggagata cgccaacacc | 1380 |
| tacaaaaact ggttccccggg gcccatgggc cgaacccagg gctggaacct gggctccggg | 1440 |
| gtcaaccgcg ccagtgtcag cgccttcgcc acgaccaata ggatggagct cgagggcgcg | 1500 |
| agttaccagg tgccccgca gccgaacggc atgaccaaca acctccaggg cagcaacacc | 1560 |

-continued

```
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca gcgtgtggat ggagagggac    1800
gtgtacctcc aaggacccat ctgggccaag atcccagaga cggggggcgca ctttcacccc    1860 tctccggcca tgggcggatt cggactcaaa cacccaccgc ccatgatgct catcaagaac    1920
acgcctgtgc ccggaaatat caccagcttc tcggccgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca acgaccccca gtttgtggac    2100
tttgccccgg acagcaccgg ggaatacaga accaccagac ctatcggaac ccgatacctt    2160
acccgacccc tttaacccat tcatgtcgca taccctcaat aaa                     2203
```

<210> SEQ ID NO 26
<211> LENGTH: 724
<212> TYPE: PRT
<213> ORGANISM: adeno-associated virus 5

<400> SEQUENCE: 26

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255
```

```
Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Ala Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
```

```
                675              680             685
Tyr Thr Asn Asn Tyr Asn Asp Pro Gln Phe Val Asp Phe Ala Pro Asp
    690              695             700
Ser Thr Gly Glu Tyr Arg Thr Thr Arg Pro Ile Gly Thr Arg Tyr Leu
705             710             715             720
Thr Arg Pro Leu

<210> SEQ ID NO 27
<211> LENGTH: 2203
<212> TYPE: DNA
<213> ORGANISM: adeno-associated virus 5

<400> SEQUENCE: 27
tttattgagg gtatgcgaca tgaatgggtt aaaggggtcg ggtaaggtat cgggttccga      60
taggtctggt ggttctgtat tccccggtgc tgtccggggc aaagtccaca aactgggggt     120
cgttgtagtt gtttgtgtac tggatctctg ggttccacct cttggagttt tccttcttga     180
gctcccactc catctccacg gtgacctgcc cggtgctgta ctgggtgatg aagctgctga     240
cgggcacggc cgagaagctg gtgatatttc cgggcacagg cgtgttcttg atgagcatca     300
tgggcggtgg gtgtttgagt ccgaatccgc ccatggccgg agaggggtga agtgcgccc      360 ccgtctctgg gatcttggcc cagatgggtc cttggaggta cacgtccctc tccatccaca     420
cgctgccggg cacgatttcc tggaggttgt acgtgccggt cgcgggggca gtggtggagc     480
tctggttgtt ggtggccatc tgcccgccga cgttgtacgc cacgcggttc accggctgcg     540
tctcgctctc gctggtgatg agcatgttgc cctcgaggta cgtggcggtg gtgcccgggt     600 cgccggctg gctgttgaag atcatagtgt tctccagggc ataggtgttg ctgccctgga     660
ggttgttggt catgccgttc ggctgcgggg cacctggta actcgcgccc tcgagctcca     720
tcctattggt cgtggcgaag gcgctgacac tggcgcggtt gaccccggag cccaggttcc     780
agccctgggt tcggcccatg ggccccggga accagttttt gtaggtgttg gcgtatctcc     840
cggccaggtt cttgttgaac tggactccgc cagtgttatt tgtgctcacg aagcggtaca     900
agtactggtc caccagcggg ttggccagct tgaacaggtt ctgactggga gcgaagctgg     960
agtggaaggg cacctcctca aagttgtagg taaactcaaa gttgttgccc gttctcagca    1020
tcttgctggg aaagtactct aggcagaaga agctgctcct ctcggtggga ttttctgtgt    1080
tgtcgcggtt cagcgtcgcg taaccgtact gcggcagcgt aaagacctgc ggagggaagg    1140
ccggcaggca tccctcggtc ccgttgccga cgacgtaggg cagctggtag tcgtcgtccg    1200
taaacacttg gacggtggag gtgaggttgt tggcgatggt ggtggtggag tcctgcaccg    1260
tgacctcttt gacttgaatg ttgaagattt tgactctgag ggaccggggt ctgaagcccc    1320
agtagttgtt gatgagtctt tgccagtctc gggggctcca gtgctgtgg aagcggttaa     1380 agtcaaagta cccccagggg gtgctgtatc caaagtaggc gttggcgttg cttccgtcga    1440
cggagccgct tttgatctct cggtactggt ggttgttgta gctgggcagc acccaggttc    1500
gggtggactt ggtgacgact ctgtccccca tccacgtgga atcgcaatgc caatctcccg    1560
aggcattgcc cactccatcg gcaccttggt tattgtcgcc caatgggccg ccacctcccg    1620
cagacattgt atcagctccc aaacttgagg ctggttgggc tgggatttgc agctgctggg    1680
atccgctggg tccagcttcg gcgtctgacg aggtggaagg cttggagtcc tcttcggtcc    1740
gagccttctt tcttttttgga aagtggtcgt ctatccgctt tccggtaggg gccgtcttag    1800
caccctcttc aaccaggcca aaaggttcga gaaccctttt cttggcctga aagactgcct    1860
```

```
ttccgaggtt tcccccgaag gatgtgtcgt cggcgagctt ctcctgaaac tcggcgtccg    1920
cgtggttgta cttgaggtag gggttgtctc ccgcctcaag ctgctcgttg tacgagatgt    1980
cgtgctctcg cgcgacctcg tctgccctgt tgacaggctc tcctcgatcg agaccgtttc    2040
cgggtccgag atagttataa ccaggcagca caagaccacg ggcttgatct tgatgctgct    2100
gattgggttt tggtttcggt gggcccgctt caaggcccaa aaactcgcga agaccttcac    2160
caacttcttc caaccaatct ggagggtgat caacaaaaga cat                      2203
```

<210> SEQ ID NO 28
<211> LENGTH: 2203
<212> TYPE: DNA
<213> ORGANISM: adeno-associated virus 5

<400> SEQUENCE: 28

```
atgtcttttg ttgatcaccc tccagattgg ttggaagaag ttggtgaagg tcttcgcgag     60
tttttgggcc ttgaagcggg cccaccgaaa ccaaaaccca atcagcagca tcaagatcaa    120
gcccgtggtc ttgtgctgcc tggttataac tatctcggac ccggaaacgg tctcgatcga    180
ggagagcctg tcaacagggc agacgaggtc gcgcgagagc acgacatctc gtacaacgag    240
cagcttgagg cggagacaa ccctacctc aagtacaacc acgcggacgc cgagtttcag      300
gagaagctcg ccgacgacac atccttcggg gaaaacctcg aaaggcagt ctttcaggcc    360 aagaaaaggg ttctcgaacc ttttggcctg gttgagagg gtgctaagac ggcccctacc    420
ggaaagcgga tagacgacca cttttccaaaa agaaagaagg ctcggaccga agaggactcc    480
aagccttcca cctcgtcaga cgccgaagct ggacccagcg atcccagca gctgcaaatc    540 ccagcccaac cagcctcaag tttgggagct gatacaatgt ctgcgggagg tggcggccca    600 tgggcgaca ataaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag cacccctctgg gggtactttg actttaaccg cttccacagc    840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttatggacga cgactaccag   1020 ctgcccta cgtcgtcggcaa cgggaccgag ggatgcctgc cggccttccc tccgcaggtc   1080
tttacgctgc cgcagtacgg ttacgcgacg ctgaaccgcg acaacacaga aaatccacc    1140 gagaggagca gcttcttctg cctagagtac tttcccagca agatgctgag aacgggcaac   1200
aactttgagt ttacctacaa cttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg    1440
gtcaaccgcg ccagtgtcag cgccttcgcc acgaccaata ggatggagct cgagggcgcg   1500
agttaccagg tgcccccgca gccgaacggc atgaccaaca cctccagggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
```

-continued

```
gcgaccggca cgtacaacct ccaggaaatc gtgcccggca gcgtgtggat ggagagggac    1800
gtgtacctcc aaggacccat ctgggccaag atcccagaga cggggggcgca ctttcacccc    1860 tctccggcca tgggcggatt cggactcaaa cacccaccgc ccatgatgct catcaagaac    1920
acgcctgtgc ccgaaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca acgaccccca gtttgtggac    2100
tttgccccgg acagcaccgg ggaatacaga accaccagac ctatcggaac ccgatacctt    2160
acccgacccc tttaacccat tcatgtcgca taccctcaat aaa                      2203
```

<210> SEQ ID NO 29
<211> LENGTH: 724
<212> TYPE: PRT
<213> ORGANISM: adeno-associated virus 5

<400> SEQUENCE: 29

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
```

```
                290             295             300
Lys Ile Phe Asn Ile Gln Val Lys Glu Val Thr Val Gln Asp Ser Thr
305                 310             315                 320

Thr Thr Ile Ala Asn Asn Leu Thr Ser Thr Val Gln Val Phe Met Asp
                325             330             335

Asp Asp Tyr Gln Leu Pro Tyr Val Val Gly Asn Gly Thr Glu Gly Cys
            340             345             350

Leu Pro Ala Phe Pro Pro Gln Val Phe Thr Leu Pro Gln Tyr Gly Tyr
            355             360             365

Ala Thr Leu Asn Arg Asp Asn Thr Glu Asn Pro Thr Glu Arg Ser Ser
            370             375             380

Phe Phe Cys Leu Glu Tyr Phe Pro Ser Lys Met Leu Arg Thr Gly Asn
385                 390             395                 400

Asn Phe Glu Phe Thr Tyr Asn Phe Glu Glu Val Pro Phe His Ser Ser
                405             410             415

Phe Ala Pro Ser Gln Asn Leu Phe Lys Leu Ala Asn Pro Leu Val Asp
            420             425             430

Gln Tyr Leu Tyr Arg Phe Val Ser Thr Asn Asn Thr Gly Gly Val Gln
            435             440             445

Phe Asn Lys Asn Leu Ala Gly Arg Tyr Ala Asn Thr Tyr Lys Asn Trp
450                 455             460

Phe Pro Gly Pro Met Gly Arg Thr Gln Gly Trp Asn Leu Gly Ser Gly
465                 470             475                 480

Val Asn Arg Ala Ser Val Ser Ala Phe Ala Thr Thr Asn Arg Met Glu
                485             490             495

Leu Glu Gly Ala Ser Tyr Gln Val Pro Pro Gln Pro Asn Gly Met Thr
            500             505             510

Asn Asn Leu Gln Gly Ser Asn Thr Tyr Ala Leu Glu Asn Thr Met Ile
            515             520             525

Phe Asn Ser Gln Pro Ala Asn Pro Gly Thr Thr Ala Thr Tyr Leu Glu
            530             535             540

Gly Asn Met Leu Ile Thr Ser Glu Ser Glu Thr Gln Pro Val Asn Arg
545                 550             555                 560

Val Ala Tyr Asn Val Gly Gly Gln Met Ala Thr Asn Asn Gln Ser Ser
                565             570             575

Thr Thr Ala Pro Ala Thr Gly Thr Tyr Asn Leu Gln Glu Ile Val Pro
            580             585             590

Gly Ser Val Trp Met Glu Arg Asp Val Tyr Leu Gln Gly Pro Ile Trp
            595             600             605

Ala Lys Ile Pro Glu Thr Gly Ala His Phe His Pro Ser Pro Ala Met
610                 615             620

Gly Gly Phe Gly Leu Lys His Pro Pro Pro Met Met Leu Ile Lys Asn
625                 630             635                 640

Thr Pro Val Pro Gly Asn Ile Thr Ser Phe Ser Asp Val Pro Val Ser
                645             650             655

Ser Phe Ile Thr Gln Tyr Ser Thr Gly Gln Val Thr Val Glu Met Glu
            660             665             670

Trp Glu Leu Lys Lys Glu Asn Ser Lys Arg Trp Asn Pro Glu Ile Gln
            675             680             685

Tyr Thr Asn Asn Tyr Asn Asp Pro Gln Phe Val Asp Phe Ala Pro Asp
            690             695             700

Ser Thr Gly Glu Tyr Arg Thr Thr Arg Pro Ile Gly Thr Arg Tyr Leu
705                 710             715                 720
```

Thr Arg Pro Leu

<210> SEQ ID NO 30
<211> LENGTH: 2203
<212> TYPE: DNA
<213> ORGANISM: adeno-associated virus 5

<400> SEQUENCE: 30

| | |
|---|---|
| tttattgagg gtatgcgaca tgaatgggtt aaaggggtcg ggtaaggtat cgggttccga | 60 |
| taggtctggt ggttctgtat tccccggtgc tgtccggggc aaagtccaca aactgggggt | 120 |
| cgttgtagtt gtttgtgtac tggatctctg ggttccacct cttggagttt tccttcttga | 180 |
| gctcccactc catctccacg gtgacctgcc cggtgctgta ctgggtgatg aagctgctga | 240 |
| cgggcacgtc cgagaagctg gtgatatttc cgggcacagg cgtgttcttg atgagcatca | 300 |
| tgggcggtgg gtgtttgagt ccgaatccgc ccatggccgg agaggggtga agtgcgccc | 360 |
| ccgtctctgg gatcttggcc cagatgggtc cttggaggta cacgtccctc tccatccaca | 420 |
| cgctgccggg cacgatttcc tggaggttgt acgtgccggt cgcggggca gtggtggagc | 480 |
| tctggttgtt ggtggccatc tgcccgccga cgttgtacgc cacgcggttc accggctgcg | 540 |
| tctcgctctc gctggtgatg agcatgttgc cctcgaggta cgtggcggtg gtgcccgggt | 600 |
| tcgccggctg gctgttgaag atcatagtgt tctccagggc ataggtgttg ctgccctgga | 660 |
| ggttgttggt catgccgttc ggctgcgggg gcacctggta actcgcgccc tcgagctcca | 720 |
| tcctattggt cgtggcgaag gcgctgacac tggcgcggtt gaccccggag cccaggttcc | 780 |
| agccctgggt tcggcccatg ggccccggga accagttttt gtaggtgttg gcgtatctcc | 840 |
| cggccaggtt cttgttgaac tggactccgc cagtgttatt tgtgctcacg aagcggtaca | 900 |
| agtactggtc caccagcggg ttggccagct tgaacaggtt ctgactggga gcgaagctgg | 960 |
| agtggaaggg cacctcctca agttgtagg taaactcaaa gttgttgccc gttctcagca | 1020 |
| tcttgctggg aaagtactct aggcagaaga agctgctcct ctcggtggga ttttctgtgt | 1080 |
| tgtcgcggtt cagcgtcgcg taaccgtact gcggcagcgt aaagacctgc ggagggaagg | 1140 |
| ccggcaggca tccctcggtc ccgttgccga cgacgtaggg cagctggtag tcgtcgtcca | 1200 |
| taaacacttg gacggtggag gtgaggttgt tggcgatggt ggtggtggag tcctgcaccg | 1260 |
| tgacctcttt gacttgaatg ttgaagattt tgactctgag ggaccggggt ctgaagcccc | 1320 |
| agtagttgtt gatgagtctt tgccagtctc gggggctcca gtggctgtgg aagcggttaa | 1380 |
| agtcaaagta cccccagggg gtgctgtatc caaagtaggc gttggcgttg cttccgtcga | 1440 |
| cggagccgct tttgatctct cggtactggt ggttgttgta gctgggcagc acccaggttc | 1500 |
| gggtggactt ggtgacgact ctgtccccca tccacgtgga atcgcaatgc caatctcccg | 1560 |
| aggcattgcc cactccatcg gcaccttggt tattgtcgcc caatgggccg ccacctcccg | 1620 |
| cagacattgt atcagctccc aaacttgagg ctggttgggc tgggatttgc agctgctggg | 1680 |
| atccgctggg tccagcttcg gcgtctgacg aggtggaagg cttggagtcc tcttcggtcc | 1740 |
| gagccttctt tcttttttgga aagtggtcgt ctatccgctt tccggtaggg gccgtcttag | 1800 |
| caccctcttc aaccaggcca aaaggttcga gaaccctttt cttggcctga agactgcct | 1860 |
| ttccgaggtt tcccccgaag gatgtgtcgt cggcgagctt ctcctgaaac tcggcgtccg | 1920 |
| cgtggttgta cttgaggtag gggttgtctc ccgcctcaag ctgctcgttg tacgagatgt | 1980 |
| cgtgctctcg cgcgacctcg tctgccctgt tgacaggctc tcctcgatcg agaccgtttc | 2040 |

```
cgggtccgag atagttataa ccaggcagca caagaccacg ggcttgatct tgatgctgct    2100
gattgggttt tggtttcggt gggcccgctt caaggcccaa aaactcgcga agaccttcac    2160
caacttcttc caaccaatct ggagggtgat caacaaaaga cat                      2203

<210> SEQ ID NO 31
<211> LENGTH: 2203
<212> TYPE: DNA
<213> ORGANISM: adeno-associated virus 5

<400> SEQUENCE: 31
atgtcttttg ttgatcaccc tccagattgg ttggaagaag ttggtgaagg tcttcgcgag      60 ttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc ttttggcctg gttgaagagg gtgctaagac ggcccctacc     420
ggaaagcgga tagacgacca cttttccaaaa agaaagaagg ctcggaccga agaggactcc     480
aagccttcca cctcgtcaga cgccgaagct ggacccagcg atcccagca gctgcaaatc     540 ccagcccaac cagcctcaag tttgggagct gatacaatgt ctgcgggagg tggcggccca     600
ttgggcgaca ataaccaagg tgccgatgga gtgggcaatg cctcgggaga ttggcattgc     660
gattccacgt ggatggggga cagagtcgtc accaagtcca cccgaacctg ggtgctgccc     720
agctacaaca accaccagta ccgagagatc aaaagcggct ccgtcgacgg aagcaacgcc     780
aacgcctact ttgatacag caccccctgg gggtactttg actttaaccg cttccacagc     840
cactggagcc cccgagactg gcaaagactc atcaacaact actggggctt cagaccccgg     900
tccctcagag tcaaaatctt caacattcaa gtcaaagagg tcacggtgca ggactccacc     960
accaccatcg ccaacaacct cacctccacc gtcgatgtgt ttacggacga cgactaccag    1020 ctgcccktacg tcgtcggcaa cgggaccgag ggatgcctgc cggccttccc tccgcaggtc    1080
tttacgctgc cgcagtacgg ttacgcgacg ctgaaccgcg acaacacaga aaatcccacc    1140
gagaggagca gcttcttctg cctagagtac tttcccagca agatgctgag aacgggcaac    1200
aactttgagt ttacctacaa cttgaggag gtgcccttcc actccagctt cgctcccagt    1260
cagaacctgt tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttcccggg gcccatgggc cgaacccagg ctggaacct gggctccggg    1440 gtcaaccgcg ccagtgtcag cgccttcgcc acgaccaata ggatggagct cgagggcgcg    1500
agttaccagg tgccccgca gccgaacggc atgaccaaca acctccaggg cagcaacacc    1560
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca cgtcgcggcg gcagatggcc accaacaacc agagctccac cactgccccc    1740
gcgaccggca cgtacaacct ccaggaaatc gtgcccggca cgtgtggat ggagagggac    1800 gtgtacctcc aaggacccat ctgggccaag atcccagaga cggggcgca ctttcacccc    1860 tctccggcca tggcggatt cggactcaaa cacccaccgc catgatgctct catcaagaac    1920 acgcctgtgc ccggaaatat caccagcttc tcggacgtgc ccgtcagcag cttcatcacc    1980
```

```
cagtacagca ccgggcaggt caccgtggag atggagtggg agctcaagaa ggaaaactcc   2040
aagaggtgga acccagagat ccagtacaca aacaactaca cgaccccca gtttgtggac    2100 tttgccccgg acagcaccgg ggaatacaga accaccagac ctatcggaac ccgatacctt   2160
acccgacccc tttaacccat tcatgtcgca taccctcaat aaa                    2203
```

<210> SEQ ID NO 32
<211> LENGTH: 724
<212> TYPE: PRT
<213> ORGANISM: adeno-associated virus 5

<400> SEQUENCE: 32

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Asp Val Phe Thr Asp
                325                 330                 335
```

```
Asp Asp Tyr Gln Leu Pro Tyr Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
            405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
            450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
            485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
            530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
            565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
            610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
            645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 33
<211> LENGTH: 2203
<212> TYPE: DNA
```

<213> ORGANISM: adeno-associated virus 5

<400> SEQUENCE: 33

```
tttattgagg gtatgcgaca tgaatgggtt aaaggggtcg ggtaaggtat cgggttccga       60
taggtctggt ggttctgtat tccccggtgc tgtccggggc aaagtccaca aactgggggt      120
cgttgtagtt gtttgtgtac tggatctctg ggttccacct cttggagttt tccttcttga      180
gctcccactc catctccacg gtgacctgcc cggtgctgta ctgggtgatg aagctgctga      240
cgggcacgtc cgagaagctg gtgatatttc cgggcacagg cgtgttcttg atgagcatca      300
tgggcggtgg gtgtttgagt ccgaatccgc ccatggccgg agaggggtga agtgcgccc       360
ccgtctctgg gatcttggcc cagatgggtc cttggaggta cacgtccctc tccatccaca      420
cgctgccggg cacgatttcc tggaggttgt acgtgccggt cgcggggggca gtggtggagc     480
tctggttgtt ggtggccatc tgcccgccga cgttgtacgc cacgcggttc accggctgcg      540
tctcgctctc gctggtgatg agcatgttgc cctcgaggta cgtggcggtg gtgcccgggt      600
tcgccggctg gctgttgaag atcatagtgt ctccagggc ataggtgttg ctgccctgga       660
ggttgttggt catgccgttc ggctgcgggg gcacctggta actcgcgccc tcgagctcca      720
tcctattggt cgtggcgaag cgctgacac tggcgcggtt gaccccggag cccaggttcc       780
agccctgggt tcggcccatg gccccggga accagttttt gtaggtgttg gcgtatctcc       840
cggccaggtt cttgttgaac tggactccgc cagtgttatt tgtgctcacg aagcggtaca      900
agtactggtc caccagcggg ttggccagct tgaacaggtt ctgactggga gcgaagctgg      960
agtggaaggg cacctcctca agttgtagg taaactcaaa gttgttgccc gttctcagca     1020
tcttgctggg aaagtactct aggcagaaga agctgctcct ctcggtggga ttttctgtgt     1080
tgtcgcggtt cagcgtcgcg taaccgtact gcggcagcgt aaagacctgc ggagggaagg     1140
ccggcaggca tccctcggtc ccgttgccga cgacgtaggg cagctggtag tcgtcgtccg     1200
taaacacatc gacggtggag gtgaggttgt tggcgatggt ggtggtggag tcctgcaccg     1260
tgacctcttt gacttgaatg ttgaagattt tgactctgag ggaccggggt ctgaagcccc     1320
agtagttgtt gatgagtctt tgccagtctc ggggctcca gtggctgtgg aagcggttaa      1380
agtcaaagta cccccagggg gtgctgtatc caaagtaggc gttggcgttg cttccgtcga     1440
cggagccgct tttgatctct cggtactggt ggttgttgta gctgggcagc acccaggttc     1500
gggtggactt ggtgacgact ctgtccccca tccacgtgga atcgcaatgc caatctcccg     1560
aggcattgcc cactccatcg gcaccttggt tattgtcgcc caatgggccg ccacctcccg     1620
cagacattgt atcagctccc aaacttgagg ctggttgggc tgggatttgc agctgctggg     1680
atccgctggg tccagcttcg gcgtctgacg aggtggaagg cttggagtcc tcttcggtcc     1740
gagccttctt tcttttttgga aagtggtcgt ctatccgctt tccggtaggg gccgtcttag     1800
caccctcttc aaccaggcca aaaggttcga gaaccctttt cttggcctga aagactgcct     1860
ttccgaggtt tcccccgaag gatgtgtcgt cggcgagctt ctcctgaaac tcggcgtccg     1920
cgtggttgta cttgaggtag gggttgtctc ccgcctcaag ctgctcgttg tacgagatgt     1980
cgtgctctcg cgcgacctcg tctgcccgtgt tgacaggctc tcctcgatcg agaccgtttc     2040
cgggtccgag atagttataa ccaggcagca aagaccacg ggcttgatct tgatgctgct      2100
gattgggttt tggtttcggt gggcccgctt caaggcccaa aaactcgcga agaccttcac     2160
caacttcttc caaccaatct ggagggtgat caacaaaaga cat                       2203
```

<210> SEQ ID NO 34
<211> LENGTH: 2203
<212> TYPE: DNA
<213> ORGANISM: adeno-associated virus 5

<400> SEQUENCE: 34

| | |
|---|---|
| atgtcttttg ttgatcaccc tccagattgg ttggaagaag ttggtgaagg tcttcgcgag | 60 |
| tttttgggcc ttgaagcggg cccaccgaaa ccaaaaccca atcagcagca tcaagatcaa | 120 |
| gcccgtggtc ttgtgctgcc tggttataac tatctcggac ccggaaacgg tctcgatcga | 180 |
| ggagagcctg tcaacagggc agacgaggtc gcgcgagagc acgacatctc gtacaacgag | 240 |
| cagcttgagg cgggagacaa ccctacctc aagtacaacc acgcggacgc cgagtttcag | 300 |
| gagaagctcg ccgacgacac atccttcggg ggaaacctcg gaaaggcagt ctttcaggcc | 360 |
| aagaaaaggg ttctcgaacc ttttggcctg gttgagagg gtgctaagac ggcccctacc | 420 |
| ggaaagcgga tagacgacca ctttccaaaa agaaagaagg ctcggaccga agaggactcc | 480 |
| aagccttcca cctcgtcaga cgccgaagct ggacccagcg atcccagca gctgcaaatc | 540 |
| ccagcccaac cagcctcaag tttgggagct gatacaatgt ctgcgggagg tggcggccca | 600 |
| ttgggcgaca taaccaagg tgccgatgga gtgggcaatg cctcgggaga ttggcattgc | 660 |
| gattccacgt ggatggggga cagagtcgtc accaagtcca cccgaacctg ggtgctgccc | 720 |
| agctacaaca accaccagta ccgagagatc aaaagcggct ccgtcgacgg aagcaacgcc | 780 |
| aacgcctact ttggatacag cacccctgg gggtactttg actttaaccg cttccacagc | 840 |
| cactggagcc cccgagactg gcaaagactc atcaacaact actggggctt cagaccccgg | 900 |
| tccctcagag tcaaaatctt caacattcaa gtcaagagg tcacggtgca ggactccacc | 960 |
| accaccatcg ccaacaacct cacctccacc gtccaagtgt ttacggacga cgactaccag | 1020 |
| ctgccctacg tcgtcggcaa cgggaccag ggatgcctgc cggccttccc tccgcaggtc | 1080 |
| tttacgctgc cgcagtacgg ttacgcgacg ctgaaccgcg acaacacaga aaatcccacc | 1140 |
| gagaggagca gcttcttctg cctagagtac tttcccagca gatgctgag aacgggcaac | 1200 |
| aactttgagt ttacctacaa ctttgaggag gtgcccttcc actccagctt cgctcccagt | 1260 |
| cagaacctgt tcaagctggc caacccgctg gtggaccagt acttgtaccg cttcgtgagc | 1320 |
| acaaataaca ctggcggagt ccagttcaac aagaacctgg ccgggagata cgccaacacc | 1380 |
| tacaaaaact ggttcccggg gcccatgggc cgaacccagg gctggaacct gggctccggg | 1440 |
| gtcaaccgcg ccagtgtcag cgccttcgcc acgaccaata ggatggagct cgagggcgcg | 1500 |
| agttaccagg tgccccgca gccgaacggc atgaccaaca cctccagggc agcaacacc | 1560 |
| tatgccctgg agaacactat gatcttcaac agccagccgg cgaacccggg caccaccgcc | 1620 |
| acgtacctcg agggcaacat gctcatcacc agcgagagcg agacgcagcc ggtgaaccgc | 1680 |
| gtggcgtaca acgtcggcgg gcagatggcc accaacaacc agagctccac cactgccccc | 1740 |
| gcgaccggca cgtacaacct ccaggaaatc gtgcccggca gcgtgtggat ggagagggac | 1800 |
| gtgtacctcc aaggacccat ctgggccaag atcccagaga cggggcgca ctttcacccc | 1860 |
| tctccggca tgggcggatt cggactcaaa cacccaccgc ccatgatgct catcaagaac | 1920 |
| acgcctgtgc ccggaaatat caccagcttc tcggacgtgc ccgtcagcag cttcatcacc | 1980 |
| cagtacagca ccgggcaggt caccgtggag atggagtggg agctcaagaa ggaaaactcc | 2040 |
| aagaggtgga acccagagat ccagtacaca aacaactaca acgaccccca gtttgtggac | 2100 |
| tttgcccccg acagcaccgg ggaatacaga accaccgac ctatcggaac ccgataccctt | 2160 |

```
acccgacccc tttaacccat tcatgtcgca taccctcaat aaa                    2203
```

<210> SEQ ID NO 35
<211> LENGTH: 724
<212> TYPE: PRT
<213> ORGANISM: adeno-associated virus 5

<400> SEQUENCE: 35

| | | | | | | | | | | | | | | |
|---|---|---|---|---|---|---|---|---|---|---|---|---|---|---|
| Met | Ser | Phe | Val | Asp | His | Pro | Pro | Asp | Trp | Leu | Glu | Glu | Val | Gly |
| 1 | | | | 5 | | | | | 10 | | | | | 15 |
| Glu Gly | Leu | Arg | Glu | Phe | Leu | Gly | Leu | Glu | Ala | Gly | Pro | Pro | Lys | Pro | Lys |
| | | 20 | | | | | 25 | | | | | 30 | | |

(table-like; reproducing as listed)

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65              70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Gln Gly Cys
            340                 345                 350

Leu Pro Ala Phe Pro Pro Gln Val Phe Thr Leu Pro Gln Tyr Gly Tyr
        355                 360                 365

| | | | | | | | | | | | | |
|---|---|---|---|---|---|---|---|---|---|---|---|---|
| Ala | Thr | Leu | Asn | Arg | Asp | Asn | Thr | Glu | Asn | Pro | Thr | Glu | Arg | Ser | Ser |
| | 370 | | | | 375 | | | | 380 | | | |

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 36
<211> LENGTH: 2203
<212> TYPE: DNA
<213> ORGANISM: adeno-associated virus 5

<400> SEQUENCE: 36
tttattgagg gtatgcgaca tgaatgggtt aaaggggtcg ggtaaggtat cgggttccga     60
taggtctggt ggttctgtat tccccggtgc tgtccggggc aaagtccaca aactgggggt    120

```
cgttgtagtt gtttgtgtac tggatctctg ggttccacct cttggagttt tccttcttga    180
gctcccactc catctccacg gtgacctgcc cggtgctgta ctgggtgatg aagctgctga    240
cgggcacgtc cgagaagctg gtgatatttc cgggcacagg cgtgttcttg atgagcatca    300
tgggcggtgg gtgtttgagt ccgaatccgc ccatggccgg agaggggtga agtgcgccc     360
ccgtctctgg gatcttggcc cagatgggtc cttggaggta cacgtccctc tccatccaca    420
cgctgccggg cacgatttcc tggaggttgt acgtgccggt cgcgggggca gtggtggagc    480
tctggttgtt ggtggccatc tgcccgccga cgttgtacgc cacgcggttc accggctgcg    540
tctcgctctc gctggtgatg agcatgttgc cctcgaggta cgtggcggtg gtgcccgggt    600
tcgccggctg gctgttgaag atcatagtgt tctccagggc ataggtgttg ctgccctgga    660
ggttgttggt catgccgttc ggctgcgggg gcacctggta actcgcgccc tcgagctcca    720
tcctattggt cgtggcgaag gcgctgacac tggcgcggtt gaccccggag cccaggttcc    780
agccctgggt tcggcccatg ggccccggga accagttttt gtaggtgttg gcgtatctcc    840
cggccaggtt cttgttgaac tggactccgc cagtgttatt tgtgctcacg aagcggtaca    900
agtactggtc caccagcggg ttggccagct gaacaggttg ctgactggga gcgaagctgg    960
agtggaaggg cacctcctca aagttgtagg taaactcaaa gttgttgccc gttctcagca   1020
tcttgctggg aaagtactct aggcagaaga agctgctcct ctcggtggga ttttctgtgt   1080
tgtcgcggtt cagcgtcgcg taaccgtact gcggcagcgt aaagacctgc ggagggaagg   1140
ccggcaggca tccctgggtc ccgttgccga cgacgtaggg cagctggtag tcgtcgtccg   1200
taaacacttg gacggtggag gtgaggttgt tggcgatggt ggtggtggag tcctgcaccg   1260
tgacctcttt gacttgaatg ttgaagattt tgactctgag ggaccggggt ctgaagcccc   1320
agtagttgtt gatgagtctt tgccagtctc gggggctcca gtggctgtgg aagcggttaa   1380
agtcaaagta cccccagggg gtgctgtatc caaagtaggc gttggcgttg cttccgtcga   1440
cggagccgct tttgatctct cggtactggt ggttgttgta gctgggcagc acccaggttc   1500
gggtggactt ggtgacgact ctgtccccca tccacgtgga atcgcaatgc caatctcccg   1560
aggcattgcc cactccatcg gcaccttggt tattgtcgcc caatgggccg ccactctccg   1620
cagacattgt atcagctccc aaacttgagg ctggttgggc tgggatttgc agctgctggg   1680
atccgctggg tccagcttcg gcgtctgacg aggtggaagg cttggagtcc tcttcggtcc   1740
gagccttctt tcttttttgga aagtggtcgt ctatccgctt tccggtaggg gccgtcttag   1800
caccctcttc aaccaggcca aaaggttcga gaacccttttt cttggcctga agactgcct   1860
ttccgaggtt tccccccgaag gatgtgtcgt cggcgagctt ctcctgaaac tcggcgtccg   1920
cgtggttgta cttgaggtag gggttgtctc ccgcctcaag ctgctcgttg tacgagatgt   1980
cgtgctctcg cgcgaccteg tctgccctgt tgacaggctc tcctcgatcg agaccgtttc   2040
cgggtccgag atagttataa ccaggcagca caagaccacg ggcttgatct tgatgctgct   2100
gattgggttt tggtttcggt gggcccgctt caaggcccaa aaactcgcga agaccttcac   2160
caacttcttc caaccaatct ggagggtgat caacaaaaga cat                     2203
```

<210> SEQ ID NO 37
<211> LENGTH: 2203
<212> TYPE: DNA
<213> ORGANISM: adeno-associated virus 5

<400> SEQUENCE: 37

```
atgtcttttg ttgatcaccc tccagattgg ttggaagaag ttggtgaagg tcttcgcgag    60
tttttgggcc ttgaagcggg cccaccgaaa ccaaaaccca atcagcagca tcaagatcaa   120
gcccgtggtc ttgtgctgcc tggttataac tatctcggac ccggaaacgg tctcgatcga   180
ggagagcctg tcaacagggc agacgaggtc gcgcgagagc acgacatctc gtacaacgag   240
cagcttgagg cgggagacaa ccccctacctc aagtacaacc acgcggacgc cgagtttcag   300
gagaagctcg ccgacgacac atccttcggg ggaaacctcg gaaaggcagt ctttcaggcc   360
aagaaaaggg ttctcgaacc ttttggcctg gttgaagagg gtgctaagac ggcccctacc   420
ggaaagcgga tagacgacca ctttccaaaa agaaagaagg ctcggaccga agaggactcc   480
aagccttcca cctcgtcaga cgccgaagct ggacccagcg atcccagca gctgcaaatc   540
ccagcccaac cagcctcaag tttgggagct gatacaatgt ctgcgggagg tggcggccca   600
ttgggcgaca ataaccaagg tgccgatgga gtgggcaatg cctcgggaga ttggcattgc   660
gattccacgt ggatggggga cagagtcgtc accaagtcca cccgaacctg ggtgctgccc   720
agctacaaca accaccagta ccgagagatc aaaagcggct ccgtcgacgg aagcaacgcc   780
aacgcctact ttggatacag cacccccctgg gggtactttg actttaaccg cttccacagc   840
cactggagcc cccgagactg gcaaagactc atcaacaact actggggctt cagacccccgg   900
tccctcagag tcaaaatctt caacattcaa gtcaaagagg tcacggtgca ggactccacc   960
accaccatcg ccaacaacct cacctccacc gtccaagtgt ttacgacga cgactaccag  1020
ctgccctacg tcgtcggcaa cgggaccgag ggatgcctgc cggccttccc tccgcaggtc  1080
tttacgctgc cgcagtacgg ttacgcgacg ctgaaccgcg acaacacaga aaatcccacc  1140
gagaggagca gcttcttctg cctagagtac tttcccagca agatgctgag aacgggcaac  1200
aactttgagt ttacctacaa ctttgaggag gtgcccttcc actccagctt cgctcccagt  1260
cagaacctgt tcaagctggc caacccgctg gtggaccagt acttgtaccg cttcgtgagc  1320
acaaataaca ctggcggagt ccagttcaac aagaacctgg ccgggagata cgccaacacc  1380
tacaaaaact ggttcccggg gcccatgggc cgaacccagg gctggaacct gggctccggg  1440
gtcaaccgcg ccagtgtcag cgccttcgcc acgaccaata ggatggagct cgagggcgcg  1500
agttaccagg tgcccccgca gccgaacggc atgaccaaca cctccagggg cagcaacacc  1560
tatgccctgg agaacactat gatcttcaac agccagtcgg cgaacccggg caccaccgcc  1620
acgtacctcg agggcaacat gctcatcacc agcgagagcg agacgcagcc ggtgaaccgc  1680
gtggcgtaca cgtcggcgg gcagatggcc accaacaacc agagctccac cactgccccc  1740
gcgaccggca cgtacaacct ccaggaaatc gtgcccggca gcgtgtggat ggagagggac  1800
gtgtacctcc aaggacccat ctgggccaag atcccagaga cggggggcgca ctttcacccc  1860
tctccggcca tgggcggatt cggactcaaa cacccaccgc ccatgatgct catcaagaac  1920
acgcctgtgc ccggaaatat caccagcttc tcggacgtgc ccgtcagcag cttcatcacc  1980
cagtacagca ccgggcaggt caccgtggag atggagtggg agctcaagaa ggaaaactcc  2040
aagaggtgga acccagagat ccagtacaca aacaactaca acgacccca gtttgtggac  2100
tttgccccgg acagcaccgg ggaatacaga accaccagac ctatcggaac ccgataccttt  2160
acccgacccc tttaacccat tcatgtcgca taccctcaat aaa                    2203
```

<210> SEQ ID NO 38
<211> LENGTH: 724
<212> TYPE: PRT
<213> ORGANISM: adeno-associated virus 5

<400> SEQUENCE: 38

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
```

Phe Ala Pro Ser Gln Asn Leu Phe Lys Leu Ala Asn Pro Leu Val Asp
            405                 410                 415

Gln Tyr Leu Tyr Arg Phe Val Ser Thr Asn Asn Thr Gly Gly Val Gln
    420                 425                 430

Phe Asn Lys Asn Leu Ala Gly Arg Tyr Ala Asn Thr Tyr Lys Asn Trp
435                 440                 445

Phe Pro Gly Pro Met Gly Arg Thr Gln Gly Trp Asn Leu Gly Ser Gly
450                 455                 460

Val Asn Arg Ala Ser Val Ser Ala Phe Ala Thr Thr Asn Arg Met Glu
465                 470                 475                 480

Leu Glu Gly Ala Ser Tyr Gln Val Pro Pro Gln Pro Asn Gly Met Thr
        485                 490                 495

Asn Asn Leu Gln Gly Ser Asn Thr Tyr Ala Leu Glu Asn Thr Met Ile
            500                 505                 510

Phe Asn Ser Gln Ser Ala Asn Pro Gly Thr Thr Ala Thr Tyr Leu Glu
                515                 520                 525

Gly Asn Met Leu Ile Thr Ser Glu Ser Glu Thr Gln Pro Val Asn Arg
                    530                 535                 540

Val Ala Tyr Asn Val Gly Gly Gln Met Ala Thr Asn Asn Gln Ser Ser
545                 550                 555                 560

Thr Thr Ala Pro Ala Thr Gly Thr Tyr Asn Leu Gln Glu Ile Val Pro
        565                 570                 575

Gly Ser Val Trp Met Glu Arg Asp Val Tyr Leu Gln Gly Pro Ile Trp
            580                 585                 590

Ala Lys Ile Pro Glu Thr Gly Ala His Phe His Pro Ser Pro Ala Met
                595                 600                 605

Gly Gly Phe Gly Leu Lys His Pro Pro Pro Met Met Leu Ile Lys Asn
                    610                 615                 620

Thr Pro Val Pro Gly Asn Ile Thr Ser Phe Ser Asp Val Pro Val Ser
625                 630                 635                 640

Ser Phe Ile Thr Gln Tyr Ser Thr Gly Gln Val Thr Val Glu Met Glu
        645                 650                 655

Trp Glu Leu Lys Lys Glu Asn Ser Lys Arg Trp Asn Pro Glu Ile Gln
            660                 665                 670

Tyr Thr Asn Asn Tyr Asn Asp Pro Gln Phe Val Asp Phe Ala Pro Asp
                675                 680                 685

Ser Thr Gly Glu Tyr Arg Thr Thr Arg Pro Ile Gly Thr Arg Tyr Leu
                    690                 695                 700

Thr Arg Pro Leu
705                 710                 715                 720

<210> SEQ ID NO 39
<211> LENGTH: 2203
<212> TYPE: DNA
<213> ORGANISM: adeno-associated virus 5

<400> SEQUENCE: 39
tttattgagg gtatgcgaca tgaatgggtt aaaggggtcg ggtaaggtat cgggttccga      60
taggtctggt ggttctgtat tccccggtgc tgtccggggc aaagtccaca aactgggggt     120
cgttgtagtt gtttgtgtac tggatctctg gttccacct cttggagttt tccttcttga     180
gctcccactc catctccacg gtgacctgcc cggtgctgta ctgggtgatg aagctgctga     240
cgggcacgtc cgagaagctg gtgatatttc cgggcacagg cgtgttcttg atgagcatca     300

```
tgggcggtgg gtgtttgagt ccgaatccgc ccatggccgg agaggggtga aagtgcgccc    360
ccgtctctgg gatcttggcc cagatgggtc cttggaggta cacgtccctc tccatccaca    420
cgctgccggg cacgatttcc tggaggttgt acgtgccggt cgcgggggca gtggtggagc    480
tctggttgtt ggtggccatc tgcccgccga cgttgtacgc cacgcggttc accggctgcg    540
tctcgctctc gctggtgatg agcatgttgc cctcgaggta cgtggcggtg gtgcccgggt    600
tcgccgactg gctgttgaag atcatagtgt tctccagggc ataggtgttg ctgccctgga    660
ggttgttggt catgccgttc ggctgcgggg gcacctggta actcgcgccc tcgagctcca    720
tcctattggt cgtggcgaag gcgctgacac tggcgcggtt gaccccggag cccaggttcc    780
agccctgggt tcggcccatg ggccccggga accagttttt gtaggtgttg gcgtatctcc    840
cggccaggtt cttgttgaac tggactccgc cagtgttatt tgtgctcacg aagcggtaca    900
agtactggtc caccagcggg ttggccagct tgaacaggtt ctgactggga gcgaagctgg    960
agtggaaggg cacctcctca aagttgtagg taaactcaaa gttgttgccc gttctcagca   1020
tcttgctggg aaagtactct aggcagaaga agctgctcct ctcggtggga ttttctgtgt   1080
tgtcgcggtt cagcgtcgcg taaccgtact gcggcagcgt aaagacctgc ggagggaagg   1140
ccggcaggca tccctcggtc ccgttgccga cgacgtaggg cagctggtag tcgtcgtccg   1200
taaacacttg gacggtggag gtgaggttgt tggcgatggt ggtggtggag tcctgcaccg   1260
tgacctcttt gacttgaatg ttgaagattt tgactctgag ggaccggggt ctgaagcccc   1320
agtagttgtt gatgagtctt tgccagtctc ggggctcca gtggctgtgg aagcggttaa   1380
agtcaaagta cccccagggg gtgctgtatc caaagtaggc gttggcgttg cttccgtcga   1440
cggagccgct tttgatctct cggtactggt ggttgttgta gctgggcagc acccaggttc   1500
gggtggactt ggtgacgact ctgtccccca tccacgtgga atcgcaatgc caatctcccg   1560
aggcattgcc cactccatcg gcaccttggt tattgtcgcc caatgggccg ccacctcccg   1620
cagacattgt atcagctccc aaacttgagg ctggttgggc tgggatttgc agctgctggg   1680
atccgctggg tccagcttcg gcgtctgacg aggtggaagg cttggagtcc tcttcggtcc   1740
gagccttctt tcttttttgga aagtggtcgt ctatccgctt tccggtaggg gccgtcttag   1800
caccctcttc aaccaggcca aaaggttcga gaacccttttt cttggcctga aagactgcct   1860
ttccgaggtt tcccccgaag gatgtgtcgt cggcgagctt ctcctgaaac tcggcgtccg   1920
cgtggttgta cttgaggtag gggttgtctc ccgcctcaag ctgctcgttg tacgagatgt   1980
cgtgctctcg cgcgacctcg tctgccctgt tgacaggctc tcctcgatcg agaccgtttc   2040
cgggtccgag atagttataa ccaggcagca caagaccacg ggcttgatct tgatgctgct   2100
gattgggttt tggtttcggt gggcccgctt caaggcccaa aaactcgcga agaccttcac   2160
caacttcttc caaccaatct ggagggtgat caacaaaaga cat                     2203
```

<210> SEQ ID NO 40
<211> LENGTH: 2203
<212> TYPE: DNA
<213> ORGANISM: adeno-associated virus 5

<400> SEQUENCE: 40

```
atgtcttttg ttgatcaccc tccagattgg ttggaagaag ttggtgaagg tcttcgcgag     60 ttttttgggcc ttgaagcggg cccaccgaaa ccaaaaccca atcagcagca tcaagatcaa    120
gcccgtggtc ttgtgctgcc tggttataac tatctcggac ccggaaacgg tctcgatcga    180
ggagagcctg tcaacagggc agacgaggtc gcgcgagagc acgacatctc gtacaacgag    240
```

```
cagcttgagg cgggagacaa cccctacctc aagtacaacc acgcggacgc cgagtttcag    300
gagaagctcg ccgacgacac atccttcggg ggaaacctcg aaaggcagt ctttcaggcc    360 aagaaaaggg ttctcgaacc ttttggcctg gttgaagagg gtgctaagac ggcccctacc    420
ggaaagcgga tagacgacca cttttccaaaa agaaagaagg ctcggaccga agaggactcc    480
aagccttcca cctcgtcaga cgccgaagct ggacccagcg gatcccagca gctgcaaatc    540
ccagcccaac cagcctcaag tttgggagct gatacaatgt ctgcgggagg tggcggccca    600
ttgggcgaca taaccaagg tgccgatgga gtgggcaatg cctcgggaga ttggcattgc    660
gattccacgt ggatggggga cagagtcgtc accaagtcca cccgaacctg ggtgctgccc    720
agctacaaca ccaccagta ccgagagatc aaaagcggct ccgtcgacgg aagcaacgcc    780
aacgcctact ttggatacag cacccctgg gggtactttg actttaaccg cttccacagc    840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa cttttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgcccccgca gccgaacggc atgaccaaca acctccaggg cagcaacacc   1560
tatgccctgg agaacactat gatcttcaac agccaggggg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cggggggcgca ctttcacccc   1860 tctccggcca tgggcggatt cggactcaaa cacccaccgc ccatgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca acgaccccca gtttgtggac   2100
tttgccccgg acagcaccgg ggaatacaga accaccagac ctatcggaac ccgatacctt   2160
acccgacccc tttaacccat tcatgtcgca taccctcaat aaa                     2203
```

<210> SEQ ID NO 41
<211> LENGTH: 724
<212> TYPE: PRT
<213> ORGANISM: adeno-associated virus 5

<400> SEQUENCE: 41

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys

-continued

```
                20                  25                  30
Pro Asn Gln Gln His Gln Asp Gln Ala Arg Gly Leu Val Leu Pro Gly
            35                  40                  45
Tyr Asn Tyr Leu Gly Pro Gly Asn Gly Leu Asp Arg Gly Glu Pro Val
        50                  55                  60
Asn Arg Ala Asp Glu Val Ala Arg Glu His Asp Ile Ser Tyr Asn Glu
65                  70                  75                  80
Gln Leu Glu Ala Gly Asp Asn Pro Tyr Leu Lys Tyr Asn His Ala Asp
                85                  90                  95
Ala Glu Phe Gln Glu Lys Leu Ala Asp Asp Thr Ser Phe Gly Gly Asn
            100                 105                 110
Leu Gly Lys Ala Val Phe Gln Ala Lys Lys Arg Val Leu Glu Pro Phe
        115                 120                 125
Gly Leu Val Glu Glu Gly Ala Lys Thr Ala Pro Thr Gly Lys Arg Ile
        130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Pro Leu Gly Asp Asn Asn Gln Gly Ala
        195                 200                 205
Asp Gly Val Gly Asn Ala Ser Gly Asp Trp His Cys Asp Ser Thr Trp
        210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
        275                 280                 285
Arg Leu Ile Asn Asn Tyr Trp Gly Phe Arg Pro Arg Ser Leu Arg Val
        290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gln Tyr Gly Tyr
        355                 360                 365
Ala Thr Leu Asn Arg Asp Asn Thr Glu Asn Pro Thr Glu Arg Ser Ser
        370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
        435                 440                 445
```

```
Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
            515                 520                 525

Phe Asn Ser Gln Gly Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
                580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
                660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 42
<211> LENGTH: 2203
<212> TYPE: DNA
<213> ORGANISM: adeno-associated virus 5

<400> SEQUENCE: 42
tttattgagg gtatgcgaca tgaatgggtt aaaggggtcg ggtaaggtat cgggttccga      60
taggtctggt ggttctgtat tccccggtgc tgtccggggc aaagtccaca aactgggggt     120
cgttgtagtt gtttgtgtac tggatctctg ggttccacct cttggagttt tccttcttga     180
gctcccactc catctccacg gtgaccctgcc cggtgctgta ctgggtgatg aagctgctga    240
cgggcacgtc cgagaagctg gtgatatttc cgggcacagg cgtgttcttg atgagcatca    300
tgggcggtgg gtgtttgagt ccgaatccgc ccatggccgg agagggtga aagtgcgccc     360 ccgtctctgg gatcttggcc cagatgggtc cttggaggta cacgtccctc tccatccaca    420
cgctgccggg cacgatttcc tggaggttgt acgtgccggt cgcggggggca gtggtggagc    480 tctggttgtt ggtggccatc tgcccgccga cgttgtacgc cacgcggttc accggctgcg    540
```

```
tctcgctctc gctggtgatg agcatgttgc cctcgaggta cgtggcggtg gtgcccgggt     600
tcgcccctg  gctgttgaag atcatagtgt tctccagggc ataggtgttg ctgccctgga     660
ggttgttggt catgccgttc ggctgcgggg gcacctggta actcgcgccc tcgagctcca     720
tcctattggt cgtggcgaag gcgctgacac tggcgcggtt gaccccggag cccaggttcc     780
agccctgggt tcggcccatg ggccccggga accagttttt gtaggtgttg gcgtatctcc     840
cggccaggtt cttgttgaac tggactccgc cagtgttatt tgtgctcacg aagcggtaca     900
agtactggtc caccagcggg ttggccagct tgaacaggtt ctgactggga gcgaagctgg     960
agtggaaggg cacctcctca aagttgtagg taaactcaaa gttgttgccc gttctcagca    1020
tcttgctggg aaagtactct aggcagaaga agctgctcct ctcggtggga ttttctgtgt    1080
tgtcgcggtt cagcgtcgcg taaccgtact gcggcagcgt aaagacctgc ggagggaagg    1140
ccggcaggca tccctcggtc ccgttgccga cgacgtaggg cagctggtag tcgtcgtccg    1200
taaacacttg gacggtggag gtgaggttgt tggcgatggt ggtggtggag tcctgcaccg    1260
tgacctcttt gacttgaatg ttgaagattt tgactctgag ggaccggggt ctgaagcccc    1320
agtagttgtt gatgagtctt tgccagtctc gggggctcca gtggctgtgg aagcggttaa    1380
agtcaaagta cccccagggg gtgctgtatc caaagtaggc gttggcgttg cttccgtcga    1440
cggagccgct tttgatctct cggtactggt ggttgttgta gctgggcagc acccaggttc    1500
gggtggactt ggtgacgact ctgtccccca tccacgtgga atcgcaatgc caatctcccg    1560
aggcattgcc cactccatcg gcaccttggt tattgtcgcc caatgggccg ccacctcccg    1620
cagacattgt atcagctccc aaacttgagg ctggttgggc tgggatttgc agctgctggg    1680
atccgctggg tccagcttcg gcgtctgacg aggtggaagg cttggagtcc tcttcggtcc    1740
gagccttctt tcttttttgga agtggtcgt ctatccgctt tccggtaggg gccgtcttag    1800
cacccctcttc aaccaggcca aaaggttcga gaacccttttt cttggcctga agactgcct    1860
ttccgaggtt tcccccgaag gatgtgtcgt cggcgagctt ctcctgaaac tcggcgtccg    1920
cgtggttgta cttgaggtag gggttgtctc ccgcctcaag ctgctcgttg tacgagatgt    1980
cgtgctctcg cgcgacctcg tctgccctgt tgacaggctc ctctgatcg agaccgtttc    2040
cgggtccgag atagttataa ccaggcagca caagaccacg ggcttgatct tgatgctgct    2100
gattgggttt tggtttcggt gggcccgctt caaggcccaa aaactcgcga agaccttcac    2160
caacttcttc caaccaatct ggagggtgat caacaaaaga cat                      2203
```

<210> SEQ ID NO 43
<211> LENGTH: 2194
<212> TYPE: DNA
<213> ORGANISM: adeno-associated virus 5

<400> SEQUENCE: 43

```
atgtctttttg ttgatcaccc tccagattgg ttggaagaag ttggtgaagg tcttcgcgag     60
tttttgggcc ttgaagcggg cccaccgaaa ccaaaaccca atcagcagca tcaagatcaa    120
gcccgtggtc ttgtgctgcc tggttataac tatctcggac ccggaaacgg tctcgatcga    180
ggagagcctg tcaacagggc agacgaggtc gcgcgagagc acgacatctc gtacaacgag    240
cagcttgagg cgggagacaa cccctacctc aagtacaacc acgcggacgc cgagtttcag    300
gagaagctcg ccgacgacac atccttcggg ggaaacctcg gaaaggcagt ctttcaggcc    360
aagaaaaggg ttctcgaacc ttttggcctg gttgagagg gtgctaagac ggcccctacc    420
```

```
ggaaagcgga tagacgacca ctttccaaaa agaaagaagg ctcggaccga agaggactcc    480
aagccttcca cctcgtcaga cgccgaagct ggacccagcg gatcccagca gctgcaaatc    540
ccagcccaac cagcctcaag tttgggagct gatacaatgt ctgcgggagg tggcggccca    600
ttgggcgaca ataaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag caccccctgg gggtactttg actttaaccg cttccacagc    840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacgacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca gatgctgag aacgggcaac   1200
aactttgagt ttacctacaa ctttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgcccccgca gccgaacggc atgaccaaca cctccagggg cagcaacacc   1560
tatgccctgg agaacactat gatcttcggg aagcaaggct cagagaaaac aaatgtggac   1620
attgaaaagg tcatgatcac cagcgagagc gagacgcagc cggtgaaccg cgtggcgtac   1680
aacgtcggcg ggcagatggc caccaacaac cagagctcca ccactgcccc cgcgaccggc   1740
acgtacaacc tccaggaaat cgtgcccggc agcgtgtgga tggagaggga cgtgtacctc   1800
caaggaccca tctgggccaa gatcccagag acggggcgc actttcaccc ctctccggcc   1860
atgggcggat tcggactcaa acacccaccg cccatgatgc tcatcaagaa cacgcctgtg   1920
cccggaaata tcaccagctt ctcggacgtg cccgtcagca gcttcatcac ccagtacagc   1980
accgggcagg tcaccgtgga gatggagtgg gagctcaaga aggaaaactc caagaggtgg   2040
aacccagaga tccagtacac aaacaactac aacgaccccc agtttgtgga ctttgccccg   2100
gacagcaccg gggaatacag aaccaccaga cctatcggaa cccgatacct acccgacccc   2160
ctttaaccca ttcatgtcgc atacctcaa taaa                                2194
```

<210> SEQ ID NO 44
<211> LENGTH: 721
<212> TYPE: PRT
<213> ORGANISM: adeno-associated virus 5

<400> SEQUENCE: 44

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

```
Asn Arg Ala Asp Glu Val Ala Arg Glu His Asp Ile Ser Tyr Asn Glu
 65                  70                  75                  80

Gln Leu Glu Ala Gly Asp Asn Pro Tyr Leu Lys Tyr Asn His Ala Asp
                 85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480
```

Val Asn Arg Ala Ser Val Ser Ala Phe Ala Thr Thr Asn Arg Met Glu
            485                 490                 495
Leu Glu Gly Ala Ser Tyr Gln Val Pro Pro Gln Pro Asn Gly Met Thr
        500                 505                 510
Asn Asn Leu Gln Gly Ser Asn Thr Tyr Ala Leu Glu Asn Thr Met Ile
        515                 520                 525
Phe Gly Lys Gln Gly Ser Glu Lys Thr Asn Val Asp Ile Glu Lys Val
    530                 535                 540
Met Ile Thr Ser Glu Ser Glu Thr Gln Pro Val Asn Arg Val Ala Tyr
545                 550                 555                 560
Asn Val Gly Gly Gln Met Ala Thr Asn Asn Gln Ser Ser Thr Thr Ala
                565                 570                 575
Pro Ala Thr Gly Thr Tyr Asn Leu Gln Glu Ile Val Pro Gly Ser Val
            580                 585                 590
Trp Met Glu Arg Asp Val Tyr Leu Gln Gly Pro Ile Trp Ala Lys Ile
        595                 600                 605
Pro Glu Thr Gly Ala His Phe His Pro Ser Pro Ala Met Gly Gly Phe
    610                 615                 620
Gly Leu Lys His Pro Pro Pro Met Met Leu Ile Lys Asn Thr Pro Val
625                 630                 635                 640
Pro Gly Asn Ile Thr Ser Phe Ser Asp Val Pro Val Ser Ser Phe Ile
                645                 650                 655
Thr Gln Tyr Ser Thr Gly Gln Val Thr Val Glu Met Glu Trp Glu Leu
            660                 665                 670
Lys Lys Glu Asn Ser Lys Arg Trp Asn Pro Glu Ile Gln Tyr Thr Asn
        675                 680                 685
Asn Tyr Asn Asp Pro Gln Phe Val Asp Phe Ala Pro Asp Ser Thr Gly
    690                 695                 700
Glu Tyr Arg Thr Thr Arg Pro Ile Gly Thr Arg Tyr Leu Thr Arg Pro
705                 710                 715                 720
Leu

<210> SEQ ID NO 45
<211> LENGTH: 2194
<212> TYPE: DNA
<213> ORGANISM: adeno-associated virus 5

<400> SEQUENCE: 45
tttattgagg gtatgcgaca tgaatgggtt aaaggggtcg ggtaaggtat cgggttccga     60
taggtctggt ggttctgtat tccccggtgc tgtccggggc aaagtccaca aactgggggt    120
cgttgtagtt gtttgtgtac tggatctctg ggttccacct cttggagttt ccttcttga    180 gctcccactc catctccacg gtgacctgcc cggtgctgta ctgggtgatg aagctgctga    240
cgggcacgtc cgagaagctg gtgatatttc cgggcacagg cgtgttcttg atgagcatca    300
tgggcggtgg gtgtttgagt ccgaatccgc ccatggccgg agaggggtga agtgcgccc    360 ccgtctctgg gatcttggcc cagatgggtc cttggaggta cacgtccctc tccatccaca    420
cgctgccggg cacgatttcc tggaggttgt acgtgccggt cgcgggggca gtggtggagc    480
tctggttgtt ggtggccatc tgcccgccga cgttgtacgc cacgcggttc accggctgcg    540
tctcgctctc gctggtgatc atgacctttt caatgtccac atttgttttc tctgagcctt    600
gcttcccgaa gatcatagtg ttctccaggg cataggtgtt gctgccctgg aggttgttgg    660
tcatgccgtt cggctgcggg ggcacctggt aactcgcgcc ctcgagctcc atcctattgg    720

```
tcgtggcgaa ggcgctgaca ctggcgcggt tgaccccgga gcccaggttc cagccctggg    780
ttcggcccat gggccccggg aaccagtttt tgtaggtgtt ggcgtatctc ccggccagt     840 tcttgttgaa ctggactccg ccagtgttat tgtgctcac gaagcggtac aagtactggt    900
ccaccagcgg gttggccagc ttgaacaggt tctgactggg agcgaagctg agtggaagg    960 gcacctcctc aaagttgtag gtaaactcaa agttgttgcc cgttctcagc atcttgctgg   1020
gaaagtactc taggcagaag aagctgctcc ctcggtggg attttctgtg ttgtcgcgt    1080 tcagcgtcgc gtaaccgtac tgcggcagcg taaagacctg cggagggaag gccggcaggc   1140
atccctcggt cccgttgccg acgacgtagg gcagctggta gtcgtcgtcc gtaaacactt   1200
ggacggtgga ggtgaggttg ttggcgatgg tggtggtgga gtcctgcacc gtgacctctt   1260
tgacttgaat gttgaagatt ttgactctga gggaccgggg tctgaagccc cagtagttgt   1320
tgatgagtct ttgccagtct cgggggctcc agtggctgtg gaagcggtta aagtcaaagt   1380 accccccaggg ggtgctgtat ccaaagtagg cgttggcgtt gcttccgtcg acggagccgc   1440
ttttgatctc tcggtactgg tggttgttgt agctgggcag cacccaggtt cgggtggact   1500
tggtgacgac tctgtccccc atccacgtgg aatcgcaatg ccaatctccc gaggcattgc   1560
ccactccatc ggcaccttgg ttattgtcgc caatgggcc gccacctccc gcagacattg    1620
tatcagctcc caaacttgag gctggttggg ctgggatttg cagctgctgg gatccgctgg   1680
gtccagcttc ggcgtctgac gaggtggaag gcttggagtc ctcttcggtc cgagccttct   1740
ttctttttgg aaagtggtcg tctatccgct ttccggtagg ggccgtctta gcaccctctt   1800
caaccaggcc aaaaggttcg agaacccttt tcttggcctg aaagactgcc tttccgaggt   1860
ttcccccgaa ggatgtgtcg tcggcgagct ctcctgaaa ctcggcgtcc gcgtggttgt    1920
acttgaggta ggggttgtct cccgcctcaa gctgctcgtt gtacgagatg tcgtgctctc   1980
gcgcgacctc gtctgccctg ttgacaggct ctcctcgatc gagaccgttt ccgggtccga   2040
gatagttata accaggcagc acaagaccac gggcttgatc ttgatgctgc tgattgggtt   2100
ttggtttcgg tgggcccgct tcaaggccca aaaactcgcg aagaccttca ccaacttctt   2160
ccaaccaatc tggagggtga tcaacaaaag acat                               2194
```

<210> SEQ ID NO 46
<211> LENGTH: 737
<212> TYPE: PRT
<213> ORGANISM: adeno-associated virus 7

<400> SEQUENCE: 46

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

```
Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
```

-continued

```
            530                 535                 540
Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
                580                 585                 590

Gln Thr Gln Val Val Asn Asn Gln Gly Ala Leu Pro Gly Met Val Trp
                595                 600                 605

Gln Asn Arg Asp Val Tyr Leu Gln Gly Pro Ile Trp Ala Lys Ile Pro
                610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
                675                 680                 685

Gln Lys Glu Asn Ser Lys Arg Trp Asn Pro Glu Ile Gln Tyr Thr Ser
                690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 47
<211> LENGTH: 519
<212> TYPE: PRT
<213> ORGANISM: adeno-associated virus 8

<400> SEQUENCE: 47

Asp Gly Val Gly Ser Ser Ser Gly Asn Trp His Cys Asp Ser Thr Trp
1               5                   10                  15

Leu Gly Asp Arg Val Ile Thr Thr Ser Thr Arg Thr Trp Ala Leu Pro
                20                  25                  30

Thr Tyr Asn Asn His Leu Tyr Lys Gln Ile Ser Asn Gly Thr Ser Gly
            35                  40                  45

Gly Ala Thr Asn Asp Asn Thr Tyr Phe Gly Tyr Ser Thr Pro Trp Gly
        50                  55                  60

Tyr Phe Asp Phe Asn Arg Phe His Cys His Phe Ser Pro Arg Asp Trp
65                  70                  75                  80

Gln Arg Leu Ile Asn Asn Asn Trp Gly Phe Arg Pro Lys Arg Leu Ser
                85                  90                  95

Phe Lys Leu Phe Asn Ile Gln Val Lys Glu Val Thr Gln Asn Glu Gly
            100                 105                 110

Thr Lys Thr Ile Ala Asn Asn Leu Thr Ser Thr Ile Gln Val Phe Thr
        115                 120                 125

Asp Ser Glu Tyr Gln Leu Pro Tyr Val Leu Gly Ser Ala His Gln Gly
    130                 135                 140

Cys Leu Pro Pro Phe Pro Ala Asp Val Phe Met Ile Pro Gln Tyr Gly
145                 150                 155                 160

Tyr Leu Thr Leu Asn Asn Gly Ser Gln Ala Val Gly Arg Ser Ser Phe
```

```
                165                 170                 175
Tyr Cys Leu Glu Tyr Phe Pro Ser Gln Met Leu Arg Thr Gly Asn Asn
            180                 185                 190
Phe Gln Phe Thr Tyr Thr Phe Glu Asp Val Pro Phe His Ser Ser Tyr
        195                 200                 205
Ala His Ser Gln Ser Leu Asp Arg Leu Met Asn Pro Leu Ile Asp Gln
    210                 215                 220
Tyr Leu Tyr Tyr Leu Ser Arg Thr Gln Thr Thr Gly Gly Thr Ala Asn
225                 230                 235                 240
Thr Gln Thr Leu Gly Phe Ser Gln Gly Gly Pro Asn Thr Met Ala Asn
                245                 250                 255
Gln Ala Lys Asn Trp Leu Pro Gly Pro Cys Tyr Arg Gln Gln Arg Val
            260                 265                 270
Ser Thr Thr Thr Gly Gln Asn Asn Asn Ser Asn Phe Ala Trp Thr Ala
        275                 280                 285
Gly Thr Lys Tyr His Leu Asn Gly Arg Asn Ser Leu Ala Asn Pro Gly
    290                 295                 300
Ile Ala Met Ala Thr His Lys Asp Asp Glu Glu Arg Phe Phe Pro Ser
305                 310                 315                 320
Asn Gly Ile Leu Ile Phe Gly Lys Gln Asn Ala Ala Arg Asp Asn Ala
                325                 330                 335
Asp Tyr Ser Asp Val Met Leu Thr Ser Glu Glu Glu Ile Lys Thr Thr
            340                 345                 350
Asn Pro Val Ala Thr Glu Glu Tyr Gly Ile Val Ala Asp Asn Leu Gln
        355                 360                 365
Gln Gln Asn Thr Ala Pro Gln Ile Gly Thr Val Asn Ser Gln Gly Ala
    370                 375                 380
Leu Pro Gly Met Val Trp Gln Asn Arg Asp Val Tyr Leu Gln Gly Pro
385                 390                 395                 400
Ile Trp Ala Lys Ile Pro His Thr Asp Gly Asn Phe His Pro Ser Pro
                405                 410                 415
Leu Met Gly Gly Phe Gly Leu Lys His Pro Pro Pro Gln Ile Leu Ile
            420                 425                 430
Lys Asn Thr Pro Val Pro Ala Asp Pro Pro Thr Thr Phe Asn Gln Ser
        435                 440                 445
Lys Leu Asn Ser Phe Ile Thr Gln Tyr Ser Thr Gly Gln Val Ser Val
    450                 455                 460
Glu Ile Glu Trp Glu Leu Gln Lys Glu Asn Ser Lys Arg Trp Asn Pro
465                 470                 475                 480
Glu Ile Gln Tyr Thr Ser Asn Tyr Tyr Lys Ser Thr Ser Val Asp Phe
                485                 490                 495
Ala Val Asn Thr Glu Gly Val Tyr Ser Glu Pro Arg Pro Ile Gly Thr
            500                 505                 510
Arg Tyr Leu Thr Arg Asn Leu
            515
```

ADENO-ASSOCIATED VECTORS FOR ENHANCED TRANSDUCTION AND REDUCED IMMUNOGENICITY

CROSS REFERENCE TO RELATED APPLICATION

This application claims the benefit of priority under 35 U.S.C. § 119(e) to U.S. Provisional Patent Application Ser. No. 61/143,524 filed Apr. 6, 2015, and to U.S. Provisional Patent Application Ser. No. 62/309,025, filed Mar. 16, 2016, each of which is incorporated herein by reference.

SEQUENCE LISTING

The present application is being filed with a Sequence Listing in electronic format. The Sequence Listing is provided as a file entitled 6137NIDCR-15-PROV_Sequence_Listing.txt, created Apr. 6, 2015, which is 217 kb in size. The information in the electronic format of the Sequence Listing is incorporated herein by reference in its entirety.

TECHNICAL FIELD

The invention relates adeno-associated viruses (AAVs) having modified capsid proteins, such that the modified AAV particles have enhanced transduction efficiency and reduced immunogenicity.

BACKGROUND OF DISCLOSURE

The first step in viral infection is attachment of the virus to the cell surface and cell surface carbohydrates play an important role in this process. Due to the broad array of structural motifs possible with carbohydrates compared to proteins, many viruses and pathogens utilize carbohydrates as initial cell attachment receptors. The carbohydrate moieties mediating these interactions are modified proteins or lipids in the form of glycoproteins and glycosphingolipids, respectively, or exist as glycosaminoglycan (GAG) chains attached to proteins in the form of proteoglycans.

As a genus, the *Dependoparvoviruses*, belonging to the ssDNA packaging Parvoviridae, use a diverse group of cell surface carbohydrates for attachment, entry, and cellular transduction. Adeno-associated virus serotype 2 (AAV2), AAV3B, AAV6, and AAV13 bind to heparin sulfate proteoglycans (HSPGs) (1-7). However, these viruses differ in their affinity and specificity for HS (1). AAV1, AAV4, AAV5, and AAV6 all use different forms of sialic acid (SIA) (7-10). While both AAV4 and AAV5 require the α2-3 form of SIA, treatment of cells with specific glycosylation inhibitors and re-sialation experiments with neuraminidase-treated erythrocytes demonstrated that AAV4 preferentially attached to an α2-3 SIA present on an O-linked carbohydrate core, and AAV5 attached to the N-linked type (8). Analysis of AAV1 and AAV6 determined that both use either α2,3-linked or α2,6-linked SIA when transducing numerous cell types and that SIA supersedes HS in controlling AAV6 transduction (7, 10). Similarly, an AAV isolate found as a contaminate in a stock of bovine adenovirus termed BAAV also requires cell surface SIA for transduction and internalization but the terminal SIA groups must be linked to a glycoshingolipid core of a ganglioside (11).

Carbohydrate structural motifs are not static and their presentation on the cells' surface varies with cell differentiation and maturation, all of which can affect viral attachment. Furthermore, their polarized surface expression or presence in the extracellular matrix or fluids, such as saliva or bronchoalveolar lavage fluid, can affect and block a virus's attachment to a cell. For example, the protective mucins secreted by airway epithelia are heavily glycosylated with an abundance of O-linked SIA. Binding and competition experiments demonstrate that AAV4 will bind to and is inhibited by purified muc-1 but not its deglycosylated form (9). In contrast, AAV5 only weakly binds muc-1 and its transduction is not inhibited in competition experiments or by bronchoalveolar fluid (9, 12).

Extensive mutagenesis on AAV2 localized its HS binding region to a basic patch of amino acids, with R585 and R588 (AAV2 VP1 numbering), located close to the top of the protrusions that surround the icosahedral threefold symmetry axis of the capsid, shown to be the most critical for this interaction (13, 14). Interestingly, while a mutation in this region blocks virus binding and transduction in vitro, it appears to alter but not ablate transduction in vivo. Kern et al. reported that a mutation of amino acids R585 and R588 in AAV2 results in a vector with improved specificity for heart tissue compared to WT virus, which can direct gene transfer to both the heart and liver. However, while insertion of the peptide comprising AAV2's residues 585-RGNR-588 onto AAV5 can confer heparin binding activity to this serotype; it does not confer sensitivity to heparin competition during transduction suggesting that cellular transduction by AAV5 is likely controlled by its initial SIA interaction which is not ablated by the peptide insert (14).

Adeno-associated viruses have emerged as one of the most promising vectors in the field of gene therapy. However, many current AAV vectors remain inefficient at delivering heterologous nucleic acid molecules to their intended target cells. Moreover, the ability of the immune response to recognize and mount an immune response against current AAV vectors limits the use of such vectors, particularly in cases where vectors are to be administered multiple times. Thus, a need exists for improved vectors for use in gene therapy and immunization applications. The present invention addresses such need and provides other benefits as well.

SUMMARY OF INVENTION

The present inventors used X-ray crystallography, mutagenesis, and glycan arrays to map the sialic acid (SIA) binding and transduction region on AAV5. X-ray data showed that SIA is able to bind at two sites on the surface of the viral particle. While mutations in both sites affected transduction activity, only one site at the center of the threefold axis of symmetry is responsible for the SIA dependent transduction and binding activity of AAV5. Binding specificity of the mutants on a glycan array confirmed the importance of this site in SIA binding and their effect on transduction activity. In vivo experiments showed that mutations of the SIA binding residues can alter AAV5 transduction activity in vivo and antibody neutralization studies confirmed the important of this site in AAV5 immunogenicity by creating escape mutants.

In one aspect, this disclosure provides a modified adeno-associated virus (AAV) capsid protein comprising at least one non-native amino acid at an amino acid position involved in binding of the capsid protein to a cellular receptor. In certain embodiments, the modified capsid protein is produced by modification of a capsid protein from an AAV virus selected from the group consisting of AAV1, AAV2, AAV3, AAV 3B, AAV4, AAV5, AAV6, AAV7, AAV8, AAV9, AVV10, AAV11, AAV12, BAAV, AAAV and AAV VR-942. In certain embodiments, the modified AAV capsid protein is produced by modification of a capsid protein from an AAV that binds sialic acid. In certain embodiments, the modified capsid protein is produced by modification of a capsid protein from an AAV virus selected from the group consisting of AAV1, AAV4, AAV5, AAV6 and AAV VR-942. In certain embodiments, the modified capsid protein is produced from a native AAV capsid protein comprising an amino acid sequence at least 80% identical to a sequence selected from the group consisting of SEQ ID NO:1, SEQ ID NO:2, SEQ ID NO:3, SEQ ID NO:3B, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12. In certain embodiments, the modified capsid protein is produced from a native AAV capsid protein comprising an amino acid sequence selected from the group consisting of SEQ ID NO:1, SEQ ID NO:2, SEQ ID NO:3, SEQ ID NO:3B, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12. In certain embodiments, the modified capsid protein is produced from a native AAV capsid protein comprising an amino acid sequence at least 80% identical to a sequence selected from the group consisting of SEQ ID NO:1, SEQ ID NO:4, SEQ ID NO:5 and SEQ ID NO:6. In certain embodiments, the modified capsid protein is produced from a native AAV capsid protein comprising an amino acid sequence selected from the group consisting of SEQ ID NO:1, SEQ ID NO:4, SEQ ID NO:5 and SEQ ID NO:6. In certain embodiments, the modification comprises an insertion, deletion or substitution of one or more amino acid residues into a native AAV capsid protein. In certain embodiments, the at least one non-native amino acid is present due to substitution of one or more amino acid positions in a native AAV capsid protein. In certain embodiments, the modified capsid protein comprises a modification of a sialic acid-binding AAV capsid protein, and the one or more amino acid(s) substituted at amino acid position(s) involved in binding of the capsid protein to a cellular receptor, is/are amino acids that are not present at corresponding locations in sialic acid-binding AAV capsid proteins. In certain embodiments, the modified capsid protein comprises a modification of a non-sialic acid-binding AAV capsid protein, the amino acid(s) being substituted at amino acid positions involved in binding of the capsid protein to a cellular receptor, is/are amino acids that are not present at corresponding locations in non-sialic acid-binding AAV capsid proteins. In certain embodiments, the modified capsid protein comprises an amino acid sequence at least 80% identical to the amino acid sequence of a wild-type AAV capsid protein, wherein the modified capsid protein comprises at least one non-native amino acid at a location of the capsid protein that interacts with a cellular receptor. In certain embodiments, the modified capsid protein comprises at least one non-native amino acid at a location of the capsid protein that interacts with sialic acid. In certain embodiments, the modified capsid protein comprises at least one non-native amino acid in the A-site or the B-site of the modified capsid protein.

In certain embodiments, the at least one non-native amino acid is at a location corresponding to a location in an AAV5 capsid protein selected from the group consisting of R277, H279, S280, E350, G351, C352, L353, P354, Q359, F361, T362, P553, F650, S651, D652, F529, N530, S531, L548, Q604 and T711. In certain embodiments, the modified AAV capsid protein comprises an amino acid sequence at least 80% identical to the amino acid sequence of a wild type AAV1, AAV4, AAV5 or AAV6 capsid protein, and wherein the at least one non-native amino acid is at a location corresponding to a location in an AAV5 capsid protein selected from the group consisting of R277, H279, S280, E350, G351, C352, L353, P354, Q359, F361, T362, P553, F650, S651, D652, F529, N530, S531, L548, Q604 and T711. In certain embodiments, the modified AAV capsid protein comprises an amino acid sequence at least 80% identical to a sequence selected from the group consisting of SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38 and SEQ ID NO:41, wherein the modified capsid protein has a non-native amino acid at a location corresponding to a location in the AAV5 capsid protein selected from the group consisting of R277, H279, S280, E350, G351, C352, L353, P354, Q359, F361, T362, P553, F650, S651, D652, F529, N530, S531, L548, Q604 and T711. In certain embodiments, the modified AAV capsid protein comprises an amino acid sequence selected from the group consisting of SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38 and SEQ ID NO:41.

In a second aspect, this disclosure provides a nucleic acid molecule encoding the modified AAV capsid protein described by any one of the embodiments of the first aspect of this disclosure.

In a third aspect, this disclosure provides a nucleic acid vector comprising the nucleic acid molecule of the second aspect of this disclosure. In certain embodiments, the nucleic acid vector is a plasmid. In other embodiments, the vector is a viral genome.

In a fourth aspect, this disclosure provides a virus comprising the nucleic acid molecule of the second aspect of this disclosure.

In a fifth aspect, this disclosure provides a virus comprising the modified AAV capsid protein of the first aspect of this disclosure. In certain embodiments, the virus is an adeno-associated virus. In certain embodiments, the virus is selected from the group consisting of AAV1, AAV2, AAV3, AAV3B, AAV4, AAV5, AAV6, AAV7, AAV8, AAV9 and AAV10. In certain embodiments, the virus is an AAV virus that binds sialic acid. In certain embodiments, the virus is AAV4, AAV5 or AAV6. In certain embodiments, the virus comprises an additional heterologous protein.

In a sixth aspect, this disclosure provides a kit comprising the virus of the fifth aspect of this disclosure.

In a seventh aspect, this disclosure provides a method to produce an AAV having increased transduction efficiency, the method comprising producing an AAV comprising the modified AAV capsid protein of the first aspect of this disclosure.

In an eighth aspect, this disclosure provides a method to increase the transduction efficiency of an adeno-associated virus (AAV), the method comprising producing an AAV comprising a capsid protein of the first aspect of this disclosure.

In a ninth aspect, this disclosure provides a method to decrease the immunogenicity of an adeno-associated virus (AAV), the method comprising producing an AAV comprising the modified AAV capsid protein of the first aspect of this disclosure.

A tenth aspect of this disclosure provides a method for treating a disease in an individual, the method comprising administering to an individual the virus of the fifth aspect of this disclosure.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

BRIEF DESCRIPTION OF DRAWINGS

FIG. 1A is a surface representation of the AAV5 capsid with the icosahedral reference (REF:), fivefold (5F), and threefold (3F) symmetry related VP3 monomers labeled and colored differently. The residues interacting with the SIA in the A-site and B-site are depicted lighter and darker, respectively. The SIA coordinates are shown as a stick model. The SIA is modeled inside the Fo-Fc electron density map contoured at threshold of 2.0σ (mesh). FIG. 1B depicts a close-up of the SIA binding pocket in the A-site with the ribbon diagram of the VP3 from the reference (gray) and threefold symmetry related monomers within a transparent density surface. FIG. 1C shows the amino acid residues from the reference and one of the threefold related monomers that interact with the SIA in the A-site are depicted in the stick model. FIG. 1D is a close-up of the SIA binding pocket in the B-site with the ribbon diagram of the VP3 from the reference (gray) within a transparent density surface. The A-site binding region is shown in red on the ribbon diagram. FIG. 1E depicts the amino acid residues from the reference (gray) and fivefold related monomer that interact with the SIA, and GOL in the B-site are depicted in a stick model. In FIGS. 1A, 1B, and 1D, the positions of icosahedral two-, three-, and five-fold symmetry axes are depicted as a black filled oval, triangle, and pentagon, respectively.

FIG. 6B), or lungs (FIG. 6C). Relative luciferase expression was visualized by Xenogen imaging.

In FIG. 8A, the capsid is viewed down the icosahedral three-fold axis, and FIG. 8B depicts the side view of the three-fold axis. In these figures, the residues are labeled by type (three letter code) and number (AAV5 VP1 numbering). The boundary for each residue is shown in black. The amino acid residues that are exposed on the capsid exterior are visible in this image. The key for the receptor attachment residues in FIGS. 8A and 8B is (AAVS VP1 residue numbering in parentheses):

Figure 1A:
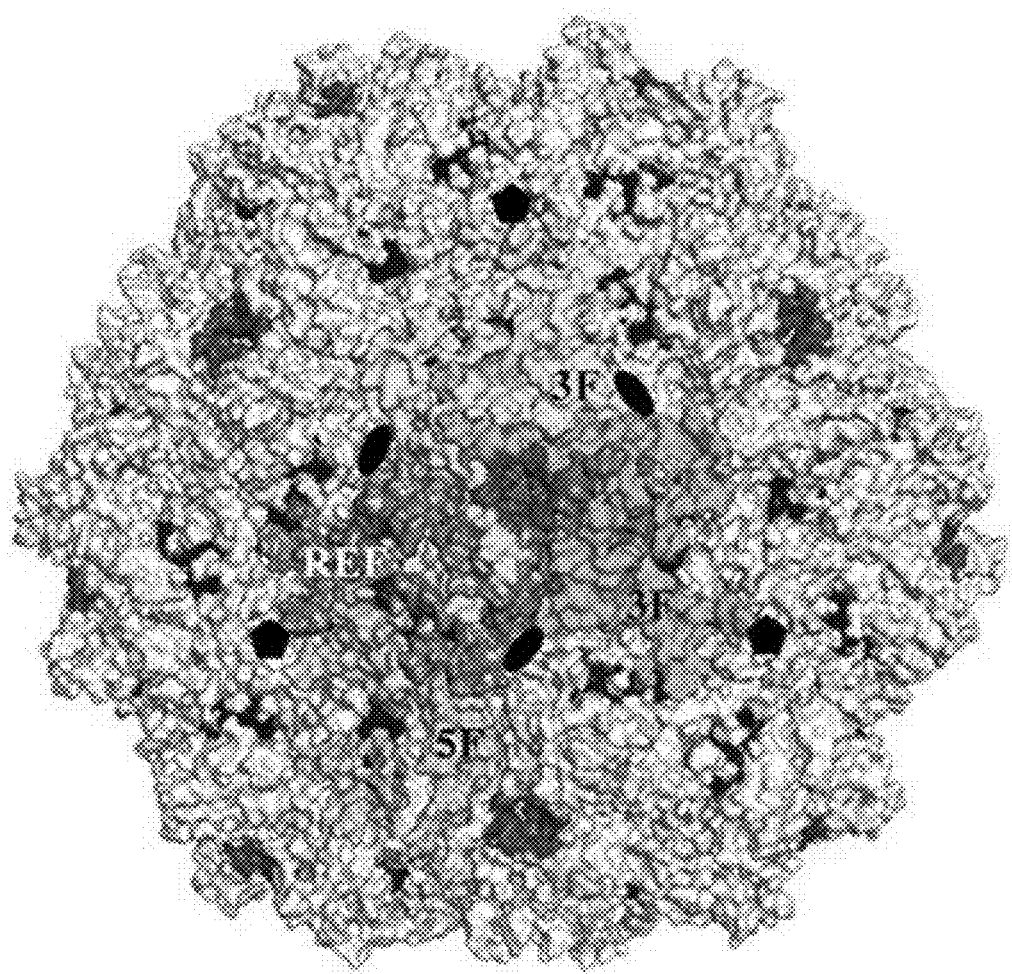
FIGS. 1A-1E depict the SIA binding site on the AAV5 capsid.
Figure 1B:
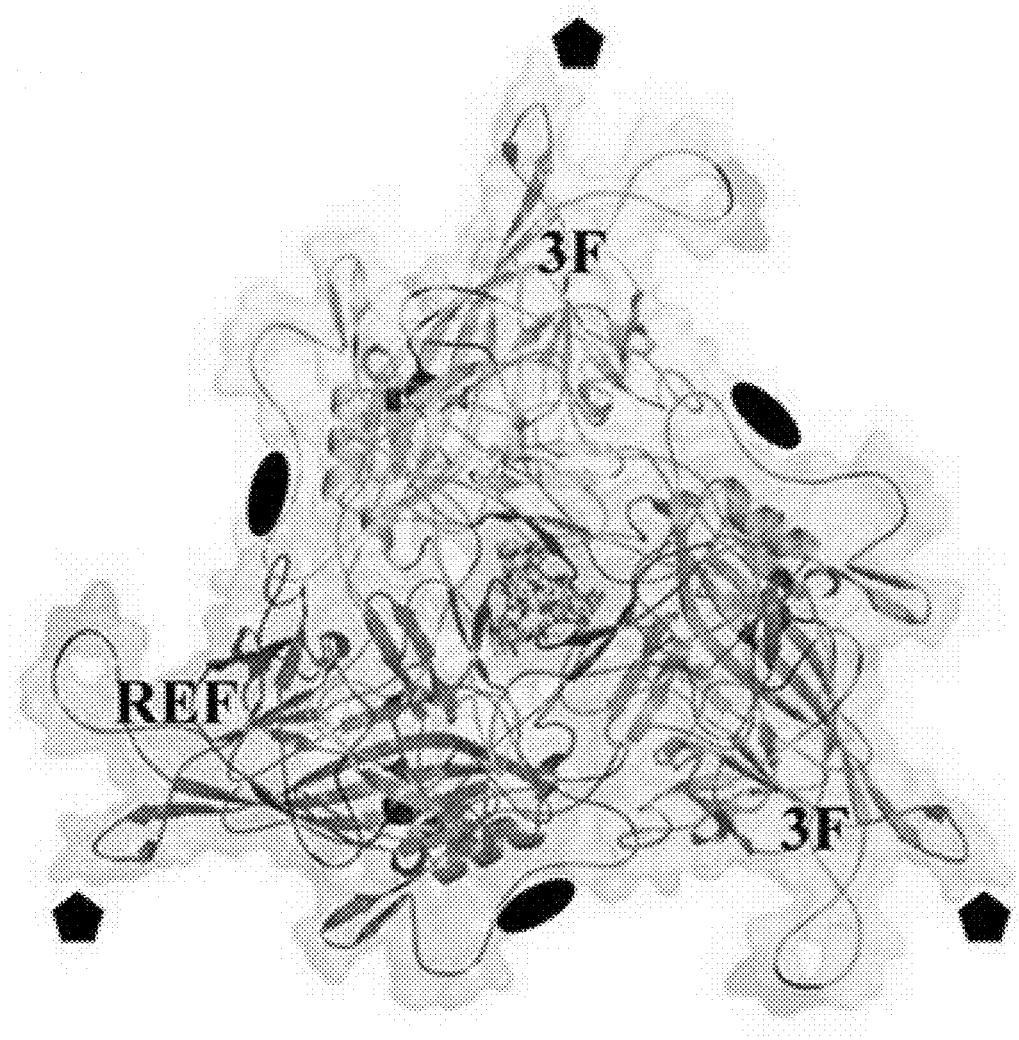

AAV2: R484 (R471); R487 (G474); K532 (N519); R585 (S575); R588 (T578)
AAV3b: R594 (G583)
AAV4: K492 (V486); K503 (A490); M523 (M511); G581 (N572); Q583 (Q574); N585 (S576)
AAV5: A581
AAV5: M569; A570, T571, G583, T584, Y585, N586, L587
AAV6: K531 (S518); K459 (N442); K493 (N482); R576 (V565)
AAV_VR942 (AAV13): K528 (S518)
AAV9: D271 (A260); N272 (N261); Y446 (R437); N470 (R456); W503 (F489)

FIG. 9 shows an alignment of amino acid sequences of capsid proteins from AAV5 (SEQ ID NO:6) with: AAV2 (SEQ ID NO:2), AAV7 (SEQ ID NO:46), AAV8 (SEQ ID NO:47), and AAV9 (SEQ ID NO:8).

FIG. 10 shows photon imaging of an eye following subretinal injection of a recombinant virus comprising the L587T capsid mutant and a negative control.

DETAILED DESCRIPTION OF THE EMBODIMENTS

The present disclosure provides novel, modified adeno-associated virus (mAAV) capsid proteins and modified AAV (mAAV) virions produce using such proteins. Modified AAV capsid proteins of the invention are produced by introducing mutations into specific locations of a nucleic acid molecule encoding an AAV capsid protein. The locations of the mutations are chosen so that the resulting alterations in the AAV capsid protein amino acid sequence occur in specific locations in the AAV capsid protein, resulting in the modified capsid proteins having phenotypic properties that differ from those of the capsid protein used to produce the modified capsid protein. Consequently, when the modified capsid proteins are used to produce AAV virions, the resulting virions have properties that differ from those observed in AAV virions having un-modified capsid proteins (e.g., wild-type (wt)). Such properties include, for example, altered receptor recognition, altered receptor binding affinity, enhanced transduction efficiency, reduced immunogenicity and reduced binding of the modified AAV virion by neutralizing antibodies. Thus, a general embodiment of the invention can be practiced by producing nucleic acid molecules encoding capsid proteins having an altered amino acid sequence at the specific regions disclosed herein. Another general embodiment of the present invention can be practiced by using such nucleic acid molecules, and/or such modified capsid proteins, to produce mAAVs having novel and advantageous properties.

It will be understood that this invention is not limited to the particular embodiments described herein, as such may, of course, vary. It is also to be understood that the terminology used herein is for the purpose of describing particular invention only, and is not intended to be limiting, since the scope of the present invention will be limited only by the claims.

Before embodiments of the invention are described in greater detail, it should be understood that as used herein and in the appended claims, the singular forms "a," "an," and "the" include plural referents unless the context clearly dictates otherwise. It is further noted that the claims may be drafted to exclude any optional element. For example, a nucleic acid molecule refers to one or more nucleic acid molecules. As such, the terms "a", "an", "one or more" and "at least one" can be used interchangeably. This statement is intended to serve as antecedent basis for use of such exclusive terminology as "solely," "only" and the like in connection with the recitation of claim elements, or use of a "negative" limitation. Similarly, the terms "comprising", "including" and "having" can be used interchangeably.

Unless otherwise specified, the term "about", when referring to a measurable value, such as the length of a polypeptide or nucleotide sequence, a dosage, a time, temperature, and the like, unless otherwise specified is meant to encompass variations of ±20%, ±15%, ±10%, ±5%, ±1%, ±0.5%, or even ±0.1%, of the specified amount.

The term "parvovirus" as used herein encompasses the family Parvoviridae, including autonomously replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., Bernard N. Fields et al., VIROLOGY, volume 2, chapter 69 (4th ed., Lippincott-Raven Publishers).

"AAV" is an abbreviation for adeno-associated virus, and may be used to refer to the virus itself or derivatives thereof. Unless otherwise indicated, the term covers all subtypes and both naturally occurring and recombinant forms. The term AAV (and adeno-associated virus), includes but is not limited to, all types of adeno-associated viruses, examples of which include AAV type 1 (AAV1), AAV type 2 (AAV2), AAV type 3 (including types 3A and 3B) (AAV3 and AAV3B), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), avian AAV (AAAV), bovine AAV BAAV), canine AAV, equine AAV, ovine AAV, Clade F AAV and any other AAV now known or later discovered. See, e.g., Beranrd N. Fields of al., VIROLOGY, volume 2, chapter 69 (4th ed., Lippincott-Raven Publishers). A number of relatively new AAV serotypes and clades which have been identified (see, e.g., Gao et al. (2004) J. Virology 78:6381-6388; Moris et al. (2004) Virology 33:375-383), are also encompassed herein.

The term vector is used in various embodiments described and the meaning of such term may vary depending on the context in which it is used. The term AAV nucleic acid vector, AAV vector, and the like, refers to nucleic acid molecules comprising inverted terminal repeats (ITR) from an AAV, at least one such ITR comprising cis-acting genetic elements necessary for packaging (i.e., encapsulation) of the AAV nucleic acid vector by AAV capsid proteins. Examples of such cis-acting genetic elements include, but are not limited to, an AAV Rep binding site and a terminal resolution site (trs). In preferred embodiments, such AAV nucleic acid vectors contain all nucleic acid sequences and structures required for packaging within AAV capsid proteins. In some instances, AAV nucleic acid vectors comprise a promoter between the AAV ITRs. In further instances, the AAV nucleic acid vector can comprise a gene or ORF (either native or heterologous) functionally linked to a promoter, both the promoter and the gene or ORF being located between the AAV ITRs. Examples of such vectors are described, for example, in U.S. Pat. No. 8,927,269, which is incorporated herein by reference in its entirety.

An AAV virus, AAV viral particle, AAV viral vector, AAV virion, and the like, refers to a viral particle composed of at least one AAV capsid protein (either wild-type or modified) and an encapsidated AAV nucleic acid vector. If the AAV nucleic acid vector is recombinant (e.g., comprises a heterologous polynucleotide or a genetically engineered AAV nucleic acid molecule), the particle carrying such recombinant AAV nucleic acid vector can be referred to as an rAAV particle, rAAV virion, rAAV vector particle or simply an rAAV vector. Thus, production of rAAV particle necessarily includes production of recombinant AAV nucleic acid vector. AAV virions made using modified capsid proteins of the present invention can be referred to as modified AAV virions.

The term "polynucleotide" refers to a polymeric form of nucleotides of any length, including deoxyribonucleotides or ribonucleotides, or combinations and analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified, any embodiment of the invention described herein that is a polynucleotide encompasses both the double-stranded form and each of two complementary single-stranded forms known or predicted to make up the double-stranded form.

As used herein, the terms isolated, isolating, purified, and the like, do not necessarily refer to the degree of purity of a cell or molecule of the present invention. Such terms instead refer to cells or molecules that have been separated from their natural milieu or from components of the environment in which they are produced. For example, a naturally occurring cell or molecule (e.g., a DNA molecule, a protein, etc.) present in a living animal, including humans, is not isolated.

However, the same cell, or molecule, separated from some or all of the coexisting materials in the animal, is considered isolated. As a further example, according to the present invention, protein molecules that are present in a sample of blood obtained from an individual would be considered isolated. It should be appreciated that protein molecules obtained from such a blood sample using further purification steps would also be referred to as isolated, in accordance with the notion that isolated does not refer to the degree of purity of the protein. For example, depending on the intended use, an isolated protein may be enriched by at least 10-fold, 100-fold, 1,000-fold, 10,000-fold, or more, as compared with the starting material.

It is to be appreciated that certain features of the invention, which are, for clarity, described in the context of separate invention, may also be provided in combination in a single embodiment. Conversely, various features of the invention, which are, for brevity, described in the context of a single embodiment, may also be provided separately or in any suitable sub-combination. All combinations of the invention are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein. Moreover, as used herein, the term and/or refers to and encompasses any and all possible combinations of one or more of the associated listed items, as well as the lack of combinations, when interpreted in the alternative (e.g., "or").

It is to be further understood that the publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and materials for which the publications are cited.

The present invention is based on the inventors surprising discovery that modification of specific amino acid sequences of AAV capsid protein can alter the properties of the capsid protein. Moreover, the inventors have further discovered that AAV particles comprising such modified capsid proteins, have altered, often beneficial, properties such as increased or reduced transduction efficiencies and increased resistance to binding by a neutralizing antibody. Thus, one embodiment of the present invention is a modified adeno-associated virus (AAV) capsid protein comprising at least one non-native amino acid at an amino acid sequence location known to be involved in binding of the capsid protein to a cell receptor.

An AAV capsid protein (also referred to as an AAV coat protein) is an AAV protein capable of encapsulating an AAV nucleic acid vector, thereby forming an AAV virion. AAV capsid proteins are known to those skilled in the art and the sequences of such capsid proteins can be found in the scientific literature or in publicly available databases such as the National Institutes of Health (NIH) Protein Databank (PDB), the NIH GenBank Database and UniProtKB/Swis-Prot. Examples of useful AAV capsid proteins include AF063497.1 (AAV1), AF043303.1 (AAV2), U48704.1 (AAV3), AF028705.1 (AAV3B), U89790.1 (AAV4), AF085716.1 (AAV5), AF028704.1 (AAV6), AAS99264 (AAV9), ABI6639 (AAV12), EU285562 (AAV13; VR-942), NC_004828 (AAAV), AY388617 (BAAV), NC_006260 (AAV7) and PDB:3RAA_A (AAV8). Examples of AAV capsid protein amino acid sequences useful for creating modified capsid proteins of the present invention include SEQ ID NO:1, SEQ ID NO:2, SEQ ID NO:3, SEQ ID NO:3B, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 SEQ ID NO:46 and SEQ ID NO:47. These sequences are described in the Table below.

| SEQ ID NO: | Molecule | Notes |
|---|---|---|
| 1 | Amino acid sequence of wild-type AAV1 capsid protein | AF063497.1 |
| 2 | Amino acid sequence of wild-type AAV2 capsid protein | AF043303.1 |
| 3 | Amino acid sequence of wild-type AAV3 capsid protein | U48704.1 |
| 4 | Amino acid sequence of wild-type AAV3B capsid protein | AF028705.1 |
| 5 | Amino acid sequence of wild-type AAV4 capsid protein | U89790.1 |
| 6 | Amino acid sequence of wild-type AAV5 capsid protein | AF085716.1 |
| 7 | Amino acid sequence of wild-type AAV6 capsid protein | AF028704.1 |
| 8 | Amino acid sequence of wild-type AAV9 capsid protein | AAS99264 |
| 9 | Amino acid sequence of wild-type AAV12 capsid protein | ABI16639 |
| 10 | Amino acid sequence of wild-type AAV VR-942 capsid protein | EU285562 |
| 11 | Amino acid sequence of wild-type AAAV capsid protein | NC_004828 |
| 12 | Amino acid sequence of wild-type BAAV capsid protein | AY388617 |
| 13 | Nucleotide sequence of modified capsid protein M569V | AAV5-A site mutant |
| 14 | Amino acid sequence encoded by SEQ ID NO: 13 | |
| 15 | Complement of 13 | |
| 16 | Nucleotide sequence of modified capsid protein Y585V | AAV5-A site mutant |
| 17 | Amino acid sequence encoded by SEQ ID NO: 16 | |
| 18 | Complement of 16 | |
| 19 | Nucleotide sequence of modified capsid protein L587T | AAV5-A site mutant |
| 20 | Amino acid sequence encoded by SEQ ID NO: 19 | |
| 21 | Complement of 19 | |
| 22 | Nucleotide sequence of modified capsid protein Y585V/L587T | AAV5-A site mutant |
| 23 | Amino acid sequence encoded by SEQ ID NO: 22 | |
| 24 | Complement of 22 | |
| 25 | Nucleotide sequence of modified capsid protein D652A | AAV5-B site mutant |

-continued

| SEQ ID NO: | Molecule | Notes |
|---|---|---|
| 26 | Amino acid sequence encoded by SEQ ID NO: 25 | |
| 27 | Complement of 25 | |
| 28 | Nucleotide sequence of modified capsid protein T362M | AAV5-B site mutant |
| 29 | Amino acid sequence encoded by SEQ ID NO: 28 | |
| 30 | Complement of 28 | |
| 31 | Nucleotide sequence of modified capsid protein Q359D | AAV5-B site mutant |
| 32 | Amino acid sequence encoded by SEQ ID NO: 31 | |
| 33 | Complement of 31 | |
| 34 | Nucleotide sequence of modified capsid protein E350Q | AAV5-B site mutant |
| 35 | Amino acid sequence encoded by SEQ ID NO: 34 | |
| 36 | Complement of 34 | |
| 37 | Nucleotide sequence of modified capsid protein P533S | AAV5-B site mutant |
| 38 | Amino acid sequence encoded by SEQ ID NO: 37 | |
| 39 | Complement of 37 | |
| 40 | Nucleotide sequence of modified capsid protein P533G | AAV5-B site mutant |
| 41 | Amino acid sequence encoded by SEQ ID NO: 40 | |
| 42 | Complement of 40 | |
| 43 | Nucleotide sequence of modified capsid protein loop VII | AAV5-mutation in loop VII |
| 44 | Amino acid sequence encoded by SEQ ID NO: 43 | |
| 45 | Complement of 40 | |
| 46 | Amino acid sequence of wild-type AAV7 capsid protein | NC_006260 |
| 47 | Amino acid sequence of wild-type AAV8 capsid protein | PDB:3RAA_A |

As used herein, a modified AAV capsid protein is an AAV capsid protein in which one or more sequence locations in an AAV capsid protein have been altered relative to the corresponding sequence location(s) in a native capsid protein from the same type of AAV. According to the present invention, a native capsid protein is defined based on comparison with the amino acid sequence of a capsid protein from an AAV found in nature (i.e., wt AAV capsid sequence). One example of a wt AAV capsid protein is represented by SEQ ID NO: 6 (AAV5 capsid protein). In particular, a native AAV capsid protein is any AAV capsid protein having an amino acid sequence at least 80% identical, at least 85% identical, at least 90% identical, at least 95% identical or at least 97% identical to the amino acid sequence of a wt capsid protein, wherein the amino acid residue present in at least one location being altered in the native protein, is the same type of amino acid present at the corresponding location in the wild-type AAV capsid protein. Examples of representative, wild-type AAV capsid proteins include SEQ ID NO:1, SEQ ID NO:2, SEQ ID NO:3, SEQ ID NO:3B, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 SEQ ID NO:46 and SEQ ID NO:47. From this definition, it should be clear to one skilled in the art that a native AAV capsid protein and a wt AVV capsid protein, can, but need not, be identical over their entire sequences. The following example, which is simply for clarification purposes and is not meant to limit the claimed invention, will further illustrate what is meant by native and modified AAV5 capsid proteins. To create a modified AAV5 capsid protein having a modification at amino acid position 277 of the AAV5 capsid protein, one skilled in the art could start with a native, AAV5 capsid protein, the sequence of which is represented by SEQ ID NO:6. The amino acid at position 277 of SEQ ID NO:6 is an arginine. Thus, in this example, a native AAV5 capsid protein is any AAV capsid protein comprising an amino acid sequence at least 80% identical, at least 85% identical, at least 90% identical, at least 95% identical or at least 97% identical to SEQ ID NO:6, wherein the amino acid at position 277 is an arginine. Alteration of the arginine at position 277 of the native AAV5 capsid protein, with any amino acid other than arginine, result in the creation of a modified AAV5 capsid protein. It should be understood that if alterations are to be made at multiple locations of the AAV5 capsid protein, the starting protein (which is at least 80% identical, at least 85% identical, at least 90% identical, at least 95% identical or at least 97% identical to the amino acid sequence of an AAV5 protein such as SEQ ID NO:6) need only have the same type of amino acid as the wt AAV5 capsid protein sequence at a single corresponding location to be altered, in order to be considered a native AAV 5 capsid. For example, if one skilled in the art intends to alter positions 287 and 587 of an AAV5 capsid protein, the staring (native) protein need only have the same type amino acid as the wt AAV5 capsid protein (e.g., SEQ ID NO:6) at one position (i.e., either position 277 or position 587). Examples of modified AAV5 capsid protein are represented by SEQ ID NOs: 17, 20 and 41, which have been modified at positions 585, 587 and 533, respectively, relative to wt AAV5 capsid protein (e.g., SEQ ID NO:6).

As used herein, a native amino acid is an amino acid found at a specified location in a native, AAV capsid protein. It should be understood that, native amino acid residues will usually be identified by their position relative to the amino acid sequence of a native AAV capsid protein. For example, using SEQ ID NO:6 as the sequence of a native AAV5 capsid protein, the native amino acid at position 277 is arginine. Accordingly, as used herein, a non-native amino acid is any amino acid other than the native amino acid found at a specified location in a native AAV capsid protein. Thus, continuing with the example above, if the AAV5 capsid protein were modified by replacing the arginine at position 277 with, for example, an alanine, then the alanine would be considered a non-native amino acid.

Amino acid sequence alterations suitable for producing modified AAV capsid proteins of the present invention include substitutions, insertions or deletions of one of more (e.g., 2, 3, 4, 5, 6, 7, 8, 9, 10 or more) amino acid residues at a designated location. As used herein, the terms alterations, changes, modifications, mutations, and the like, can be used interchangeably. In a preferred embodiment, the amino acid sequence alterations are intentional alterations. According to the present invention, the term intentional alterations, intentionally altered, and the like, refer to changes to the capsid protein amino acid sequences created by the hand of man. Such changes can be targeted changes, meaning the altered locations were deliberately chosen, or they may random changes, meaning that the modified capsid protein was created using techniques (e.g., mismatch PCR, mutagenic chemicals) known to result in alterations of amino acid sequences. Such mutagenic techniques are known to those skilled in the art.

As noted above, intentional alterations include substitutions, deletions and insertions at specific locations in an AAV capsid protein. While any type of intentional alteration in sequence can be used to practice the present invention, a preferred intentional alteration is a substitution mutation. Thus, in one embodiment, 1, 2, 3, 4, 5, 6, 7, 8, 9, 10, 11, 12, 13, 14, 15, 16, 17, 18, 19, 20 or more, amino acids can be substituted into specific amino acid positions to create the modified protein. In one embodiment, 1, 2, 3, 4, 5, 6, 7, 8, 9, 10, 11, 12, 13, 14, 15, 16, 17, 18, 19, 20 or more, amino acids are substituted with the corresponding 1, 2, 3, 4, 5, 6, 7, 8, 9, 10, 11, 12, 13, 14, 15, 16, 17, 18, 19, 20 or more, amino acids from a capsid protein from the same, or different, type of AAV. A preferred alteration to make is a substitution mutation in which a single amino acid in the native AAV capsid protein, the native amino acid being known to interact with a cell receptor, is replaced with a non-native amino acid. It should be understood that modified proteins of the present invention can comprise one or more of such single, substitution mutations.

A preferred location at which to alter the sequence of an AAV capsid protein is at an amino acid location in the native protein known to be involved in binding of the capsid protein to a receptor protein. As has been described previously, many viruses use utilize various carbohydrates as initial cell attachment receptors. The carbohydrate moieties mediating these interactions are modified proteins or lipids in the form of glycoproteins and glycosphingolipids, respectively, or they exist as glycosaminoglycan (GAG) chains attached to proteins in the form of proteoglycans. Side chains on specific amino acids of the AAV capsid protein interact with atoms located on the carbohydrate portion of the receptor, resulting in binding of the AAV to the cell. Viruses in the genus *Dependoparvoviruses*, which includes AAVs, use a diverse group of cell surface carbohydrates for attachment, entry, and cellular transduction. For example, AAV2, AAV3B, AAV6, and AAV13 bind to heparin sulfate proteoglycans (HSPGs), whereas AAV1, AAV4, AAV5, and AAV6 all use different forms of sialic acid (SIA). While both AAV4 and AAV5 require the α2-3 form of SIA, AAV4 preferentially attached to an α2-3 SIA present on an O-linked carbohydrate core, whereas AAV5 preferentially to the N-linked carbohydrate). AAV1 and AAV6 both use either α2,3-linked or α2,6-linked SIA when transducing numerous cell types and the use of SIA supersedes the use of HS in controlling AAV6 transduction. Similarly, an AAV isolate found as a contaminate in a stock of bovine adenovirus (BAAV) also requires cell surface SIA for transduction and internalization. However, the terminal SIA groups must be linked to a glycoshingolipid core of a ganglioside. While the AAV capsid protein used to create a modified AAV capsid protein can be from any AAV, preferred capsid proteins to use are those from sialic acid-binding AAVs. Thus, in one embodiment, the modified capsid protein is made using a native capsid protein from an AAV that binds sialic acid. In one embodiment, the modified capsid protein is made using a native capsid protein from AAV1, AAV4, AAV5 or AAV6.

In one embodiment, the modified capsid protein is made using a native capsid protein comprising an amino acid sequence at least 80% identical, at least 85% identical, at least 90% identical, at least 95% identical or at least 97% identical to an amino acid sequence selected from the group consisting of SEQ ID NO:1, SEQ ID NO:5, SEQ ID NO:6 and SEQ ID NO:7, wherein the type amino acid present in at least one location being modified in the native protein is the same as the type of amino acid present at the corresponding location in the wt AAV capsid protein. In one embodiment, the modified capsid protein is made using a native capsid protein comprising an amino acid sequence selected from the group consisting of SEQ ID NO:1, SEQ ID NO:5, SEQ ID NO:6 and SEQ ID NO:7.

In one embodiment, modification of the amino acid sequence of an AAV capsid protein is made in the A-site or the B-site of a capsid protein from a sialic acid-binding AAV. As described herein, the A-site and B-site are structurally mapped regions of positive electron density located at the threefold axis and underneath the H1 loop, respectively. Thus, in one embodiment, one or more modifications are made in the A-site of an AAV capsid protein. Any location within the A-site can be altered to create a modified AAV capsid protein of the invention. Preferred locations at which to alter the amino acid sequence are those amino acids in the A-site known to interact (e.g., ionically bond) with the cell receptor. Particularly preferred locations at which to modify the amino acid sequence are those amino acids in the A-site known to interact with sialic acid. In a further embodiment, modifications are made at a location corresponding to an AAV5 capsid protein location selected from the group consisting of M569, A570, T571, G583, T584, Y585, N586 and L587.

In one embodiment, one or more alterations are made in the B-site of an AAV capsid protein. Any location within the B-site can be altered to create a modified AAV capsid protein of the invention. Preferred locations at which to alter the amino acid sequence are those amino acids in the B-site known to interact with the cell receptor. Particularly preferred locations at which to alter the amino acid sequence are those amino acids in the B-site known to interact with sialic acid. In a further embodiment, alterations are made at a location corresponding to an AAV5 capsid protein location selected from the group consisting of R277, H279, S280, E350, G351, C352, L353, P354, Q359, F361, T362, P553, F650, S651, D652, F529, N530, S531, L548, Q604 and T711.

In a further embodiment, modifications are made at a location corresponding to loop VII of an AAV5 capsid protein. Such modifications can comprise a single sequence modification in loop VII or more than one sequence modifications. In one embodiment, the entire sequence of loop VII is replaced.

While any non-native amino acid can be substituted into a native, sialic acid-biding, AAV capsid protein to produce a modified AAV capsid protein of the present invention, in preferred embodiments, the non-native amino acids are limited to a specific subset of amino acids, the composition of which is dependent on the position of the amino acid being altered. Specifically, preferred non-native amino acids to substitute into the native, sialic acid-binding AAV capsid protein are amino acids that are not present in corresponding locations in non-sialic acid-binding AAV capsid proteins. For example, to make a modified AAV5 capsid protein which is modified at position 587, the first thing to note is that position 587 of the AAV5 capsid protein contains a leucine. Thus, to make a modified AAV5 capsid protein modified at position 587, the leucine at that position could be substituted at with any amino acid other than leucine, as long as the amino acid replacing the leucine is not present at the corresponding location in a non-sialic acid-binding AAV capsid protein. Thus, to determine which amino acids can be used, a person skilled in the art only need to look at the amino acids present at the position corresponding to amino acid 587 in capsid proteins of non-sialic binding AAVs. Any amino acid present at such location would not be used to create the modified capsid protein. To further illustrate this aspect of the invention, FIG. 9 shows an alignment of a native AAV5 capsid protein sequences with the amino acid sequences of capsid proteins from the non-sialic acid-binding AAVs: AAV2, AAV7, AAV8, and AAV9. From the alignment, it can be determined that the capsid proteins from non-sialic acid-binding AAVS contain, as a group, the following amino acids in positions corresponding to 587 of the AAV5 capsid protein: asparagine (AAV7 and AAV9), serine (AAV8) and threonine (AAV2). Thus, these three amino acids could not be used to replace the leucine at position 587 in the AAV5 capsid protein. Amino acids that could be used are alanine, cysteines, aspartic acid, glutamic acid, phenylalanine, glycine, histidine, isoleucine, lysine, methionine, proline, glutamine, arginine, valine, tryptophan and tyrosine.

In one embodiment, a modified AAV capsid protein of the present invention comprises an amino acid sequence at least 80% identical, at least 85% identical, at least 90% identical, at least 95% identical or at least 97% identical to the amino acid sequence of a wt AAV capsid protein, wherein the modified capsid protein comprises at least one alteration at a location known to interact with a cell receptor. In one embodiment, a modified AAV capsid protein of the present invention comprises an amino acid sequence at least 80% identical, at least 85% identical, at least 90% identical, at least 95% identical or at least 97% identical to the amino acid sequence of a wt AAV capsid protein, wherein the modified capsid protein has at least one intentional alteration at a location known to interact with sialic acid. In one embodiment, a modified AAV capsid protein of the present invention comprises an amino acid sequence at least 80% identical, at least 85% identical, at least 90% identical, at least 95% identical or at least 97% identical to the amino acid sequence of a wt AAV capsid protein, wherein the modified capsid protein has at least one intentional alteration in the A-site or the B-site. In one embodiment, a modified AAV capsid protein of the present invention comprises an amino acid sequence at least 80% identical, at least 85% identical, at least 90% identical, at least 95% identical or at least 97% identical to the amino acid sequence of a wt AAV capsid protein, wherein the modified capsid protein comprises at least one intentional alteration at a location corresponding to a location in the AAV5 capsid protein selected from the group consisting of R277, H279, S280, E350, G351, C352, L353, P354, Q359, F361, T362, P553, F650, S651, D652, F529, N530, S531, L548, Q604, T711 and loop VII. In one embodiment, a modified AAV capsid protein of the present invention comprises an amino acid sequence at least 80% identical, at least 85% identical, at least 90% identical, at least 95% identical or at least 97% identical to the amino acid sequence of a wt AAV1, AAV4, AAV5 or AAV6 capsid protein, wherein the modified capsid protein has at least one intentional alteration at a location corresponding to a location in the AAV5 capsid protein selected from the group consisting of R277, H279, S280, E350, G351, C352, L353, P354, Q359, F361, T362, P553, F650, S651, D652, F529, N530, S531, L548, Q604, T711 and loop VII. In one embodiment, a modified capsid protein of the present invention comprises an amino acid sequence at least 80% identical, at least 85% identical, at least 90% identical, at least 95% identical or at least 97% identical to SEQ ID NO:1, SEQ ID NO:5, SEQ ID NO: 6 or SEQ ID NO:7, wherein the modified capsid protein comprises at least one non-native amino acid at a location corresponding to a location in the AAV5 capsid protein selected from the group consisting of R277, H279, S280, E350, G351, C352, L353, P354, Q359, F361, T362, P553, F650, S651, D652, F529, N530, S531, L548, Q604, T711 and loop VII. In one embodiment, a modified capsid protein of the present invention comprises an amino acid sequence at least 80% identical, at least 85% identical, at least 90% identical, at least 95% identical or at least 97% identical to a sequence selected from the group consisting of SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41 and SEQ ID NO:44, wherein the modified capsid protein has a non-native amino acid in at least one location corresponding to a location in the AAV5 capsid protein selected from the group consisting of R277, H279, S280, E350, G351, C352, L353, P354, Q359, F361, T362, P553, F650, S651, D652, F529, N530, S531, L548, Q604, T711 and loop VII. In one embodiment, a modified capsid protein of the present invention comprises an amino acid sequence selected from the group consisting of SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41 and SEQ ID NO:44.

Modified capsid proteins of the present invention are encoded by nucleic acid molecules of the present invention. In addition, modified capsid proteins are expressed by nucleic acid constructs of the present invention. Thus, such nucleic acid molecules and sequences are useful for producing modified AAV virions, as described below. Nucleic acid molecules include, but are not limited to, nucleic acid vectors and nucleic acid expression vectors (both of which can be referred to as nucleic acid constructs). As used herein, a nucleic acid vector refers to a nucleic acid molecule comprising a nucleic acid molecule of the present invention, such as a nucleic acid molecule encoding a wt or modified AAV capsid protein. Such vectors are useful for producing, for example, ORFs encoding capsid proteins of the present invention. A recombinant expression vector refers to a nucleic acid molecule encoding a protein, wherein the nucleic acid molecule can express the encoded protein. Examples of both such vectors include plasmids, nucleic acid viral vectors and viral genomes (including both DNA and RNA genomes). Such vectors can be used to transport the nucleic acid molecules of the invention into a cell within an environment, such as, but not limited to, an organism, tissue, or cell culture. Nucleic acid construct of the present disclosure are produced by the hand of man. A nucleic acid molecule of the present invention can be DNA, RNA or variants thereof. Methods for the construction of nucleic acid constructs of the present disclosure are well known. See, for example, *Molecular Cloning: a Laboratory Manual*, 3rd edition, Sambrook et al. 2001 Cold Spring Harbor Laboratory Press, and *Current Protocols in Molecular Biology*, Ausubel et al. eds., John Wiley & Sons, 1994.

In one embodiment, a nucleic acid molecule of the present invention comprises a nucleic acid sequence encoding a modified AAV capsid protein of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. It is to be appreciated that a nucleic acid construct can comprise one nucleic acid molecule or more than one nucleic acid molecule. It is also to be appreciated that a nucleic acid molecule can encode one protein or more than one protein.

Preferred nucleic acid molecules are those that encode a modified AAV capsid protein of the present invention. Thus, one embodiment of the present invention is a nucleic acid molecule comprising a nucleic acid sequence encoding a modified AAV capsid protein comprising at least one non-native amino acid residue in an amino acid sequence known to be involved in binding of the capsid protein to a cell receptor. In one embodiment, a nucleic acid molecule of the invention comprises a nucleic acid sequence encoding one or more of AAV capsid proteins, wherein the nucleic acid sequence has been altered such that the one or more encoded AAV capsid protein(s) comprise 1, 2, 3, 4, 5, 6, 7, 8, 9, 10, or more sequence alterations. Such sequence alterations include insertion mutations, deletion mutations and substitution. A preferred alteration to make is a substitution mutation. Thus, in one embodiment, a nucleic acid molecule of the invention comprises a nucleic acid sequence encoding one or more AAAV capsid proteins, wherein the nucleic acid sequence has been altered such that the encoded one or more AAV capsid proteins comprise 1, 2, 3, 4, 5, 6, 7, 8, 9, 10, or more amino acid substitutions compared to a native AAV capsid protein.

In one embodiment, a nucleic acid molecule of the present inventions comprises a nucleic aid sequence encoding a modified AAV capsid protein of the present invention comprising an amino acid sequence at least 80% identical, at least 85% identical, at least 90% identical, at least 95% identical or at least 97% identical to the amino acid sequence of a wt AAV capsid protein, wherein the modified capsid protein comprises at least one intentional alteration at a location known to interact with a cell receptor. In one embodiment, a nucleic acid molecule of the present invention comprises a nucleic aid sequence encoding a modified AAV capsid protein of the present invention comprising an amino acid sequence at least 80% identical, at least 85% identical, at least 90% identical, at least 95% identical or at least 97% identical to the amino acid sequence of a wt AAV capsid protein, wherein the modified capsid protein comprises at least one intentional alteration at a location known to interact with sialic acid. In one embodiment, a nucleic acid molecule of the present inventions comprises a nucleic aid sequence encoding a modified AAV capsid protein of the present invention comprising an amino acid sequence at least 80% identical, at least 85% identical, at least 90% identical, at least 95% identical or at least 97% identical to the amino acid sequence of a wt AAV capsid protein, wherein the modified capsid protein comprises at least one intentional alteration in the A-site or the B-site. In one embodiment, a nucleic acid molecule of the present inventions comprises a nucleic aid sequence encoding a modified AAV capsid protein of the present invention comprising an amino acid sequence at least 80% identical, at least 85% identical, at least 90% identical, at least 95% identical or at least 97% identical to the amino acid sequence of a wt AAV capsid protein, wherein the modified capsid protein comprises at least one intentional alteration in a location corresponding to a location in an AAV5 capsid protein selected from the group consisting of R277, H279, S280, E350, G351, C352, L353, P354, Q359, F361, T362, P553, F650, S651, D652, F529, N530, S531, L548, Q604, T711 and loop VII. In one embodiment, a nucleic acid molecule of the present inventions comprises a nucleic aid sequence encoding a modified AAV capsid protein of the present invention comprising an amino acid sequence at least 80% identical, at least 85% identical, at least 90% identical, at least 95% identical or at least 97% identical to the amino acid sequence of a wt AAV capsid protein, wherein the modified capsid protein comprises at least one alteration in a location corresponding to a location in the AAV5 capsid protein selected from the group consisting of R277, H279, S280, E350, G351, C352, L353, P354, Q359, F361, T362, P553, F650, S651, D652, F529, N530, S531, L548, Q604, T711 and loop VII. In one embodiment, a nucleic acid molecule of the present inventions comprises a nucleic aid sequence encoding a modified capsid protein of the present invention comprises an amino acid sequence at least 80% identical, at least 85% identical, at least 90% identical, at least 95% identical or at least 97% identical to SEQ ID NO:1, SEQ ID NO:5, SEQ ID NO: 6 or SEQ ID NO:7, wherein the modified capsid protein comprises at least one intentional alteration in a location corresponding to a location in the AAV5 capsid protein selected from the group consisting of R277, H279, S280, E350, G351, C352, L353, P354, Q359, F361, T362, P553, F650, S651, D652, F529, N530, S531, L548, Q604, T711 and loop VII. In one embodiment, a nucleic acid molecule of the present inventions comprises a nucleic aid sequence encoding a modified capsid protein of the present invention comprising an amino acid sequence at least 80% identical, at least 85% identical, at least 90% identical, at least 95% identical or at least 97% identical to a sequence selected from the group consisting of SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41 and SEQ ID NO:44, wherein the variations in the amino acid sequence are at locations other than the location which was altered. In one embodiment, a nucleic acid molecule of the present inventions comprises a nucleic aid sequence encoding a modified capsid protein of the present invention comprising an amino acid sequence selected from the group consisting of SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41 and SEQ ID NO:44.

One embodiment of the present invention is a nucleic acid molecule at least 90% identical, at least 95% identical, or at least 97% identical to a sequence selected from the group consisting of SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40 and SEQ ID NO:43, wherein the variations in nucleotide sequence are in locations other than the codons encoding amino acids at locations being altered. One embodiment of the present invention is a nucleic acid molecule comprising a nucleic acid sequence at least 90% identical, at least 95% identical, or at least 97% identical to a sequence selected from the group consisting of SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40 and SEQ ID NO:43. One embodiment of the present invention is a nucleic acid molecule comprising a nucleic acid sequence selected from the group consisting of SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40 and SEQ ID NO:43.

The present invention also encompasses expression systems for producing modified AAV capsid proteins of the present invention. In one embodiment, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a recombinant cell comprising a nucleic acid molecule of the present invention. One embodiment of the present invention is a recombinant virus comprising a nucleic acid molecule of the present invention.

As discussed above, the inventors have discovered that altering the amino acid sequence at specific locations of an AAV capsid protein can alter the properties of the capsid protein. Further, by virtue of possessing one or more modified capsid proteins of the present invention, AAV virions exhibit altered properties compared to the properties of an AAV virion possessing capsid proteins lacking the herein described modifications (e.g., wt AAV virions). According to the present invention, AAV virions, AAV viruses, AAV capsids, and the like, can be used interchangeably, although in some instances AAV capsids may refer to capsids that lack genetic material. Moreover, AAV virions comprising modified AAV capsid proteins of the invention are referred to as modified AAV (mAAV) virions. The present invention encompasses modified AAV virions comprising one or more modified capsid proteins of the present invention. That is, a modified AAV virion can comprise modified capsid proteins from single type of AVV (e.g., AAV5) or more than one type of AAV (e.g., AAV 4 and AAV5).

As noted previously, modified AAV virions of the invention have altered properties, such as, for example, increased or decreased cell transduction efficiency, altered receptor binding, altered affinity for a cell type, reduced immunogenicity and reduced binding by neutralizing antibodies. The properties of modified AAV virions of the present invention are compared to a corresponding parental AAV. As used herein, a parental AAV refers to an AAV comprising capsid proteins of the same type of AAV (e.g., AAV4) used to produce the modified AAV capsid protein. For example, the properties of a modified AAV comprising a modified AAV5 capsid protein would be compared to an AAV having a wt, or native, AAV5 capsid protein.

As used herein, transduction efficiency refers to the number of AAV virions being delivered to the cytoplasm of a cell compared to a control virus, such as, for example, a wild-type virus of the same AAV type (e.g., AAV5). Thus, an AAV virion having increased transduction efficiency is able to deliver a larger number of virions to the cytoplasm of a cell compared to a control virus, such as a wild-type AAV. One skilled in the art will understand that AAVs having a higher transduction will result in a larger number of molecules such viruses are carrying (e.g., heterogeneous protein or nucleic acid molecule). In one embodiment, a modified AAV virion of the invention has a transduction efficiency at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500% greater than the transduction efficiency of a parental AAV virion. In one embodiment, a modified AAV virion of the invention has a transduction efficiency at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, higher than the transduction efficiency of a parental AAV. In one embodiment, a modified AAV virion of the invention has a transduction efficiency at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500% less than the transduction efficiency of a parental AAV. In one embodiment, a modified AAV virion of the invention has a transduction efficiency at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, lower than the transduction efficiency of a parental AAV. The increased or decreased transduction efficiency can be in cells in culture and/or in vivo (e.g., in a body).

Modified AAV virions of the invention can also have altered affinity i.e., increased or decreased) for receptors present on the surface of cells. As used herein, affinity refers to the strength of the binding interaction between a capsid protein, modified capsid protein, AAV virion or modified AAV and another molecule such as, for example, a cell receptor or a carbohydrate molecule. Thus, modified capsid proteins and modified AAV virions can have increased or decreased affinity for specific cellular receptors. Methods of determining binding affinity are known to those skilled in the art. Moreover, because different parts of cellular receptors interact with different amino acid residues in the capsid protein, different alterations to the sequence may affect some receptor interactions but not others. Thus, alterations to the sequence may alter the preference of a capsid protein for a receptor. That is, modified capsid proteins, and modified AAV virions, may preferentially bind a receptor other than the receptor preferentially bound by the parental capsid protein or AAV virion. As used herein, preferential binding of a receptor means the capsid protein, of AAV virion, including n=modified versions thereof), bind a receptor with an affinity that is higher than the affinity of the capsid protein, or AAV virion, to a different receptor. In one embodiment, the affinity of a modified AAV virion of the invention for a specific type of receptor is increased by at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500%, compared to the affinity of a parental AAV virion for the same type of receptor. In one embodiment, the affinity of a modified AAV virion of the invention for a specific type of receptor is at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, higher than the affinity of a parental AAV for the same type of receptor. In one embodiment, the affinity of a modified AAV virion of the invention for a specific type of receptor is decreased by at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500%, compared to the affinity of a parental AAV virion for the same type of receptor. In one embodiment, the affinity of a modified AAV virion of the invention for a specific type of receptor is at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, lower than the affinity of a parental AAV for the same type of receptor.

As has been discussed, binding of AAV virions to cellular receptors is known to involve carbohydrates present on cellular receptors. Thus, in one embodiment, a modified AAV virion of the invention has an altered carbohydrate affinity. In one embodiment, the affinity of a modified AAV virion of the invention for a specific type of carbohydrate is increased by at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500%, compared to the affinity of a parental AAV virion for the same type of carbohydrate. In one embodiment, the affinity of a modified AAV virion of the invention for a specific type of carbohydrate is at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, higher than the affinity of a parental AAV for the same type of carbohydrate. In one embodiment, the affinity of a modified AAV virion of the invention for a specific type of carbohydrate is decreased by at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500%, compared to the affinity of a parental AAV virion for the same type of carbohydrate. In one embodiment, the affinity of a modified AAV virion of the invention for a specific type of carbohydrate is at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, lower than the affinity of a parental AAV for the same type of carbohydrate.

A specific type of carbohydrate used by some AAVS is sialic acid. In various embodiments, alterations of the capsid sequence can alter the affinity of a modified capsid protein, or a modified AAV, for sialic acid. In one embodiment, the affinity of a modified AAV virion of the invention for a specific sialic acid is increased by at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500%, compared to the affinity of a parental AAV virion for the same type of sialic acid. In one embodiment, the affinity of a modified AAV virion of the invention for a specific sialic acid is at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, higher than the affinity of a parental AAV for the same type of sialic acid. In one embodiment, the affinity of a modified AAV virion of the invention for a specific sialic acid is decreased by at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500%, compared to the affinity of a parental AAV virion for the same type of sialic acid. In one embodiment, the affinity of a modified AAV virion of the invention for a specific sialic acid is at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, lower than the affinity of a parental AAV for the same type of sialic acid.

Because the expression of receptors may be more abundant, or be increased or decreased, on specific cell types, modified AAVs can have altered affinity for specific types of cells. For example, a modified AAV virion can have an increased or decreased specificity for cells. Examples of such cells include, but are not limited to, lung cells, liver cells, brain cells, capillary epithelial cells, salivary gland cells, muscle cells, cells of the eye including retinal pigment epithelium cells, and tumor cells. In one embodiment, the affinity of a modified AAV virion of the invention for a specific type of cell is increased by at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500%, compared to the affinity of a parental AAV virion for the same type of cell. In one embodiment, the affinity of a modified AAV virion of the invention for a specific type of cell is increased by at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, higher than the transduction efficiency of a parental AAV for the same type of cell. In one embodiment, the affinity of a modified AAV virion of the invention for a specific type of cell is increased by at least 30%, at least 35%, at least 40%, at least about 45%, at least 50%, at least 60%, at least 70%, at least 80%, at least 90%, at least 100%, at least 125%, at least 150%, at least 175% at least 200%, at least 250%, at least 300%, at least 350%, at least 400% or at least 500%, compared to the affinity of a parental AAV virion for the same type of cell. In one embodiment, the affinity of a modified AAV virion of the invention for a specific type of cell is increased by at least 2-fold, at least 2.5-fold, at least 3-fold, at least 3.5-fold, at least 4-fold, at least 5-fold, at least 10-fold, at least 15-fold, at least 50 fold, at least 75-fold, or at least 100-fold or more, lower than the transduction efficiency of a parental AAV for the same type of cell. In one embodiment, the cell type is selected from the group consisting of lung cells, liver cells, brain cells, capillary endothelial cells, salivary gland cells, muscle cells, cells of the eye, and tumor cells. Exemplary cell types from these tissues include hepatocytes, kupffer cells, and endothelial cells in the liver; neurons, astrocytes, oligodendrocytes, and microglia in the CNS; macrophages, epithelial, alveolar and bronchial ductal cells in the lung; and retinal pigment epithelium cells in the eye.

The inventors have also discovered that alteration of the capsid protein of an AAV alters the antigenic profile of the virus. Specifically, mutations at particular locations in the virus capsid results in a modified AAV having an increased resistance to neutralizing antibody compared to the ability of a parental virus to be neutralized by the same antibody. In one embodiment, a modified AAV of the invention has at least a 2-fold, at least a 3-fold, at least a 4-fold, at least a 5-fold, at least a 6-fold, at least an 8-fold, at least a 10-fold, at least a 20-fold, at least a 50-fold, at least a 100-fold, at least a 500-fold, or at least a 1000-fold greater resistance to neutralization compared to a parental AAV (or wt AAV). For example, according to the present invention, a 2-fold higher resistance to neutralization refers to a virus that is able to infect, or transduce, a cell at twice the level of a parental, or wt, virus, when the both viruses are incubated with the same amount of the same neutralizing antibody. Methods of measuring neutralization are known to those skilled in the art and are also disclosed herein.

Due to their unique properties, modified AAVs of the invention are useful for practicing gene therapy (i.e., delivery of heterologous nucleic acid molecules to a cell.) For example, modified AAVs can carry AAV nucleic acid vectors of the invention. As has been described, such molecules comprise all the required cis-acting molecules necessary for packaging of the AAV nucleic acid vector. Thus, any heterologous nucleic acid molecules associated with the AAV nucleic acid vector will also be packaged. Thus, one embodiment of the present invention is a modified AAV virion comprising an AAV nucleic acid vector. One embodiment of the present invention is a modified AAV virion comprising a heterologous nucleic acid molecule. As used herein, heterologous nucleic acid molecules are nucleic acid molecules from an organism unrelated to AAVs. Those skilled in the art are able to determine if an organism is unrelated to an AAV. One embodiment of the present invention is a modified AAV virion comprising an AAV nucleic acid vector that comprises a heterologous nucleic acid molecule. In one embodiment, the heterologous nucleic acid is operably linked to a promoter. The heterologous nucleic acid molecule can be any nucleic acid molecule capable of achieving a desired purpose for which the nucleic acid constructs and modified AAV are being designed. For example, the heterologous nucleic acid molecule can encode a therapeutic agent. As used herein, a therapeutic agent is a molecule (e.g., protein), the intended use of which is to treat or eliminate a disease or condition in an individual. For example, a mAAV of the present invention comprising an AAV nucleic acid vector encoding a therapeutic agent can be used for treating a condition arising from a missing or mutated gene. In an alternative example, a mAAV of the present invention comprising an AAV nucleic acid vector encoding a therapeutic agent can be used for treating cancer. One example of a therapeutic agent is functional copy of a protein to be delivered to an individual lacking functional copies of the protein. Examples of such proteins include, but are not limited to, immunoregulatory proteins (e.g., cytokines), transcription factors, structural proteins (e.g., sodium channels), hormones, suicide molecules (e.g., ricin) and the like. Therapeutic agents include therapeutic RNAs such as, for example, anti-sense RNA, siRNA, RNAi, and the like.

The present invention also encompasses methods of making modified AAVs of the invention. One embodiment of the present invention is a method of producing a mAAV of the invention, the method comprising providing to a cell: (a) an AAV nucleic acid vector comprising at least one ITR sequence, and (b) AAV sequences sufficient for replication of the nucleic acid template and encapsidation into modified AAV capsids (e.g., AAV rep sequences and AAV cap sequences encoding the AAV Rep and capsid proteins). In one embodiment, the AAV nucleic acid vector further comprises at least one heterologous nucleic acid sequence. In particular embodiments, the AAV nucleic acid vector comprises two AAV ITR sequences, which are located 5' and 3' to the heterologous nucleic acid sequence (if present), although they need not be directly contiguous thereto. The AAV nucleic acid vector and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells. The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus. e.g., 293 cells or other E1a trans-complementing cells.

The AAV replication and capsid sequences may be provided by any method known in the art. Current protocols typically express the AAV rep/cap genes on a single plasmid. However, the AAV replication and packaging sequences need not be provided together, although it may be convenient to do so. The AAV rep and/or cap sequences may be provided by any viral or non-viral vector. As a further alternative, the rep/cap sequences may be stab incorporated into a cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al. (1997) *Nature Med.* 3:1295; and U.S. Pat. Nos. 6,040,183 and 6,093,570. Further, the helper virus functions may be provided by a packaging cell with the helper sequences embedded in the chromosome or maintained as a stable extrachromosomal element. Those skilled in the art will appreciate that it may be advantageous to provide the AAV replication and capsid sequences and the helper virus sequences (e.g., adenovirus sequences) on a single helper construct. This helper construct may be a non-viral or viral construct. As a further alternative, the virus vectors of the invention can be produced in insect cells using baculovirus vectors to deliver the rep/cap genes and rAAV template as described, for example, in Urabe et al. (2002) *Human Gene Therapy* 13:1935-43.

As noted, mAAV virions of the invention are useful for treating conditions or diseases. Thus, one embodiment of the invention is a method to treat a patient for a disease or condition, the method comprising administering to the patient a mAAV of this invention, wherein the mAAV comprises a heterologous nucleic acid molecule encoding a therapeutic agent for treating the disease or condition. In certain embodiments of the inventive treatment methods, administration of the AAV constructs of this invention proceeds via any one of a variety of routes, including intravenous (IV), intramuscular (IM), intra-arterial, intramedullary, intrathecal, subcutaneous (SQ), intraventricular, transdermal, interdermal, intradermal, by intratracheal instillation, bronchial instillation, and/or inhalation; as a nasal spray, and/or as an aerosol. In certain embodiments, intravenous injection, or infusion directly to a specifically targeted tissue may be used. Any appropriate site of administration may be used. For example, the inventive composition may be administered locally and directly at the site where action is required or may be attached or otherwise associated, e.g. conjugated, with entities, which will facilitate the targeting to an appropriate location in the body. Specific delivery routes include intravitreal injection, and/or subretinal injection to the eye; aerosol delivery of the AAV vectors to the lung; oral gavage; portal vein, peripheral vein, superficial temporal vein, hepatic infusion, and/or intrahepatic injection to the liver.

One embodiment of the invention is a composition comprising a mAAV of the present embodiments. Such compositions can also include an aqueous solution, such as a physiologically compatible buffer. Examples of excipients include water, saline, Ringer's solution, and other aqueous physiologically balanced salt solutions. In some embodiments, excipients are added to, for example, maintain particle stability or to prevent aggregation. Examples of such excipients include, but are not limited to, magnesium to maintain particle stability, pluronic acid to reduce sticking, mannitol to reduce aggregation, and the like, known to those skilled in the art.

A composition of the embodiments is conveniently formulated in a form suitable for administration to a subject. Techniques to formulate such compositions are known to those skilled in the art. For example, a mAAV virion of the embodiments can be combined with saline or other pharmaceutically acceptable solution; in some embodiments excipients are also added. In another embodiment, a composition comprising a mAAV virion is dried, and a saline solution or other pharmaceutically acceptable solution can be added to the composition prior to administration.

One embodiment of the invention is a kit for practicing embodiments of the present invention. Kits of the present invention can comprise any reagent necessary to produce and use mAAV virions of the present invention. Thus, kits can comprise, for example, nucleic acid molecules, proteins and/or mAAVS of the present invention. Kits can an also include, for example, tubes, buffers, instructions for use, etc.

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1: Mutagenesis of the Sialic Acid Binding Regions of AAV5 Results in Elimination or Alteration in Sialic Acid-Dependent Transduction As a genus, the dependoviruses use a diverse group of cell surface carbohydrates for attachment and entry. Despite the fact that a majority of adeno-associated viruses (AAVs) utilize sialic acid (SIA) for binding and transduction, this virus-carbohydrate interaction is poorly understood. Utilizing X-ray crystallography, two SIA binding regions were mapped for AAV5. The first site mapped to the depression in the center of the 3-fold axis of symmetry, while the second site was located under the βHI loop close to the 5-fold axis. Mutagenesis of amino acids 569 and 585 or 587 within the 3-fold depression resulted in elimination or alteration in SIA-dependent transduction, respectively. This change in SIA binding was confirmed using glycan microarrays. Mutagenesis of the second site identified a role in transduction that was SIA independent. Further studies of the mutants at the 3-fold site demonstrated a change in transduction activity and cell tropism in vivo as well as resistance to neutralization by a polyclonal antibody raised against the wild-type virus.

IMPORTANCE: Despite the fact that a majority of AAVs utilize sialic acid for binding and transduction, this virus-carbohydrate interaction is poorly understood. Utilizing X-ray crystallography, the sialic acid binding regions of AAV5 were identified and studied using a variety of approaches. Mutagenesis of this region resulted in elimination or alteration in sialic acid-dependent transduction in cell lines. This change in sialic acid glycan binding was confirmed using glycan arrays. Further study also demonstrated a change in transduction and activity and cell tropism in vivo as well as resistance to neutralization by antibodies raised against the wild-type virus.

MATERIALS AND METHODS: Cell cultures: African green monkey kidney COS cells (The American Type Culture Collection [ATCC], Manassas, Va.) and 293T cells (human embryonic kidney cells) were cultured in Dulbecco's modified Eagle's medium supplemented with 10% fetal bovine serum (FBS; HyClone, Logan, Utah), 2 mM l-glutamine, 100 U of penicillin/ml, and 0.1 mg of streptomycin/ml (Invitrogen, Carlsbad, Calif.). The human tumor cell lines IGROV-1 and SF-268 were maintained in RPMI 1640 medium (Biosource, Camarillo, Calif.) supplemented with 10% FBS and 2 mM l-glutamine (15). Cells were maintained at 37° C. under a 5% $CO_2$ humidified atmosphere. In the transduction and binding experiments, cells transduced with the recombinant AAVs were placed in medium supplemented with 5% FBS (HyClone).

Crystallographic analysis of the AAV5-SIA complex: The expression, purification, and crystallographic studies of AAV5 virus-like particles (VLPs) have been previously described (16). To study the interaction of AAV5 with SIA, crystals grown in 20 mM Tris-HCl (pH 7.5), 350 mM NaCl, 10 mM $MgCl_2$, and 1.5% polyethylene glycol (PEG) 8000 at room temperature (RT) using the hanging-drop vapor diffusion method were soaked with 1 mM SIA (Sigma) for about 48 h prior to X-ray diffraction data collection (17). Crystals were soaked for 30 sec in cryoprotectant solution consisting of the crystallization buffer with 10% PEG 8000 and 30% glycerol and flash cooled in liquid nitrogen vapor prior to X-ray diffraction data collection. A total of 199 diffraction images were collected from 4 crystals at two different synchrotron beam lines: F1 at the Cornell High Energy Synchrotron Source (CHESS, Cornell University, Ithaca, N.Y.) at a crystal-to-detector distance of 400 mm, oscillation angle of 0.3° per image, and exposure time of 45 s per image at a wavelength (λ) of 0.9799 Å; and X29 at the National Synchrotron Light Source (NSLS) at the Brookhaven National Laboratory with a crystal-to-detector distance of 400 mm, an oscillation angle of 0.3° per image, and an exposure time of 30 sec per image at a λ, of 1.10 Å.

The reflections were indexed and integrated with the HKL2000 suite of programs and scaled and merged with Scalepack (18). The crystals diffracted X-rays to 3.5-Å resolution, and the $R_{merge}$ and completeness for this data set were 14.9% and 59.4%, respectively. The data processing statistics are given in Table 1. The crystals belong to the orthorhombic space group $P2_12_12_1$ with unit cell dimensions as follows: a=264.7 Å, b=447.9 Å, and c=629.7 Å. This is isomorphous with the published AAV5 VLP structure (PDB accession no. 3NTT) (19). Thus, a difference map, $F_o$-$F_c$ (where $F_o$ and $F_c$ are the observed and calculated structure factor amplitudes, respectively), was calculated to localize the potential binding site for SIA using the CNS program (20).

TABLE 1

Data collection, processing, and refinement statistics of AAV5-SIA

| Parameter (unit) | AAV5-SIA[a] |
|---|---|
| Wavelength (λ, Å) | 0.9799 (CHESS)/1.10 (NSLS, BNL) |
| No. of films | 199 |
| Space group | P2$_1$2$_1$2$_1$ |
| Unit cell parameters (Å) | a = 264.7, b = 447.9, c = 629.7 |
| Resolution (Å) | 50.00-3.50 (3.63-3.50) |
| Total no. of reflections | 4,035,746 |
| No. of unique reflections | 551,907 (29,433) |
| R$_{merge}$[b] (%) | 14.9 (23.2) |
| Completeness (%) | 59.4 (31.9) |
| I/σ | 5.7 (2.2) |
| R$_{factor}$[c]/R$_{free}$[d] (%) | 21.6/21.8 |
| RMSD[e] of bonds (Å) and angles (°) | 0.009, 1.49 |

[a]Values in parentheses are for the highest-resolution shell.
[b]R$_{merge}$ = (Σ|I − <I>|/Σ <I>) × 100, where I is the intensity of an individual reflection with indices h, k, and l and <I> is the average intensity of all symmetry equivalent measurements of that reflection; the summation is over all intensities.
[c]R$_{factor}$ = (Σ|F$_o$| − |F$_c$|/Σ |F$_o$|) × 100, where F$_o$ and F$_c$ are the observed and calculated structure factor amplitudes, respectively.
[d]R$_{free}$ is calculated in the same way as R$_{factor}$, except that it uses 5% of the reflection data partitioned from the refinement process.
[e]RMSD, root mean square deviation.

The averaged F$_o$-F$_c$ electron density map, when contoured at a threshold of 2.0σ, revealed positive electron densities at the 3-fold axis and under the βHI loop, defined as sites A and B, respectively, which could be interpreted as an SIA molecule. To enable modeling and refinement of the SIA molecules, the coordinate files for SIA were obtained from the HIC-Up server (21) and the geometry restraints and dictionary files were generated using the phenix elbow subroutine in the Phenix program (22). The SIA molecules were docked into F$_o$-F$_c$ densities using interactive rigid-body rotations and translations in the Coot program (23). The fit of the docked molecules was refined against the F$_o$-F$_c$ difference map using the Real_Space refinement option in Coot. The amino acids constituting the SIA binding sites were predicted based on the list of amino acid residues with interactions within 3.6 Å of the docked SIA molecules. The figures were generated using the Pymol program (24).

Construction of mutant capsid plasmids: Mutations, predicted to abrogate A- and B-site SIA interactions by switching the AAV5 residue types (that differ to AAV2 at the structurally mapped sites) to those present at the structurally equivalent positions in AAV2, were introduced into the AAV5 capsid gene using QuikChange site-directed mutagenesis (Stratagene, San Diego, Calif.) per the manufacturer's instructions. For each AAV5 mutant, two complementary PCR primers were used to introduce changes into a pAAV5 RepCap plasmid (Table 2). The A-site mutants include M569V, Y585V, and L587T mutants. A double mutant was also made, Y585V/L587T mutant. The B-site mutants include D652F, T362M, Q359D, E350Q, P533S, P533G, and AAV5 Loop VII mutants, a VR-VII (19) substitution mutant. All mutations were confirmed by sequencing the final plasmid.

TABLE 2

Oligonucleotide primers used to make the different A-site and B-site AAV5 cap mutants

| Site and mutation(s) | Sense | Sequence (5' to 3') |
|---|---|---|
| A site | | |
| M569V | Forward | GTCGGCGGGCAGGTGGCCACCAACAAC |
|  | Reverse | GTTGTTGGTGGCCACCTGCCCGCCGAC |
| Y585V | Forward | GCGACCGGCACGGTCAACCTCCAGGAAATC |
|  | Reverse | GATTTCCTGGAGGTTGACCGTGCCGGTCGC |
| L587T | Forward | CCGGCACGTACAACACCCAGGAAATCGTGCCC |
|  | Reverse | GGGCACGATTTCCTGGGTGTTGTACGTGCCGG |
| Y585V/L587T | Forward | CGCGACCGGCACGGTCAACACCCAGGAAATCGTGCCC |
|  | Reverse | GGGCACGATTTCCTGGGTGTTGACCGTGCCGGTCGCG |
| B site | | |
| D652F | Forward | ACCAGCTTCTCGGCCGTGCCCGTCAGCAG |
|  | Reverse | TGCTGACGGGCACGGCCGAGAAGCTGGTG |
| T362M | Forward | CGTCCAAGTGTTTATGGACGACGACTACCAG |
|  | Reverse | TGGTAGTCGTCGTCCATAAACACTTGGACGG |
| Q359D | Forward | AACCTCACCTCCACCGTCGATGTGTTTACGGACGACGAC |
|  | Reverse | TCGTCGTCCGTAAACACATCGACGGTGGAGGTGAGGTTG |
| E350Q | Forward | GCAACGGGACCCAGGGATGCCTGC |
|  | Reverse | CAGGCATCCCTGGGTCCCGTTGCC |
| P533 S | Forward | TTCAACAGCCAGTCGGCGAACCCGGG |
|  | Reverse | CCGGGTTCGCCGACTGGCTGTTGAAG |
| P533G | Forward | ATCTTCAACAGCCAGGGGGCGAACCCGGGCAC |
|  | Reverse | TGCCCGGGTTCGCCCCCTGGCTGTTGAAGATC |
| AAV5 loop VII | Forward | GGAGAACACTATGATCTTCGGGAAGCAAGGCTCAGAGAAAAC AAATGTGGACATTGAAAAGGTCATGATCACCAGCGAGAGCGAG |
|  | Reverse | CTCGCTCTCGCTGGTGATCATGACCTTTTCAATGTCCACATTTGT TTTCTCTGAGCCTTGCTTCCCGAAGATCATAGTGTTCTCC |

Generation of recombinant virus: Wild-type AAV5 and capsid mutant vectors expressing a nuclear localized green fluorescent protein (GFP) were produced as previously described (25). Briefly, 293T cells were cotransfected with pAAV5-NLS-GFP, pAAV5 RepCap mutants, and the Ad helper plasmid 449B (26). Recombinant (rAAV-GFP) vectors were purified by CsCl gradient centrifugation. DNase-resistant genome copy numbers for the vectors were determined by quantitative real-time PCR using the TaqMan system (Applied Biosystems) with probes specific to the cytomegalovirus (CMV) promoter contained within the packaged genome.

Cellular transduction following digestion of cell surface SIA: Exponentially growing COS, IGROV-1, and SF-268 cells were plated at a density of $5 \times 10^3$ cells/well in a flat-bottom 96-well plate. Twenty-four hours after seeding, cells were incubated for 45 min with 1 mU of the broad-spectrum neuraminidase (NA) from *Vibrio cholerae* (Calbiochem, La Jolla, Calif.) or Glyko sialidase A (SA; recombinant from *Arthrobacter ureafaciens*; Prozyme, San Leandro, Calif.) to remove SIA. Cells were then washed with medium and transduced with $1 \times 10^9$ particles of rAAV-GFP vectors. GFP expression, which serves as a surrogate marker for transduction, was detected 42 h later with a fluorescent cell counter (BD FACSArray Bioanalyzer; BD Biosciences, San Jose, Calif.).

Cell surface vector binding assay: COS cells were seeded at $2 \times 10^4$ cells/well in a flat-bottom 96-well plate. Twenty-four hours after seeding, cells were incubated for 45 min with 1 mU of NA or SA and incubated for 45 min at 37° C. Cells were then chilled for 5 min at 4° C. and incubated for 30 min at 4° C. with $3 \times 10^9$ rAAV-GFP particles. After this incubation, cells were washed twice with cold medium, once with phosphate-buffered saline (PBS), and lysed in 50 µl buffer P1 from the Qiaprep Miniprep kit (Qiagen, Germany). Copy numbers of cell-associated vector genomes in the cell lysates were determined by quantitative real-time PCR using the TaqMan system (Applied Biosystems) with probes specific to the CMV promoter.

Antibody neutralization assay: COS cells were seeded at a density of $5 \times 10^3$ cells/well in a flat-bottom 96-well plate 1 day before infection with $2 \times 10^7$ rAAV-GFP vectors, which had been preincubated with serial dilutions of a polyclonal serum, raised against AAV5, in medium for 1 h at RT. Cells were incubated at 37° C. for 1 h and then washed with medium. Twenty-four hours after infection, cells were analyzed for GFP expression by flow cytometry (BD FACSArray Bioanalyzer).

Glycan microarray analysis of AAV5 glycan interactions: The glycan binding profiles for WT AAV5 VLPs and rAAV5-GFP particles were characterized using glycan microarrays produced by the Consortium for Functional Glycomics (CFG). (functionalglycomics.org/static/consortium/resources/resourcecoreh). The screening was conducted several times on different microarrays with different biological replicates (PA Ver 2 to Ver 4.1). The microarrays contained 262 to 371 sialylated and nonsialylated glycans with different linkages and modifications (functionalglycomics.org/glycomics/publicdata/selectedScreens.jsp).
Purified AAV5 VLPs or rAAV5-GFP (at a concentration of 100 to 200 µg/ml) used to probe the array was detected using the ADK5a anti-AAV5 capsid antibody and by goat anti-mouse secondary IgG with a fluorescein isothiocyanate (FITC) label; alternatively, VLPs were directly labeled with an Alexa Fluor 488 label for detection. A similar approach was used for profiling the glycan binding properties of two AAV5 SIA binding mutants, M569V and L587T mutants, following confirmation of reduced cell binding and infectivity phenotypes using binding and transduction assays. These mutants, produced in 293T cells, were screened on array PA v3.1 and detected with ADK5a and the Alexa Fluor 488 goat anti-mouse secondary antibody.

In vivo study of transgene expression: All mouse studies were conducted in an AAALAC-accredited facility under the Institutional Animal Care and Use Committee Protocol approval (NIDCR). Vector particles ($1 \times 10^{10}$) of WT AAV5 or L587T mutant vectors encoding luciferase were injected into male BALB/c mice (27) by three different routes, the submandibular salivary glands, the hind limb, or lungs ($1 \times 10^{11}$ viral particles). Transduction was visualized by photon imaging of the whole animal using a Xenogen camera (IVIS Lumina; PerkinElmer) at 7 months postinfection.

Figure 1C:
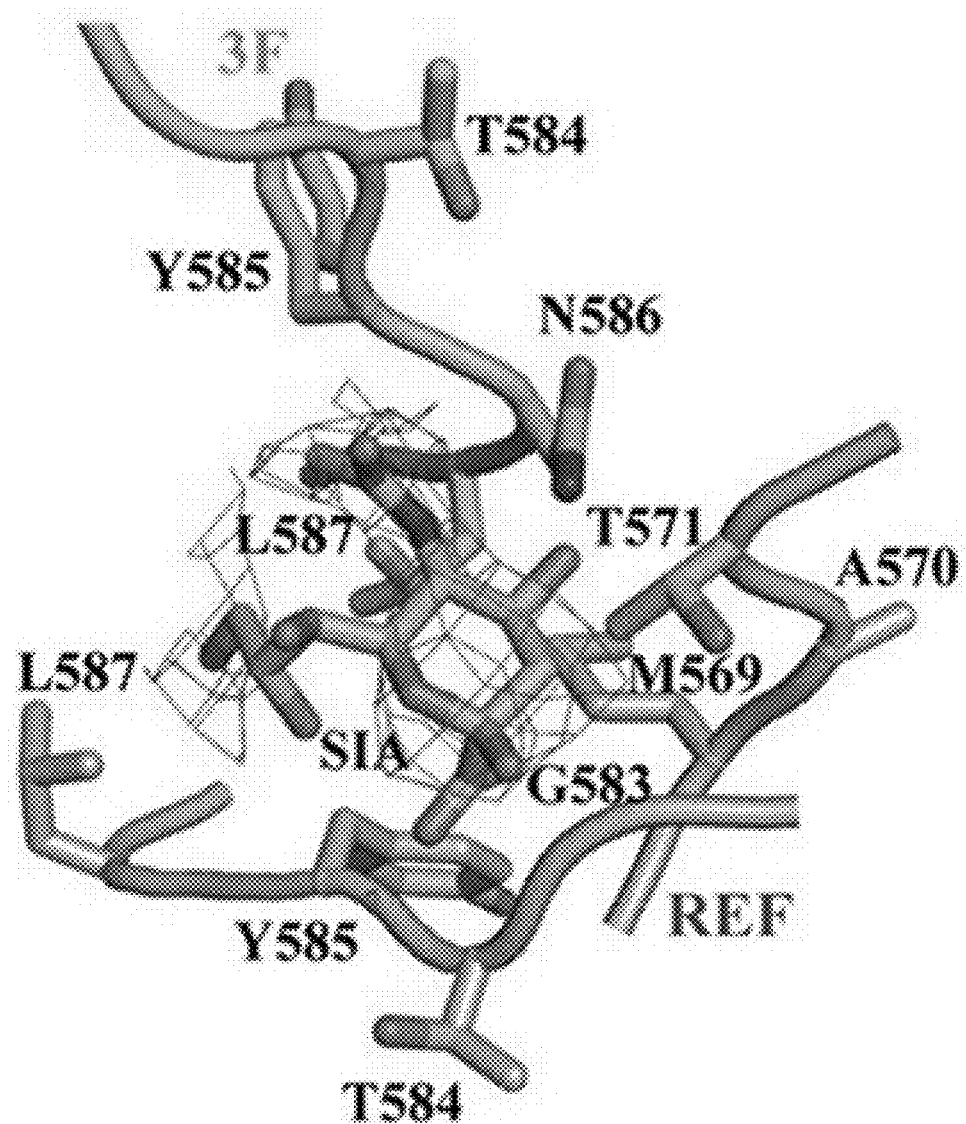
Figure 1D:
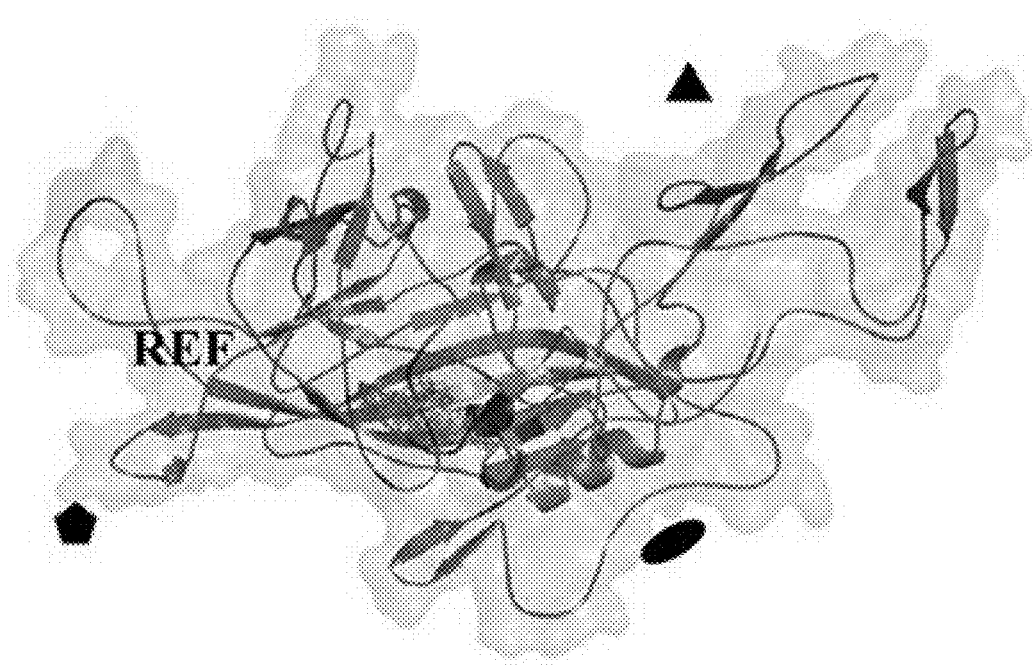
Figure 1E:
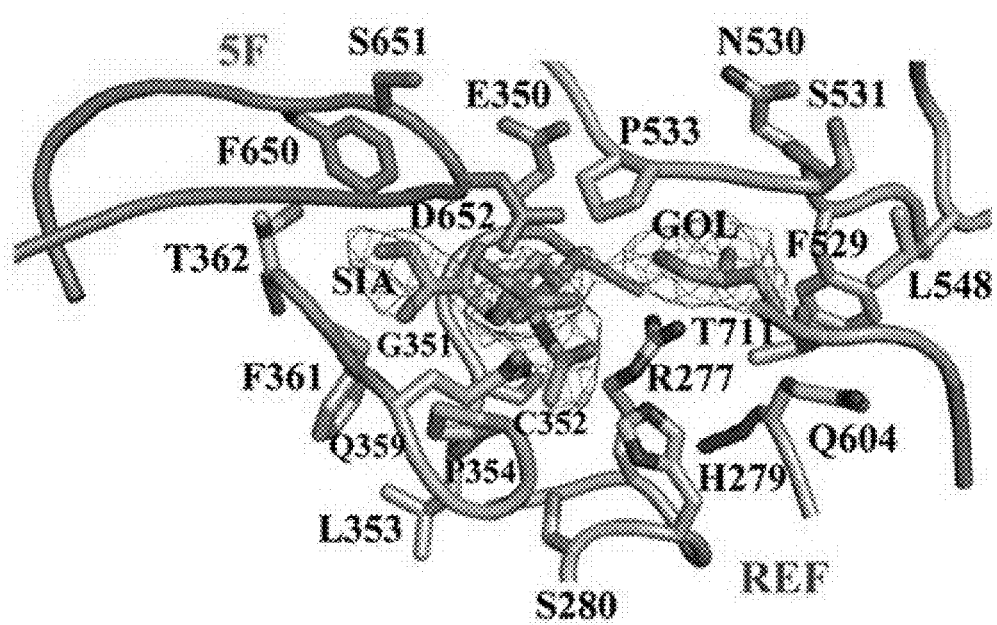

RESULTS: Structural studies of AAV5-SIA interactions: SIA was observed in two separate sites in AAV5 using an averaged $F_o$-$F_c$ difference density map contoured at a threshold of 2.0σ. The A site is located in the depression centered at the icosahedral 3-fold symmetry axis, and the B site is located under the HI loop, which sits above a 5-fold symmetry-related VP monomer and is also adjacent to the glycerol molecule (GOL) observed in the previously reported crystal structure of AAV5 (FIGS. 1A-1E) (19). An effort at crystallographic refinement of the AAV5 VP3-SIA complex structure resulted in a reduction in the density signal for the SIA N-acetamido and glycerol side groups, especially for the A-site molecule, so interpretation was limited to the real-space refined model inside the $F_o$-$F_c$ density. This observation suggests that the SIA might not interact with all the 60 copies of the VP in a similar manner or is flexible enough to adopt slightly different conformations at the 60 sites. These two possible scenarios would be inconsistent with the icosahedral symmetry imposed during the structure refinement and would lead to lack of ordering of the density for the SIA side groups. The amino acid residues that interact with SIA in the A site are M569, A570, T571, G583, T584, Y585, N586, and L587 (contact distance of 2.4 to 3.6 Å) (Table 3; FIG. 1C). The residues interacting with SIA in the B site are R277, H279, S280, E350, G351, C352, L353, P354, Q359, F361, T362, P553, F650, S651, and D652) (Table 3; FIG. 1E). The residues that interact with GOL in the B site are R277, F529, N530, S531, L548, Q604, and T711.

Figure 2A:
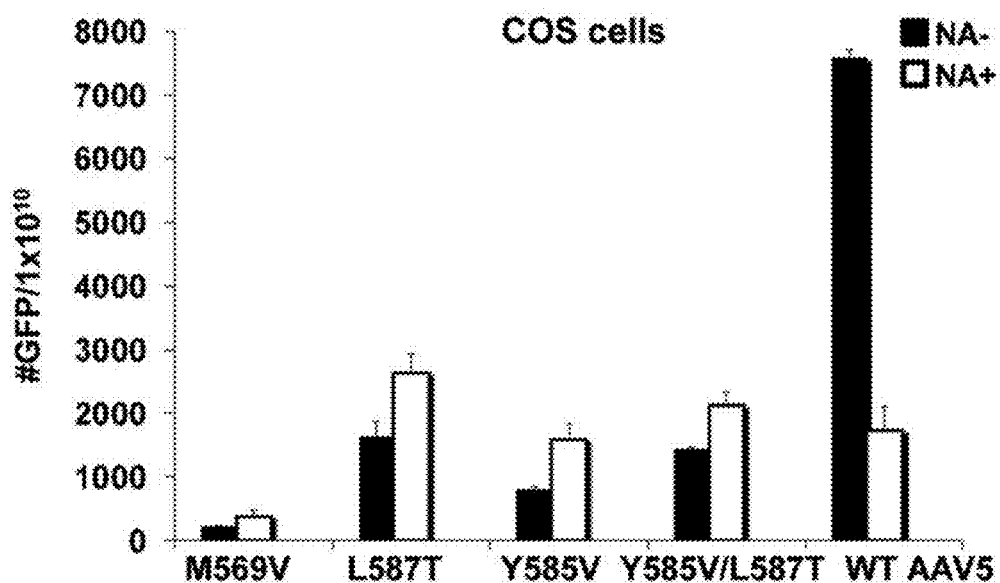
FIGS. 2A-2C demonstrate the transduction activity with AAV-5 A-site mutants. The transduction activity and the effect of neuraminidase were compared for mutation in the A-site using COS (FIG. 2A), SF-268 (FIG. 2B), and IGROV-1 (FIG. 2C) cells. Transduction was measured either with (NA+) or without (NA−) pretreatment with neuraminidase to enzymatically remove terminal cell surface SIA groups. The values are means from three experiments; the error bars represent standard deviations.
Figure 2B:
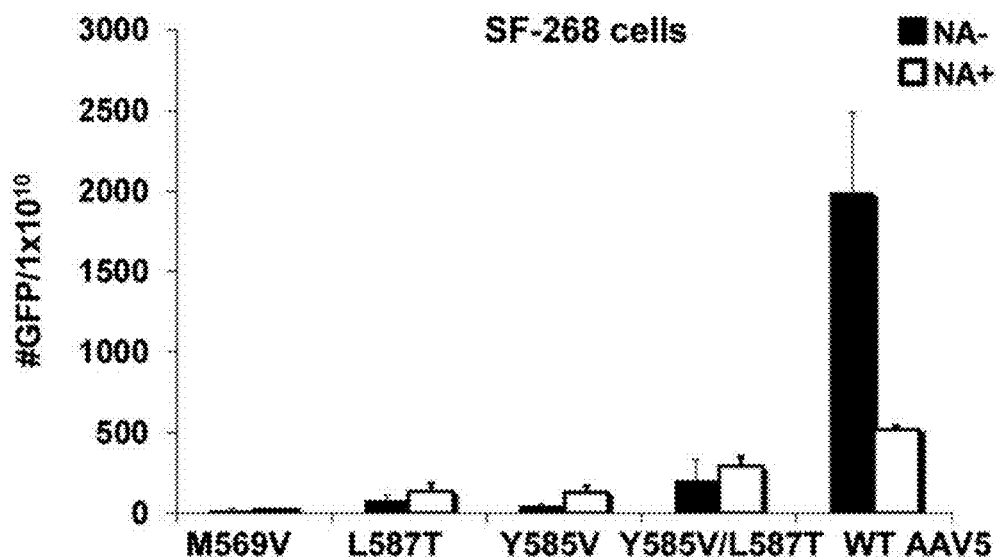
Figure 2C:
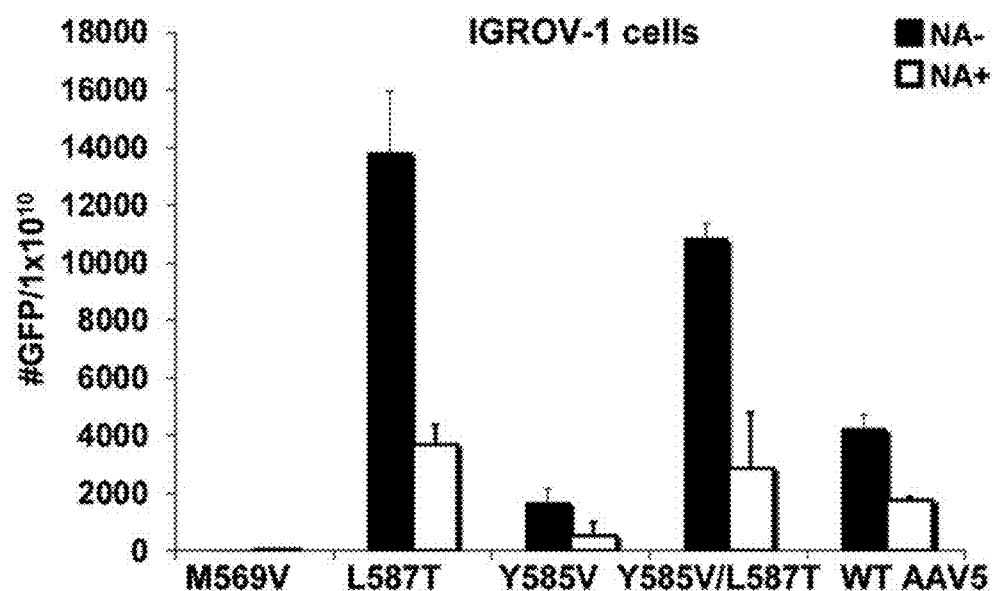

The A site but not the B site is important in SIA-dependent transduction: The biological significance of the A-site and B-site AAV5-SIA interactions was studied by making point mutations at AAV5 contact residues that differed with respect to AAV2 (a non-SIA-binding AAV) and have side chain interactions, and their transduction activity was tested. Very little difference in vector particle yields or physical properties was observed between preparations of WT AAV5 and the mutants (data not shown). All mutants were tested on three diverse cell lines, COS, SF-268, and IGROV-1. For the A-site mutants, in the COS cells, although transduction activity for the M569V mutant was almost completely abolished, L587T, Y585V, and Y585V/L587T mutants all showed approximately 7-fold-lower transduction activity than that of WT AAV5 (FIG. 2A). However, in contrast to WT AAV5, removal of cell surface SIA with NA did not further inhibit the transduction of L587T, Y585V, and Y585V/L587T mutants. Interestingly, all the mutants showed a slight increase in transduction following terminal SIA removal. Similar results were observed with the SF-268 cells (FIG. 2B). A different pattern of transduction was observed on the IGROV-1 cells. Although the M569V mutant displayed little transduction activity, similar to the observation in COS cells, the L587T mutation alone or in combination with Y585V improved transduction in an SIA-dependent manner compared to WT AAV5, with the WT virus transduction being lower than in COS cells (FIG. 2C). Compared with COS, L587T mutant transduction activity increased 3.5-fold on the IGROV-1 cells, while the Y585V/L587T double mutant showed an approx. 3-fold increase. Transduction activity of the Y585V mutant also increased on IGROV-1 cells compared to COS but was ~2-fold lower than for WT AAV5. To test if the transduction by the two variants was SIA dependent, cells were treated with neuraminidase and the change in transduction was compared with that of untreated cells. In contrast to the transduction activity on COS cells, L587T, Y585V, and Y585V/L587T mutants all exhibited neuraminidase-sensitive transduction activity.

Figure 3A:
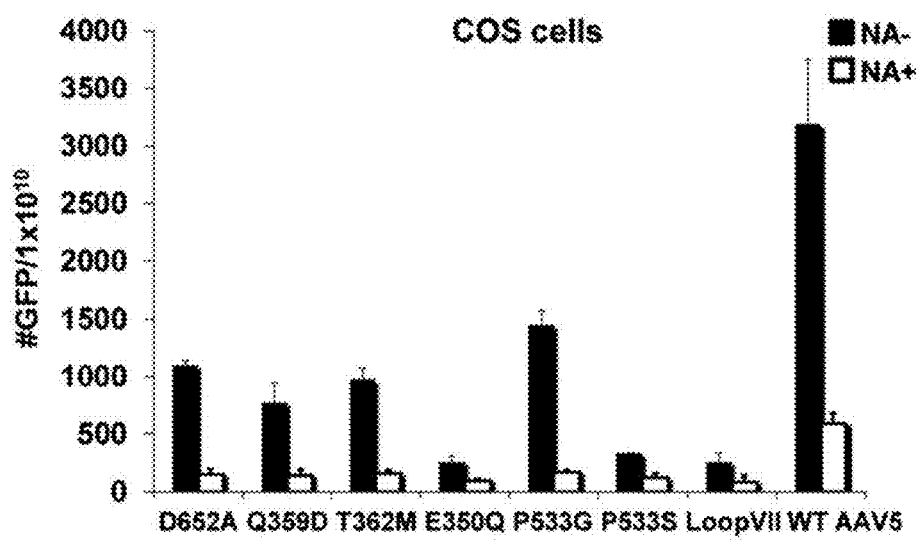
FIGS. 3A-3C demonstrate additional transduction activity with AAV-5 B-site mutants. The transduction activity and the effect of neuraminidase were compared for mutation in the B-site using COS (FIG. 3A), SF-268 (FIG. 3B), and IGROV-1 (FIG. 3C) cells. Transduction was measured either with (NA+) or without (NA−) pretreatment with neuraminidase to enzymatically remove terminal cell surface SIA groups. The values are means from three experiments; the error bars represent standard deviations.
Figure 3B:
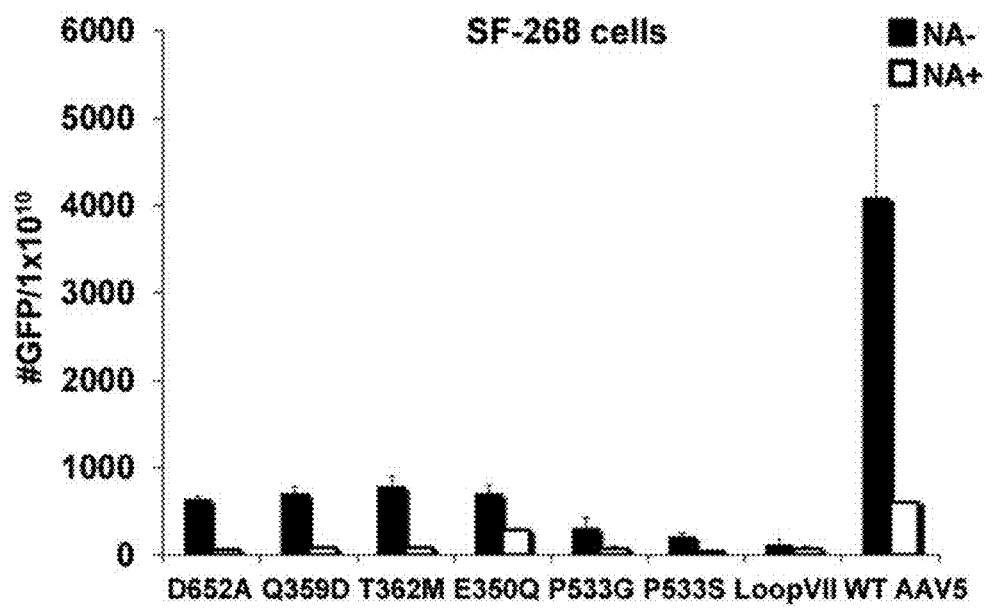
Figure 3C:
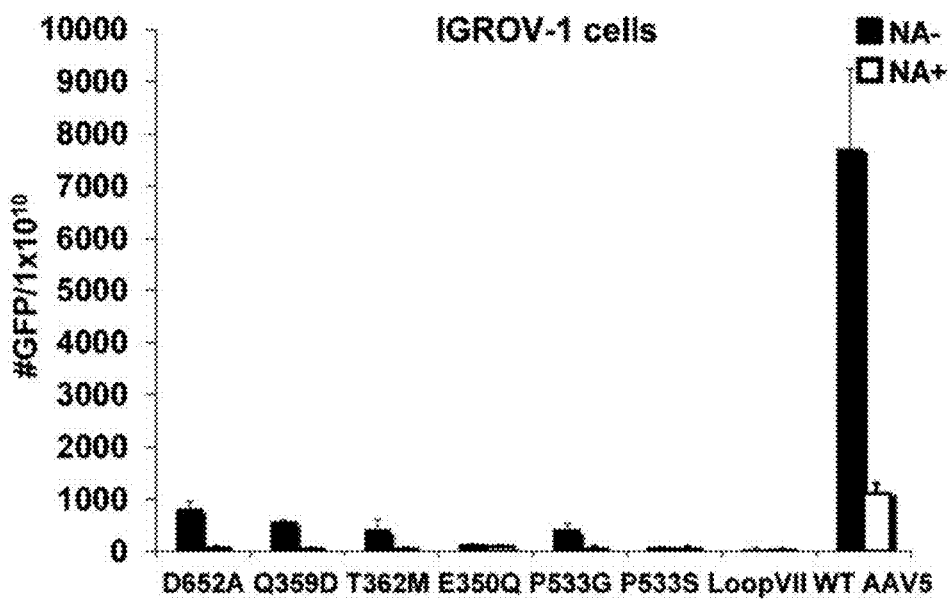

AAV5 transduction (FIGS. 3A-3C). For the Q359D and P533S mutations, there was a loss in GFP expression. Neuraminidase treatment diminished the number of transduced cells, similar to WT AAV5. However, in contrast to the A-site mutants, all of the B-site mutants displayed SIA-dependent transduction activity following neuraminidase treatment on all three target cells. There was an average 5-fold decrease in transduction on all cells following pretreatment with neuraminidase, which was similar to the fold decrease observed with WT AAV5. Transductions of SF-268 and IGROV-1 were lower than on COS cells but still displayed SIA-dependent transduction. These results suggest that while both the A-site and B-site regions are important in transduction, mutation of the A-site removes neuraminidase-sensitive transduction, suggesting that this region is critical to the binding of SIA that is necessary for virus attachment and transduction.

TABLE 3

SIA-VP interactions in AAV5 capsid[a]

| Amino acid residue for AAV serotype (receptor type)[b] | | | | | | A- or B-site or GOL interactions | | |
|---|---|---|---|---|---|---|---|---|
| 1 (SIA) | 2 (HS) | 3 (HS) | 4 (SIA) | 5 (SIA) | 6 (SIA/HS) | AAV5 VP1 atom | SIA or GOL atom[b] | VP monomer |
| | | | | | | A-site interactions | | |
| V | V | V | L | M[c] | V | M569 (CG) | O1B | REF |
| A | S | A | P | A | A | A570 (O) | O4 | |
| V | T | N | G | T | V | T571 (CG2) | C3 | |
| G | A | R | D | G | G | G583 (O) | O1B | |
| D | D | T | R | T | D | T584 (O) | O1A | |
| V | V | V | L | Y | V | Y585 (N) | O1A | |
| A | T | D | A | L | V | L587 (CD2) | O9 | |
| D | D | T | R | T | D | T584 (O) | O10 | 3F |
| V | V | V | L | Y | V | Y585 (CA) | C11 | |
| H | N | N | T | N | H | N586 (ND2) | O4 | |
| A | T | D | A | L | V | L587 (CD2) | C11 | |
| | | | | | | B-site interactions | | |
| R | R | R | R | R | R | R277 (NE) | O10 | REF |
| H | H | H | H | H | H | H279 (NE2) | O10 | |
| C | C | C | C | S | C | S280 (OG) | C11 | |
| Q | Q | Q | E | E | Q | E350 (C) | O7 | |
| G | G | G | G | G | G | G351 (CA) | C7 | |
| C | C | C | S | C | C | C352 (CB) | C11 | |
| L | L | L | L | L | L | L353 (O) | C11 | |
| P | P | P | P | P | P | P354 (CA) | O1B | |
| D | D | D | D | Q | D | Q359 (NE2) | O1B | |
| F | F | F | F | F | F | F361 (CD1) | O8 | |
| M | M | M | M | T | M | T362 (O) | O9 | |
| S | G | G | Q | P | S | P533 (CG) | O1A | |
| F | F | F | F | F | F | F650 (CE2) | C9 | 5F |
| S | S | S | S | S | S | S651 (O) | O9 | |
| A | A | P | S | D | A | D652 (OD2) | C3 | |
| | | | | | | Glycerol interactions | | |
| R | R | R | R | R | R | R277 (NH2) | O1 | REF |
| F | F | F | F | F | F | F529 (CB) | O2 | |
| G | G | G | A | N | G | N530 (O) | C3 | |
| K | K | K | G | S | K | S531 (O) | C3 | |
| M | M | M | I | L | M | L548 (CD2) | O3 | |
| Q | Q | Q | Q | Q | Q | Q604 (CG) | O3 | |
| E | E | E | E | T | E | T711 (OG1) | O3 | |

[a]Interaction distance within 3.6 Å.
[b]Receptor type for the particular AAV serotype in parentheses.
[c]Amino acid residues mutated in this study are in boldface and underlined.

Figure 4:
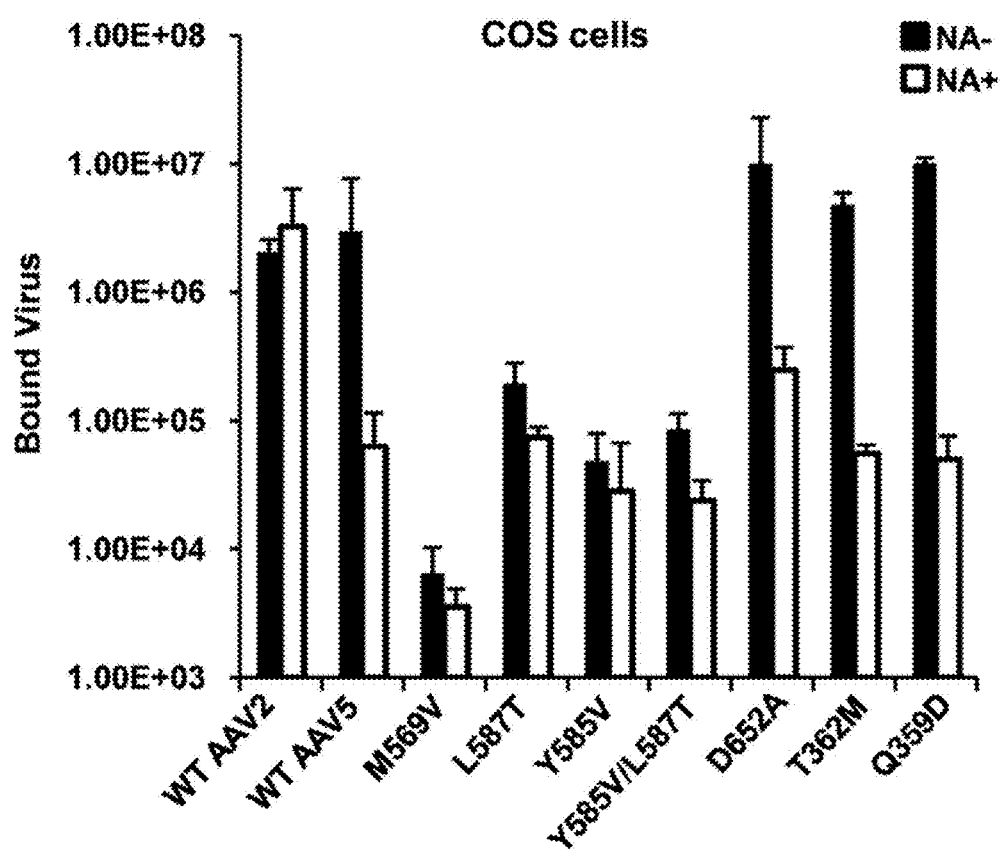
FIG. 4 demonstrates cell binding by WT and mutant vectors. The effect of neuraminidase on vector binding was compared on COS cells with (NA+) or without (NA−) neuraminidase pretreatment. Bound virus was measured by quantitative PCR using primers specific for the CMV promoter. Values are means from three experiments. Error bars represent standard deviations.
Figure 5A:
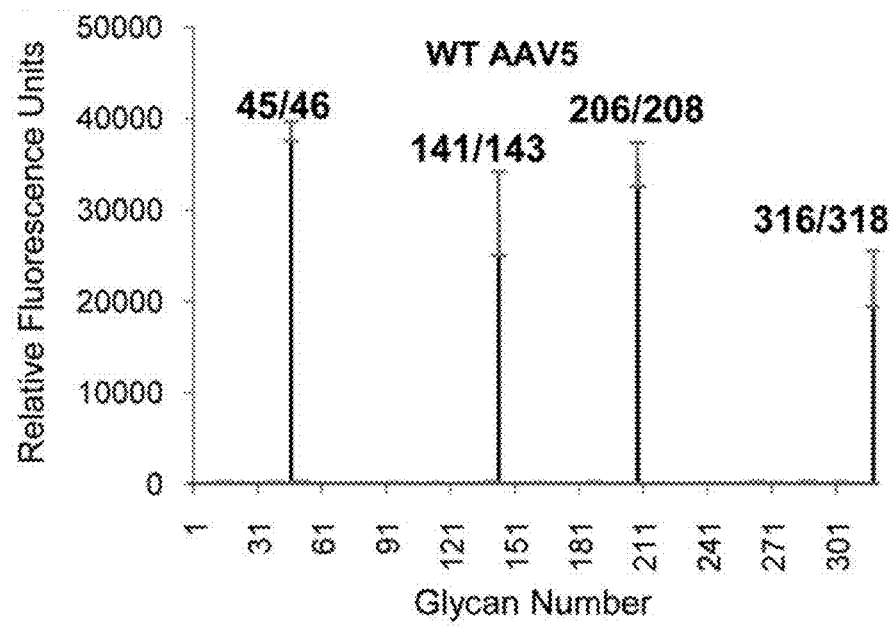
FIG. 5A is a glycan microarray graph of WT AAV5.
Figure 5B:
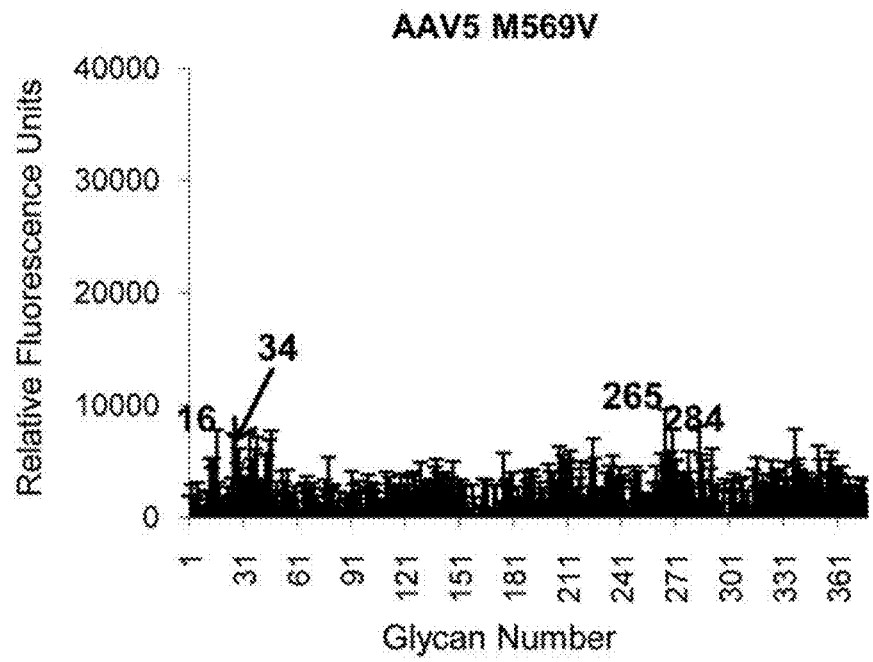
FIG. 5B is a glycan microarray graph of the M569V mutant.
Figure 5C:
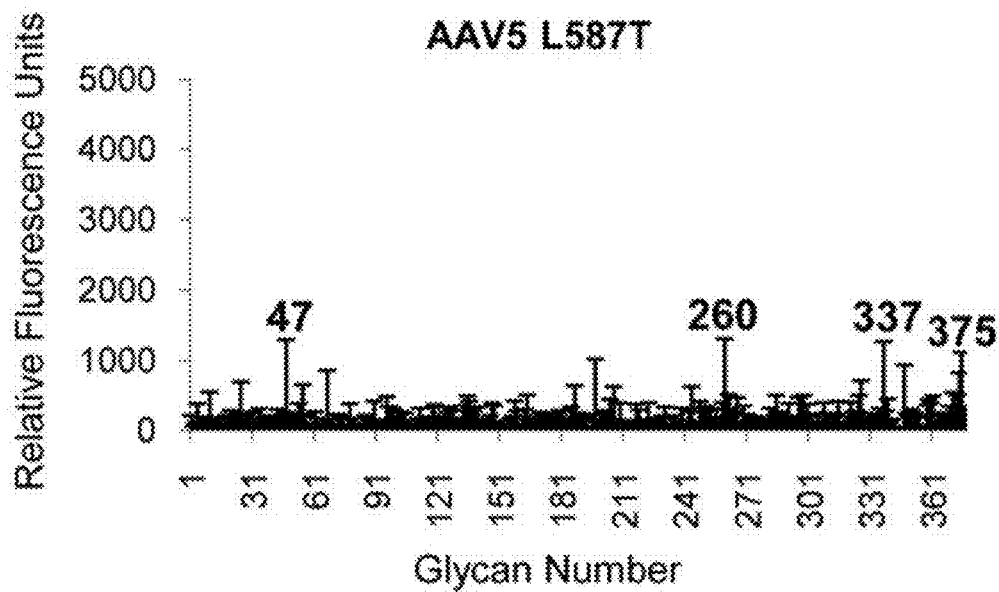
FIG. 5C is a glycan microarray graph of the L587T mutant. In each of these figures, the top hits for the WT AAV5 are labeled, the relative fluorescence units (RFU) are shown in the y-axis and the glycan array # is given in the x-axis, and the top 4 glycan hits (highest RFU) are indicated.
Figure 6A:
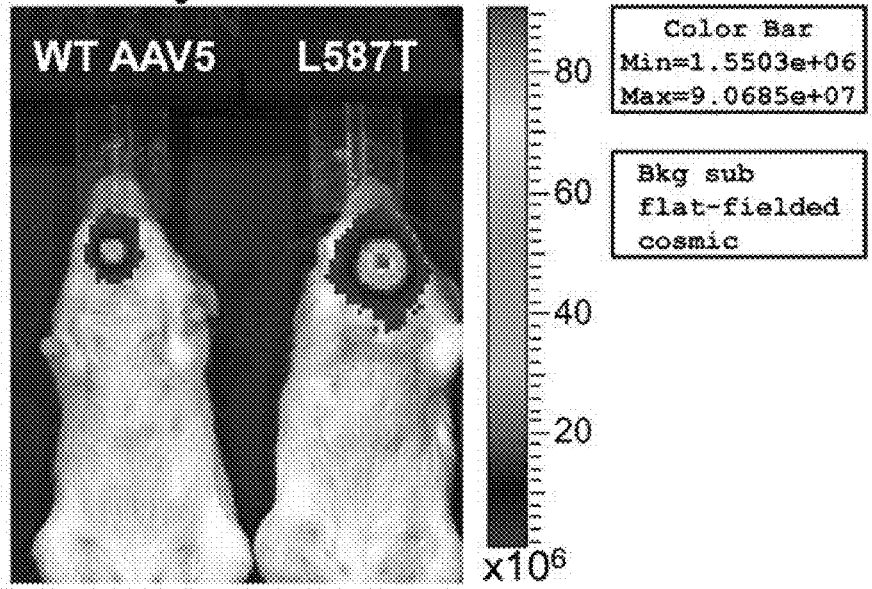
FIGS. 6A-6C show the in vivo transduction activity of WT AAV5 and A-site mutant L587T. The indicated recombinant vectors encoding luciferase were delivered into either balb/c salivary glands (FIG. 6A), muscle (tibialis anterior.
Figure 6B:
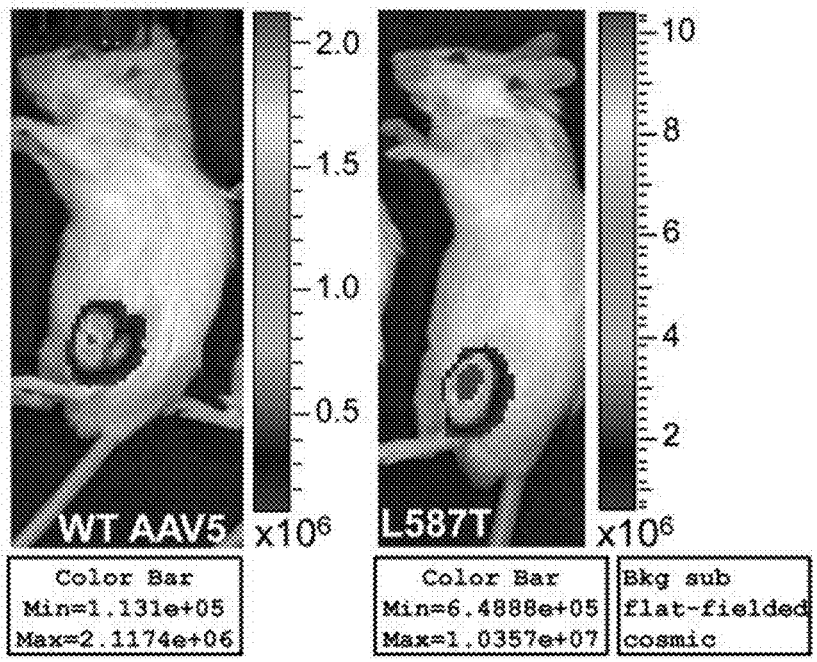
Figure 6C:
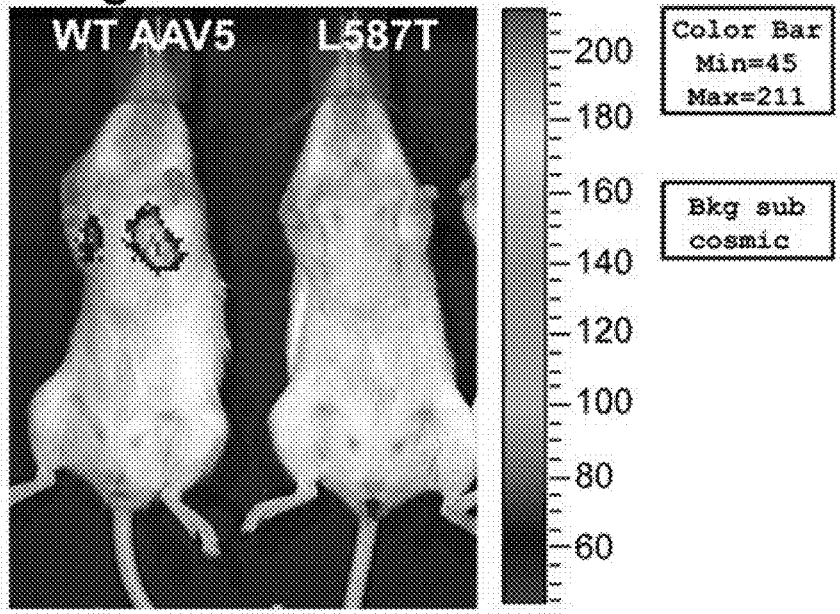
Figure 7:
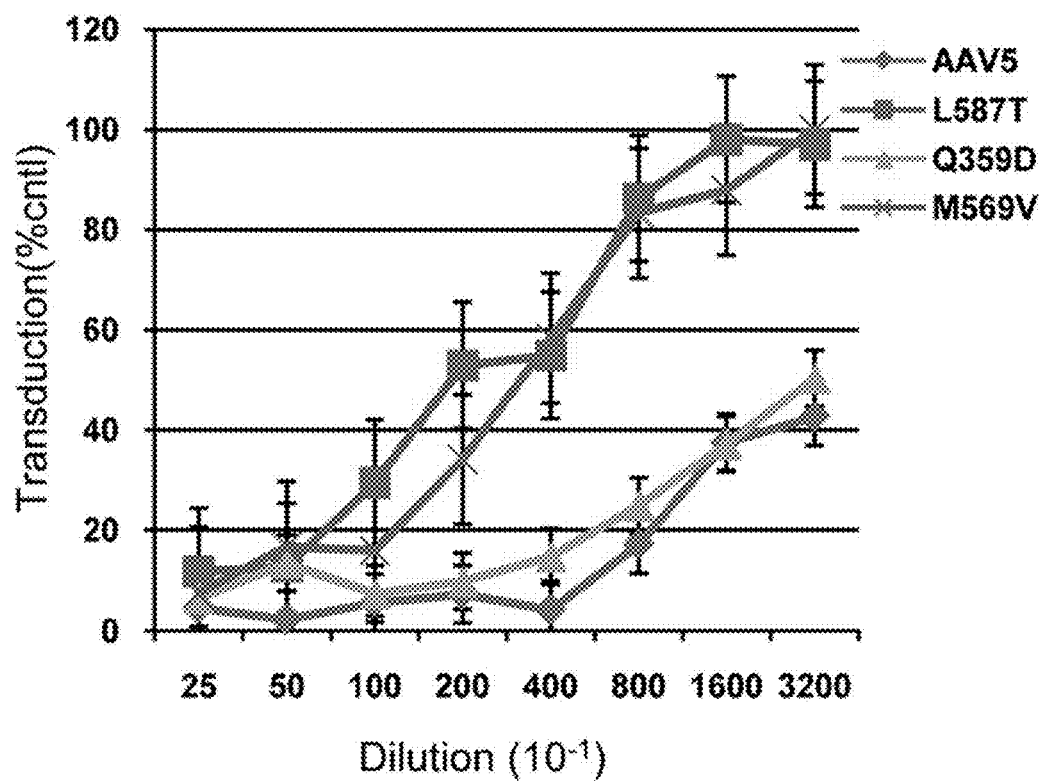
FIG. 7 illustrates neutralization of transduction by WT AAV5 and SIA binding site mutants. The indicated recombinant vectors encoding GFP was incubated with serially diluted anti-AAV5 polyclonal antibody raised in rabbits prior to infection of COS cells. Transduction efficiencies relative to those of an untreated control were plotted against the reciprocal of the dilution of sera incubated with the vector. Values are means from three experiments; error bars represent standard deviations.
Figure 8A:
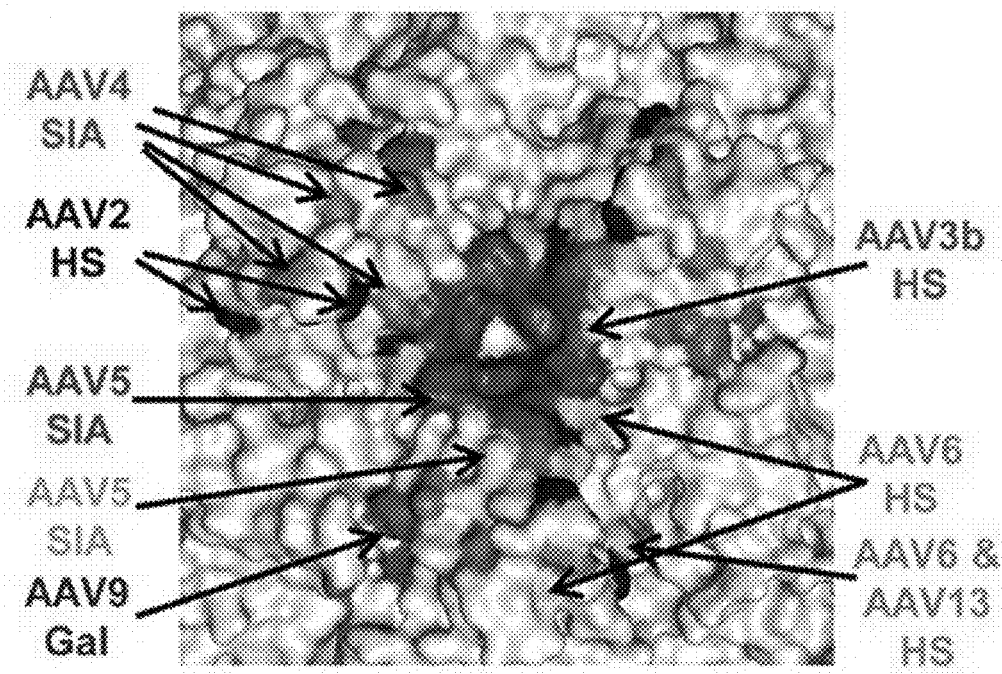
FIGS. 8A and 8B depict AAV-receptor interactions as a close-up of the available glycan receptor footprints for different AAVs on the surface of AAV5 capsid. The residues involved in glycan receptor binding for AAV2, AAV3b, AAV4, AAV5, AAV6, AAV9, and AAV13 are labeled.
Figure 8B:
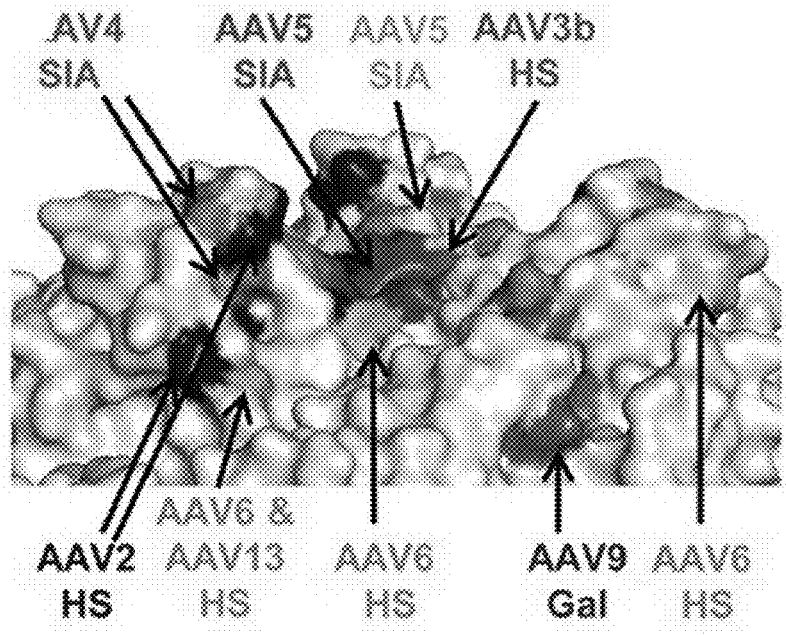

Similar to the A-site mutants, all of the B-site mutants displayed a significant decrease in transduction activity on all cell types, suggesting that this region is also important in A-site mutations change SIA-dependent cell attachment: To confirm if the change in transduction activity was associated with disruption in cell surface SIA interaction, mutant vector binding to cells was compared to that of WT AAV5 with or without pretreatment of the target cells with neuraminidase on COS cells (FIG. 4). While the number of bound particles was smaller for the A-site mutants than for WT AAV5, very little difference in binding was observed if the cells were pretreated with neuraminidase. In agreement with the transduction data, B-site mutations D652A, T362M, and Q359D showed strong neuraminidase-sensitive binding effects. Given that WT AAV5 and the B-site mutants transduction decreased greater than 10-fold with neuraminidase treatment, this observation suggests that the A site is important in both SIA-dependent cell attachment and transduction.

arrays were Neu5Acα2-3Galβ1-4GlcNAcβ1-2Manα1-3 (Neu5Acα2-3Galβ1-4GlcNAcβ1-2Manα1-6) Manβ1-4GlcNAcβ1-4GlcNAcβ-Sp12 (glycan 141/143), and Neu5Acα2-3Galβ1-4GlcNAcβ1-2Manα1-3 (Neu5Acα2-6Galβ1-4GlcNAcβ1-2Manα1- 6) Manβ1-4GlcNAcβ1-4GlcNAcβ-Sp12 (glycan 316/318). Glycans 141/143 and 316/318 contain the same glycans as 45/46 and 206/208, but without the fucosylation and sulfation, linked to core mannose on both branches. Glycans 141/143 and 316/318 differ in that the terminal SIA in one of the branches in glycan 316/318 is linked by α2,6 rather than α2,3 to galactose. Binding of AAV5 to these sulfonated and branched glycans was also recently reported elsewhere (28).

TABLE 4

WT AAV5 and AAV5 M569V and L587T mutant capsid glycan specificity on glycan arrays[a]

| AAV5 and glycan no. | Glycan name | RFU | SD | SEM | % CV |
| --- | --- | --- | --- | --- | --- |
| Wild-type AAV5 | | | | | |
| 45/46[b] | NeuAcα2-3[6OSO3]Galβ1-4GlcNAcβ-Sp8 | 38,621 | 2,164 | 1,082 | 6 |
| 206/208[b] | Neu5Acα2-3(6-O-Su)Galβ1-4(Fucα1-3)GlcNAcβ-Sp8 | 34,986 | 4,816 | 2,408 | 14 |
| 141/143[b] | Neu5Acα2-3Galβ1-4GlcNAcβ1-2Manα1-3(Neu5Acα2-3Galβ1-4GlcNAcβ1-2Manα1-6)Manβ1-4GlcNAcβ1-4GlcNAcβ-Sp12 | 29,649 | 9,158 | 4,579 | 31 |
| 316/318[b] | Neu5Acα2-3Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 22,531 | 6,079 | 3,040 | 27 |
| M569V mutant | | | | | |
| 265 | [3OSO3]Galb1-4[Fuca1-3][6OSO3]GlcNAc-Sp8 | 9,148 | 1,045 | 523 | 11 |
| 284 | [3OSO3]Galb1-4[6OSO3]GlcNAcb-Sp0 | 7,875 | 565 | 282 | 7 |
| 16 | b-d-Gal-Sp8 | 7,179 | 1,267 | 634 | 18 |
| 34 | [3OSO3]Galb1-4[6OSO3]GlcNAcb-Sp8 | 7,174 | 604 | 302 | 8 |
| L587T mutant | | | | | |
| 47 | 9NAcNeu5Aca-Sp8 | 1,092 | 411 | 205 | 38 |
| 337 | GlcNAca1-4Galb1-4GlcNAcb1-3Galb1-4(Fuca1-3)GlcNAcb1-3Galb1-4(Fuca1-3)GlcNAcb-Sp0 | 929 | 682 | 341 | 73 |
| 260 | Neu5Gca2-6GalNAca-Sp0 | 929 | 762 | 381 | 82 |
| 375 | GalNAcb1-4GlcNAcb1-2Mana1-6(GalNAcb1-4GlcNAcb1-2Mana1-6)Manb1-4GlcNAcb1-4GlcNAc-Sp12 | 908 | 422 | 211 | 46 |

[a]The top four glycans with the highest relative fluorescence units (RFU) for each vector are listed.
[b]Numbers are based on PA Ver. 3.1/3.0.

Specificity of carbohydrate binding by A-site mutants on a glycan microarray: Among the A-site mutations, two phenotypes of transduction were observed, complete inhibition of transduction on all cells as seen with M569V or cell type-dependent neuraminidase-sensitive transduction with Y585V and L587T. Based on these data, we hypothesized that M569V completely abolished SIA binding while L587T and to a lesser extent Y585V altered SIA specificity. To test this hypothesis WT, M569V, and L587TrAAV-GFP vectors were used to probe glycan microarrays developed by the CFG. WT AAV5 reproducibly bound a subset of SIA-containing glycans on the array (Table 4; FIGS. 5A-5C): NeuAcα2-3[6OSO3] Galβ1-4GlcNAcβ-Sp8 (glycan 45/46) and Neu5Acα2-3(6OSO3) Galβ1-4(Fucα1-3) GlcNAcβ-Sp8 (glycan number 206/208), both with α2,3-linked terminal SIA and sulfated on the penultimate galactose group. Glycan 206/208 differs from 45/46 by having a fucose group on the N-acetylglucosamine of the glycan chain. Two additional SIA-containing glycans bound by AAV5 on newer Unlike the data for the WT AAV5, the M569V mutant showed nonspecific binding to most of the glycans on the microarray. The top hits, with acceptable percent coefficient of variation (% CV) values, did not contain terminal SIA, and most of them were sulfated (FIGS. 5A-5C; Table 4). For the L587T mutant, the binding to all the glycans was low, with all potential hits for glycans with terminal SIA having high % CV values consistent with low signal-to-noise ratios. Interestingly, the top hit for this mutant is 9NAcNeu5Aca-Sp8 (glycan number 47) with a % CV of 38 (Table 4). Significantly, SIA 9-O-acetylation is upregulated (e.g., 9-O-acetylated GD3) in human melanoma cells (29). Thus, it is possible that this or another modified glycan is being utilized by the L587T mutant for the infection of cancer cells such as the IGROV-1 cells.

The glycan microarray observations for the mutant viruses are consistent with the reduced binding in COS cells compared to WT AAV5 and the lack of significant difference in binding to cells without/with neuraminidase treatment (FIG. 4). The data also support the transduction data and indicate that (i) the A site is critical for SIA binding and either (ii) mutation in this region can completely abolish SIA binding or (iii) mutation in this region can retarget the capsid to different modified glycans, such as for the L587T mutant vector.

Mutation of L587 alters SIA binding for AAV5. Previous research had demonstrated robust transgene expression following WT AAV5 vector delivery to lung or salivary gland epithelia (30, 31). Thus, to test if the altered SIA binding specificity by L587T also alters tropism in vivo, gene expression was monitored in mice for WT AAV5 or L587T vectors encoding luciferase. In agreement with the change in in vitro carbohydrate binding and cell tropism, the L587T mutant also demonstrated a change in transduction activity in vivo (see FIGS. 6A-6C). Following vector delivery to the submandibular salivary glands, the L587T mutant demonstrated a 3- to 4-fold increase in transduction activity compared to WT AAV5. Similarly, a direct injection of L587T mutant in the hind limb showed a 3- to 4-fold increase in luciferase expression compared with WT AAV5. In contrast, L587T mutant gene transfer to the lung was greatly reduced compared with WT AAV5. M569V and Q359D mutants were also evaluated in the salivary glands and showed no transduction activity (data not shown). These data suggest that alteration in glycan recognition can affect vector activity in vivo.

AAV5 SIA binding residues map to an antigenic region: We hypothesized that alteration of a critical region for transduction could alter the antigenic profile of the vector and thus its neutralization by serum antibodies. The antigenic profiles of selected A-site and B-site mutants were explored in comparison to that of WT AAV5 (FIG. 7). At low dilutions of an anti-AAV5 polyclonal serum, all mutants were neutralized to the same extent as WT AAV5. However, further serial dilution of this serum demonstrated distinct properties for the A-site and B-site mutants. In contrast to the B-site Q359D mutant, which was neutralized to an extent similar to that of WT AAV5, both of the A-site mutants showed a sharp reduction in neutralization activity with dilutions of 100-fold or greater than the Q359D mutant or WT AAV5. Thus, in addition to being critical for SIA-dependent transduction, the A site represents an important antigenic region on AAV5, and its alteration creates an antigenic escape mutant (L587T mutant) still capable of robust in vitro and in vivo transgene expression.

In summary, we have identified a region used for SIA binding by AAV5, an essential interaction for successful infection. The binding site conserves the general features observed in other virus-capsid interactions. Further analysis of the SIA binding pocket in AAV5 and characterization of other SIA-dependent AAVs will be necessary to identify the interplay between the bound glycans and the receptors required for internalization. The data so far clearly point to the icosahedral 3-fold axis as being important in cell binding by multiple isolates of AAV, while versatility in capsid interactions shows that the 2-fold region of the autonomous parvovirus capsid is also suitable for SIA receptor attachment. Since structure is more conserved than sequence, information on all receptor-interacting regions can inform vector-retargeting developments. Manipulation of these regions, given knowledge of their functions, will lead to improvements in the development of the AAV gene transfer system.

Example 2: Delivery and Expression of Nucleic Acid of Interest in Subretinal Tissue of the Eye

Vector Production

Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Wild-type AAV5 and recombinant virus comprising the capsid mutant vectors expressing luciferase are produced as described in Example 1.

Injections: The in vivo study of transgene expression is conducted as described in Example 1. Vector particles ($3\times10^{12}$ vg/ml viral particles) of WT AAV5 or recombinant vectors encoding luciferase are injected into mice by subretinal injection.

Subretinal Injection Technique

To study retinal cell transduction in rats, Adult Wistar rats (375-425 g) are anesthetized with intraperitoneal ketamine (50 mg/kg) and xylazine (5 mg/kg) and topical 1% proparacaine eye drops and pupils are dilated with 1% tropicamide and 2.5% phenylephrine eye drops. A superotemporal conjunctival incision is made using a surgical microscope so that the sclera posterior to the lens is exposed. Using a 30-G needle to facilitate penetration of the underlying sclera, choroid, and retina, a fine hole is opened. After formation of the partial-thickness scleral pilot hole, a fine glass micropipette with a tip diameter of 30 lm and a tip length of 1.5 mm is directed more obliquely than for intravitreal injection, into the space between the RPE and the neuroretina. Correct cannula placement can be verified by observation of a bullous retinal detachment following subretinal injection without evidence of a retinal hole or tear. Injection of a volume of 2-3 ll is usually sufficient to cause a subretinal bleb involving 30-40% of the fundus.

Histochemistry

Approximately one month after injection, mice are sacrificed and the eyes are removed and processed to identify luciferase expressing cells. For each mouse, the number of expressing cells in tissue of the eye is counted and summed to provide quantitative extent of transduction. Depending on the transgene, transduction can be visualized by photon imaging of the eye using a Xenogen camera (IVIS Lumina; PerkinElmer) or, if the transgene is GFP, by fluorescences.

To test if the altered SIA binding specificity by L587T also alters tropism in vivo, gene expression is monitored in mice encoding GFP. In agreement with the change in in vitro carbohydrate binding and cell tropism, the L587T mutant demonstrates a change in transduction activity in vivo. FIG. 10 shows photon imaging of an eye following subretinal injection of a recombinant virus comprising the L587T capsid mutant and a negative control. Following vector delivery to the subretinal tissues, the L587T mutant demonstrates significant transduction activity. The data will show that alteration in glycan recognition affects vector activity in vivo.

These experiments will explore the use of the recombinant AAV5 vectors of this disclosure as a vector for nucleic acid transfer to the eye. The recombinant AAV5-L587T will demonstrate a distinct affinity for transduction of the tissues of the eye.

Example 3: Delivery and Expression of Nucleic Acid of Interest in Intravitreal Space in the Eye

Vector Production

Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Recombinant virus comprising the capsid mutant vectors expressing a transgene are produced as described in Example 1.

Injections

The in vivo study of transgene expression is conducted as described in Example 1. Vector particles ($3 \times 10^{12}$ vg/ml viral particles) of recombinant vectors encoding luciferase are injected into mice by intravitreal injection.

Intravitreal Injection Technique

To study retinal cell transduction in rats, Adult Wistar rats (375-425 g) are anesthetized with intraperitoneal ketamine (50 mg/kg) and xylazine (5 mg/kg) and topical 1% proparacaine eye drops and pupils are dilated with 1% tropicamide and 2.5% phenylephrine eye drops. A superotemporal conjunctival incision is made using a surgical microscope so that the sclera posterior to the lens is exposed. Using a 30-G needle to facilitate penetration of the underlying sclera, choroid, and retina, a fine hole is opened and a fine glass micropipette with a tip diameter of 30 um and a tip length of 2.5 mm is connected to a glass syringe by polyethylene tubing prefilled with light mineral oil, prior to drawing up the virus stock. The targeted injection site is located about 3 mm posterior to the superotemporal limbus. Injections are given slowly over 1 minute to allow diffusion of the virus stock. After each injection, the injection site is visualized with a standard indirect ophthalmoscope using a 90-diopter condensing lens (Volk Optical, Mentor, Ohio).

Histochemistry

Approximately 1 month after injection mice are sacrificed and the eyes are removed and processed to identify transgene expressing cells. For each mouse, the number of expressing cells in tissue of the eye is counted and summed to provide quantitative value of the extent of transduction. In agreement with the change in in vitro carbohydrate binding and cell tropism, the AAV5 mutants will demonstrate a change in transduction activity in tissues of the eye in vivo.

Example 4: Delivery and Expression of Nucleic Acid of Interest in Tissues of the Lung Vector Production Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Recombinant virus comprising the capsid mutant vectors expressing luciferase are produced as described in Example 1.

Injections

The in vivo study of transgene expression is conducted as described in Example 1. Vector particles ($3 \times 10^{12}$ vg/ml viral particles) encoding luciferase are administered to mice by aerosol delivery to the lung.

Aerosol Delivery of AAV Vectors to the Lung

Up to 50 µl of sterile saline will be placed at the end of each nostril so that the droplets are inhaled. Prior to i.n. vector delivery, mice will be anesthetized either with isoflurane gas or with an i.m. injection of ketamine [60-80 mg/kg] and xylazine [8-10 mg/kg]). Animals are allowed to recover on heating pads and returned to their cages, grouped according to their experimental treatment. Animals, however, will not be returned to their cages until they have recovered the ability to ambulate and change posture, which also indicates an ability to again regulate their body temperature. Using a fine tipped 10-µl Eppendorf pipette tip and alternating drops between both nostrils, a drop will be placed gently at the tip of the nostril, with a maximum volume of 7 µl per drop. This procedure will be repeated three times for a total of 8 drops (4 drops/nostril) administered during a 15-min period (maximum volume, 56 µl).

Histochemistry

Approximately 1 month after injection, mice are sacrificed and the lungs are removed and processed to identify expressing cells. For each mouse, the number of expressing cells in tissues of the lung (including macrophages, epithelial, alveolar and bronchiol ductal cells) is counted and summed to provide quantitative extent of transduction. In agreement with the change in in vitro carbohydrate binding and cell tropism, the AAV5 mutants will demonstrate a change in transduction activity in tissues of the lung in vivo.

Example 5: Delivery and Expression of Nucleic Acid of Interest in Tissues of the Liver Vector Production Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Wild-type AAV5 and recombinant virus comprising the capsid mutant vectors expressing luciferase are produced as described in Example 1.

Injections

The in vivo study of transgene expression is conducted as described in Example 1. Vector particles ($3 \times 10^{12}$ vg/ml viral particles) encoding a transgene such as luciferase are administered to mice by injection for targeted delivery to the liver.

Targeted Delivery of AAV Vectors to the Liver

Several routes of delivery to the liver are used, including the portal vein, peripheral vein, superficial temporal vein, and hepatic infusion.

Vector will be delivered via the portal vein by anesthetizing a mouse and then making a midline incision in the abdomen to expose the portal vein connecting the intestine with the liver. Using a 30G needle, up to 0.2 ml of vector in isotonic media is slowly injected over a 1 min period. Following needle removal, gauze is used to control bleeding and the abdomen is sutured.

For peripheral vein infusion, a 20 or 22-gauge intravenous catheter is inserted into the saphenous vein of an anesthetized macaque. Alternatively, a 30-gauge needle is used in a mouse. The vector is diluted in isotonic buffer to a final volume that is less than 10 mL/kg of the total body weight of the macaque or mouse, and then infused through the catheter/needle over 30 minutes while monitoring the animal's vital signs and oxygen saturation.

For administration via the superficial temporal vein, the superficial temporal vein that extends from behind the eye into the neck is exposed. A 30-gauge needle affixed to a 1 cc syringe is inserted under the skin next to the vein starting at the direction of the head down until the vein is pierced. The viral suspension is slowly injected over 1 min.

Intrahepatic injection is accomplished by creating a midline incision in the abdomen in an anesthetized animal. This will be retracted to expose the liver. Using a 30G needle, virion suspension will be slowly infused into the liver at multiple sites in an animal. Following infusion, the abdomen will be closed by suture.

Histochemistry

Approximately 1 month after injection, mice are sacrificed and the liver is removed and processed to identify expressing cells. For each mouse, the number of expressing cells in tissues of the liver (including hepatocytes, kupffer cells, and endothelial cells) is counted and summed to provide quantitative extent of transduction. In agreement with the change in in vitro carbohydrate binding and cell tropism, the AAV5 mutants will demonstrate a change in transduction activity in tissues of the liver in vivo.

Example 6: Delivery and Expression of Nucleic Acid of Interest in Tissues of the Brain Vector Production Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Wild-type AAV5 and recombinant virus comprising the capsid mutant vectors expressing luciferase are produced as described in Example 1.

Injections

The in vivo study of transgene expression is conducted as described in Example 1. Vector particles ($3\times10^{12}$ vg/ml viral particles) encoding a transgene such as luciferase are administered to mice by injection for targeted delivery to the brain.

Targeted Delivery of AAV Vectors to the Brain

Six to 8-week old adult male C57BL/6 mice are anaesthetized and vectors are stereotactically injected into either the right lateral ventricle or the right striatum, using a 26 gauge Hamilton syringe driven by a microinjector (Micro 1, World Precision Instruments, Sarasota, Fla.) at 0.5 μl per minute. For ventricular injections, 10 μl volumes are injected at coordinates 0.4 mm rostral and 1.0 mm lateral to bregma, and at a 2 mm depth. For striatal injections, 5 μl volumes are injected at coordinates 0.4 mm rostral and 2 mm lateral to bregma, and at a 3 mm depth. A minimum of two independent experiments are done for each virion and injection site.

Histochemistry: Three or 15 weeks after injection, groups of mice are perfused with 2% paraformaldehyde; the brains were removed and 10 μm thick coronal sections are cut at 100 μm intervals and quantification performed to identify expressing cells. For each mouse, the number of positive cells in every fourth section, spanning 1.3 mm of tissue rostral and 1.3 mm caudal to the injection site, will be counted and summed. These sums allow quantitative comparisons among the virions, although they do not reflect the total number of transduced cells in vivo.

Immunofluorescent Staining

Ten micrometer coronal cryosections of brains harvested 15 weeks after intrastriatal injection of the recombinant virions will be dual stained for the transgene and either neuronal or astrocytic markers. The primary antibodies used are as follows: rabbit IgG specific for the transgene; mouse monoclonal IgG specific for NeuN (Chemicon International, Inc., Temecula, Calif.), which strongly stains neuronal cell nuclei with lighter staining of the cytoplasm; and a Cy5 conjugated mouse monoclonal specific for glial fibrillary acidic protein (GFAP) (Sigma Immunocytochemicals, St. Louis, Mo.), an intermediate filament of astrocytes. Secondary antibodies used are ALEXA 488 goat anti-rabbit IgG (Molecular Probes, Eugene, Oreg.) and lissamine-rhodamine goat anti-mouse IgG (Jackson ImmunoResearch Laboratories, West Grove, Pa.). Sections are blocked for 2 h at room temperature in phosphate-buffered saline (PBS) with 3% bovine serum albumin, 10% normal goat serum and 0.1% Triton X-100. Sections were incubated overnight with primary antibodies diluted in PBS with 3% bovine serum albumin and 0.1% Triton X-100 at 4° C., then washed and incubated with secondary antibodies in PBS with 1% normal goat serum and 0.1% Triton X-100 for 2 hours at room temperature. Confocal laser microscopy will be performed using 63× and 40× oil-immersion objectives on a Zeiss LSM 510 and associated software. Z-series images (0.3 to 1.0 μm wide slices) are captured and analyzed for cellular co-localization of antigens. Colocalization of luciferase and either NeuN or GFAP will be represented in 2-color merged images from single slices within the series.

To test if the altered SIA binding specificity by L587T also alters tropism in vivo, gene expression is monitored in mice for L587T vectors encoding luciferase. In agreement with the change in in vitro carbohydrate binding and cell tropism, the L587T mutant will demonstrate a change in transduction activity in tissues of the brain in vivo.

Example 7: Ex Vivo Transduction and Expression of Nucleic Acid of Interest in Myoblasts Vector Production Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Wild-type AAV5 and recombinant virus comprising the capsid mutant vectors expressing luciferase are produced as described in Example 1.

Transduction of Myoblasts

Chicken myoblasts are cultured and plated as previously described (Rhodes & Yamada 1995 NAR Vol 23 (12) 2305-13). Cells are allowed to fuse and are then transduced with a similar number of particles of recombinant AAV vectors containing a transgene such as luciferase. The cells are assayed for luciferase activity and the transduction quantified. The data will show that alteration in glycan recognition affects vector activity in vivo. These experiments will also explore the use of the recombinant AAV5 vectors of this disclosure as a vector for nucleic acid transfer to muscle tissue. The recombinant AAV5-luciferase will demonstrate a distinct affinity for transduction of muscle tissue.

Example 8: Delivery and Expression of Nucleic Acid of Interest in Salivary Glands Vector Production Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Wild-type AAV5 and recombinant virus comprising the capsid mutant vectors expressing luciferase are produced as described in Example 1.

Injections

The in vivo study of transgene expression is conducted as described in Example 1. Vector particles encoding luciferase are administered to mice by injection for targeted delivery to salivary glands.

Delivery of AAV Vectors to Salivary Glands

Vectors are delivered into the submandibular glands by retrograde instillation. Briefly, mild anesthesia is induced by ketamine (100 mg/mL, 1 mL/kg body weight) and xylazine (20 mg/mL, 0.7 mL/kg body weight) solution given intramuscularly (IM). Ten minutes after IM injection of atropine (0.5 mg/kg body weight), mice at the age of 30 weeks are administered 50 μl vector into both submandibular glands by retrograde ductal instillation using a thin cannula (Intermedic PE10, Clay Adams). The vector dose is chosen based on previously published results, which showed detectable transgene activity. The mouse salivary glands are collected, their RNAs extracted, and changes in nucleic acid expression identified by microarray analysis. Histochemistry: Approximately 1 month after injection, mice are sacrificed and the salivary glands are processed to identify expressing cells. For each mouse, the number of expressing cells in salivary glands are counted and summed to provide quantitative value for the extent of transduction.

To test if the altered SIA binding specificity by L587T also alters tropism in vivo, gene expression is monitored in mice encoding luciferase. In agreement with the change in in vitro carbohydrate binding and cell tropism, the L587T mutant will demonstrate a change in transduction activity in vivo. The data will show that alteration in glycan recognition affects vector activity in vivo. These experiments will also explore the use of the recombinant AAV5 vectors of this disclosure as a vector for nucleic acid transfer to salivary glands. The recombinant AAV5-luciferase will demonstrate a distinct affinity for transduction of the salivary gland.

Example 9: Delivery and Expression of Nucleic Acid of Interest to Capillary Epithelial Cells Vector Production Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Wild-type AAV5 and recombinant virus comprising the capsid mutant vectors expressing luciferase are produced as described in Example 1.

Injections

The in vivo study of transgene expression is conducted as described in Example 1. Vector particles ($3\times10^{12}$ vg/ml viral particles) encoding a transgene such as luciferase are administered to mice by injection for targeted delivery to capillary epithelial cells by intravenous injection of virion suspension into mice.

Histochemistry: Approximately 1 month after injection mice are sacrificed; capillary epithelial cells are processed to identify expressing cells. For each mouse, the number of luciferase-expressing cells in the collected capillary epithelial cells are counted and summed to provide quantitative value for the extent of transduction.

These experiments will explore the use of the recombinant AAV5 vectors of this disclosure as a vector for nucleic acid transfer to epithelial cells. The recombinant AAV5-luciferase will demonstrate a distinct affinity for transduction of epithelial cells.

Example 10: Ex Vivo Transduction and Expression of Nucleic Acid of Interest in Tumor Cells Vector Production Mutant capsid plasmids of this invention, including capsids having the A-site mutants M569V, Y585V, and L587T mutants, and the double mutant Y585V/L587T, and the B-site mutants D652F, T362M, Q359D, E350Q, P533S, P533G, are prepared as described in Example 1. Wild-type AAV5 and recombinant virus comprising the capsid mutant vectors expressing luciferase are produced as described in Example 1.

Tumor cells are cultured and treated with varying concentrations of the recombinant AAV virions of this invention, expressing luciferase or another transgene such as GFP. The results of this analysis will indicate that different dosages of these recombinant virions induce different response patterns of the transgene expression. The expression changes will be verified by Quantitative-PCR.

These experiments will explore the use of the recombinant AAV5 vectors of this disclosure as a vector for nucleic acid transfer to tumor cells. The recombinant AAV5-luciferase will demonstrate a distinct affinity for transduction of tumor cells.

REFERENCES

1. Rabinowitz J E, Rolling F, Li C, Conrath H, Xiao W, Xiao X, Samulski R J. 2002. Cross-packaging of a single adeno-associated virus (AAV) type 2 vector genome into multiple AAV serotypes enables transduction with broad specificity. Journal of virology 76:791-801.
2. Schmidt M, Govindasamy L, Afione S, Kaludov N, Agbandje-McKenna M, Chiorini J A. 2008. Molecular characterization of the heparin-dependent transduction domain on the capsid of a novel adeno-associated virus isolate, AAV (VR-942). Journal of virology 82:8911-8916.
3. Halbert C L, Allen J M, Miller A D. 2001. Adeno-associated virus type 6 (AAV6) vectors mediate efficient transduction of airway epithelial cells in mouse lungs compared to that of AAV2 vectors. Journal of virology 75:6615-6624.
4. Handa A, Muramatsu S, Qiu J, Mizukami H, Brown K E. 2000. Adeno-associated virus (AAV)-3-based vectors transduce haematopoietic cells not susceptible to transduction with AAV-2-based vectors. The Journal of general virology 81:2077-2084.
5. Seiler M P, Miller A D, Zabner J, Halbert C L. 2006. Adeno-associated virus types 5 and 6 use distinct receptors for cell entry. Human gene therapy 17:10-19.
6. Summerford C, Samulski R J. 1998. Membrane-associated heparan sulfate proteoglycan is a receptor for adeno-associated virus type 2 virions. Journal of virology 72:1438-1445.
7. Wu Z, Miller E, Agbandje-McKenna M, Samulski R J. 2006. Alpha2,3 and alpha2,6 N-linked sialic acids facilitate efficient binding and transduction by adeno-associated virus types 1 and 6. Journal of virology 80:9093-9103.
8. Kaludov N, Brown K E, Walters R W, Zabner J, Chiorini J A. 2001. Adeno-associated virus serotype 4 (AAV4) and AAV5 both require sialic acid binding for hemagglutination and efficient transduction but differ in sialic acid linkage specificity. Journal of virology 75:6884-6893.
9. Walters R W, Pilewski J M, Chiorini J A, Zabner J. 2002. Secreted and transmembrane mucins inhibit gene transfer with AAV4 more efficiently than AAV5. The Journal of biological chemistry 277:23709-23713.
10. Wu Z, Asokan A, Grieger J C, Govindasamy L, Agbandje-McKenna M, Samulski R J. 2006. Single amino acid changes can influence titer, heparin binding, and tissue tropism in different adeno-associated virus serotypes. Journal of virology 80:11393-11397.

11. Schmidt M, Chiorini J A. 2006. Gangliosides are essential for bovine adeno-associated virus entry. Journal of virology 80:5516-5522.
12. Rooney C P, Denning G M, Davis B P, Flaherty D M, Chiorini J A, Zabner J. 2002. Bronchoalveolar fluid is not a major hindrance to virus-mediated gene therapy in cystic fibrosis. Journal of virology 76:10437-10443.
13. Kern A, Schmidt K, Leder C, Muller O J, Wobus C E, Bettinger K, Von der Lieth C W, King J A, Kleinschmidt J A. 2003. Identification of a heparin-binding motif on adeno-associated virus type 2 capsids. Journal of virology 77:11072-11081.
14. Opie S R, Warrington K H, Jr., Agbandje-McKenna M, Zolotukhin S, Muzyczka N. 2003. Identification of amino acid residues in the capsid proteins of adeno-associated virus type 2 that contribute to heparan sulfate proteoglycan binding. Journal of virology 77:6995-7006.
15. Di Pasquale G, Davidson B L, Stein C S, Martins I, Scudiero D, Monks A, Chiorini J A. 2003. Identification of PDGFR as a receptor for AAV-5 transduction. Nature medicine 9:1306-1312.
16. DiMattia M, Govindasamy L, Levy H C, Gurda-Whitaker B, Kalina A, Kohlbrenner E, Chiorini J A, McKenna R, Muzyczka N, Zolotukhin S, Agbandje-McKenna M. 2005. Production, purification, crystallization and preliminary X-ray structural studies of adeno-associated virus serotype 5. Acta crystallographica. Section F, Structural biology and crystallization communications 61:917-921.
17. McPherson. 1982. Preparation and Analysis of Protein Crystals, 1 ed. New York: Wiley.
18. Otwinowski Z, Minor W. 1997. Processing of X-ray Diffraction data in oscillation mode. p. 307-326, Methods in Enzymology, vol. 276.
19. Govindasamy L, DiMattia M A, Gurda B L, Halder S, McKenna R, Chiorini J A, Muzyczka N, Zolotukhin S, Agbandje-McKenna M. 2013. Structural insights into adeno-associated virus serotype 5. Journal of virology 87:11187-11199.
20. Brunger A T, Adams P D, Clore G M, DeLano W L, Gros P, Grosse-Kunstleve R W, Jiang J S, Kuszewski J, Nilges M, Pannu N S, Read R J, Rice L M, Simonson T, Warren G L. 1998. Crystallography & NMR system: A new software suite for Macromolecular structure determination. Acta crystallographica. Section D, Biological crystallography 54:905-921.
21. Kleywegt G J. 2007. Crystallographic refinement of ligand complexes. Acta crystallographica. Section D, Biological crystallography 63:94-100.
22. Adams P D, Afonine P V, Bunkoczi G, Chen V B, Davis I W, Echols N, Headd J J, Hung L W, Kapral G J, Grosse-Kunstleve R W, McCoy A J, Moriarty N W, Oeffner R, Read R J, Richardson D C, Richardson J S, Terwilliger T C, Zwart P H. 2010. PHENIX: a comprehensive Python-based system for macromolecular structure solution. Acta crystallographica. Section D, Biological crystallography 66:213-221.
23. Emsley P, Lohkamp B, Scott W G, Cowtan K. 2010. Features and development of Coot. Acta crystallographica. Section D, Biological crystallography 66:486-501.
24. DeLano W L 2002, posting date. The PyMOL Molecular Graphics System DeLano Scientific, San Carlos, Calif., USA. [Online.]
25. Kaludov N, Handelman B, Chiorini J A. 2002. Scalable purification of adeno-associated virus type 2, 4, or 5 using ion-exchange chromatography. Human gene therapy 13:1235-1243.
26. Smith R H, Afione S A, Kotin R M. 2002. Transposase-mediated construction of an integrated adeno-associated virus type 5 helper plasmid. BioTechniques 33:204-206, 208, 210-201.
27. Quinn K, Quirion M R, Lo C Y, Misplon J A, Epstein S L, Chiorini J A. 2011. Intranasal administration of adeno-associated virus type 12 (AAV12) leads to transduction of the nasal epithelia and can initiate transgene-specific immune response. Molecular therapy: the journal of the American Society of Gene Therapy 19:1990-1998.
28. Mietzsch M, Broecker F, Reinhardt A, Seeberger P H, Heilbronn R. 2014. Differential adeno-associated virus serotype-specific interaction patterns with synthetic heparins and other glycans. Journal of virology 88:2991-3003.
29. Ritter G, Boosfeld E, Markstein E, Yu R K, Ren S L, Stallcup W B, Oettgen H F, Old L J, Livingston P O. 1990. Biochemical and serological characteristics of natural 9-O-acetyl GD3 from human melanoma and bovine buttermilk and chemically 0-acetylated GD3. Cancer research 50:1403-1410.
30. Katano H, Kok M R, Cotrim A P, Yamano S, Schmidt M, Afione S, Baum B J, Chiorini J A. 2006. Enhanced transduction of mouse salivary glands with AAV5-based vectors. Gene therapy 13:594-601.
31. Zabner J, Seiler M, Walters R, Kotin R M, Fulgeras W, Davidson B L, Chiorini J A. 2000. Adeno-associated virus type 5 (AAV5) but not AAV2 binds to the apical surfaces of airway epithelia and facilitates gene transfer. Journal of virology 74:3852-3858.
32. Huang L Y, Halder S, Agbandje-McKenna M. 2014. Parvovirus glycan interactions. Current opinion in virology 7C:108-118.
33. Girod A, Ried M, Wobus C, Lahm H, Leike K, Kleinschmidt J, Deleage G, Hallek M. 1999. Genetic capsid modifications allow efficient re-targeting of adeno-associated virus type 2. Nature medicine 5:1052-1056.
34. Harbison C E, Weichert W S, Gurda B L, Chiorini J A, Agbandje-McKenna M, Parrish C R. 2012. Examining the cross-reactivity and neutralization mechanisms of a panel of mAbs against adeno-associated virus serotypes 1 and 5. The Journal of general virology 93:347-355.
35. Kuck D, Kern A, Kleinschmidt J A. 2007. Development of AAV serotype-specific ELISAs using novel monoclonal antibodies. Journal of virological methods 140:17-24.
36. Coker S F, Lloyd A J, Mitchell E, Lewis G R, Coker A R, Shoolingin-Jordan P M. 2010. The high-resolution structure of pig heart succinyl-CoA:3-oxoacid coenzyme A transferase. Acta crystallographica. Section D, Biological crystallography 66:797-805.
37. Eisen M B, Sabesan S, Skehel J J, Wiley D C. 1997. Binding of the influenza A virus to cell-surface receptors: structures of five hemagglutinin-sialyloligosaccharide complexes determined by X-ray crystallography. Virology 232:19-31.
38. Lopez-Bueno A, Rubio M P, Bryant N, McKenna R, Agbandje-McKenna M, Almendral J M. 2006. Host-selected amino acid changes at the sialic acid binding pocket of the parvovirus capsid modulate cell binding affinity and determine virulence. Journal of virology 80:1563-1573.
39. Shen S, Troupes A N, Pulicherla N, Asokan A. 2013. Multiple roles for sialylated glycans in determining the cardiopulmonary tropism of adeno-associated virus 4. Journal of virology 87:13206-13213.
40. Thacker T C, Johnson F B. 1998. Binding of bovine parvovirus to erythrocyte membrane sialylglycoproteins. The Journal of general virology 79 (Pt 9):2163-2169.
41. Barbis D P, Chang S F, Parrish C R. 1992. Mutations adjacent to the dimple of the canine parvovirus capsid structure affect sialic acid binding. Virology 191:301-308.
42. Allaume X, El-Andaloussi N, Leuchs B, Bonifati S, Kulkarni A, Marttila T, Kaufmann J K, Nettelbeck D M, Kleinschmidt J, Rommelaere J, Marchini A. 2012. Retargeting of rat parvovirus H-1PV to cancer cells through genetic engineering of the viral capsid. Journal of virology 86:3452-3465.
43. Boisvert M, Fernandes S, Tijssen P. 2010. Multiple pathways involved in porcine parvovirus cellular entry and trafficking toward the nucleus. Journal of virology 84:7782-7792.
44. Palermo L M, Hafenstein S L, Parrish C R. 2006. Purified feline and canine transferrin receptors reveal complex interactions with the capsids of canine and feline parvoviruses that correspond to their host ranges. Journal of virology 80:8482-8492.
45. Xiao C, Rossmann M G. 2007. Interpretation of electron density with stereographic roadmap projections. Journal of structural biology 158:182-187.

The foregoing examples of the present disclosure have been presented for purposes of illustration and description. Furthermore, these examples are not intended to limit the disclosure to the form disclosed herein. Consequently, variations and modifications commensurate with the teachings of the description of the disclosure, and the skill or knowledge of the relevant art, are within the scope of the present disclosure. The specific embodiments described in the examples provided herein are intended to further explain the best mode known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art.

What is claimed is:

1. A modified adeno-associated virus (AAV) capsid protein comprising at least one non-native amino acid at a location corresponding to a location in an AAV5 capsid protein selected from the group consisting of L587, M569, Y585, and T571.

2. The modified capsid protein of claim 1, wherein the modified capsid protein is produced by modification of a capsid protein from an AAV virus selected from the group consisting of AAV1, AAV2, AAV3, AAV 3B, AAV4, AAV5, AAV6, AAV7, AAV8, AAV9, AVV10, AAV11, AAV12, BAAV, AAAV and AAV VR-942.

3. The modified AAV capsid protein of claim 1, wherein the modified capsid protein is produced by modification of a capsid protein from an AAV that binds sialic acid.

4. The modified AAV capsid protein of claim 1, wherein the modified capsid protein is produced from a native AAV capsid protein comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12.

5. The modified AAV capsid protein of claim 1, wherein the modified capsid protein is produced from a native AAV capsid protein comprising an amino acid sequence selected from the group consisting of SEQ ID NO:1, SEQ ID NO:4, SEQ ID NO:5 and SEQ ID NO:6.

6. The modified capsid protein of claim 1, wherein the modified capsid protein comprises a modification of a sialic acid-binding AAV capsid protein, and the one or more amino acid(s) substituted at the amino acid position(s) known to be involved in binding of the capsid protein to a cellular receptor, is/are amino acids that are not present at corresponding locations in sialic acid-binding AAV capsid proteins.

7. The modified capsid protein of claim 1, wherein the modified capsid protein comprises a modification of a non-sialic acid-binding AAV capsid protein, the amino acid(s) being substituted at the amino acid position known to be involved in binding of the capsid protein to a cellular receptor, is/are amino acids that are not present at corresponding locations in non-sialic acid-binding AAV capsid proteins.

8. The modified capsid protein of claim 1, wherein the modified capsid protein comprises at least one non-native amino acid at a location of the capsid protein that interacts with sialic acid.

9. The modified capsid protein of claim 1, wherein the modified capsid protein comprises at least one non-native amino acid in the A-site or the B-site of the modified capsid protein.

10. The modified capsid protein of claim 1, wherein the modified AAV capsid protein comprises an amino acid sequence of a wild type AAV1, AAV4, AAV5 or AAV6 capsid protein.

11. The modified capsid protein of claim 1, wherein the modified AAV capsid protein comprises an amino acid sequence selected from the group consisting of SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38 and SEQ ID NO:41.

12. A method for treating a disease in an individual, the method comprising administering to an individual in need of such treatment a recombinant virus comprising the modified AAV capsid protein of claim 1 and at least one heterologous nucleic acid molecule.

13. The method of claim 12, wherein the virus is administered to a tissue selected from a tissue of the eye, the CNS, the liver, the salivary gland, and a muscle tissue.

* * * * *